(12) United States Patent
Breitenbucher et al.

(10) Patent No.: US 7,250,427 B2
(45) Date of Patent: Jul. 31, 2007

(54) ARYL-SUBSTITUTED BENZIMIDAZOLE AND IMIDAZOPYRIDINE ETHERS

(75) Inventors: J. Guy Breitenbucher, Escondido, CA (US); Alice Lee-Dutra, San Diego, CA (US); Danielle K. Neff, San Diego, CA (US)

(73) Assignee: Janssen Pharmaceutica, N.V. (BE)

( * ) Notice: Subject to any disclaimer, the term of this patent is extended or adjusted under 35 U.S.C. 154(b) by 0 days.

(21) Appl. No.: 11/168,107

(22) Filed: Jun. 27, 2005

(65) Prior Publication Data

US 2006/0004039 A1   Jan. 5, 2006

Related U.S. Application Data

(60) Provisional application No. 60/584,460, filed on Jun. 30, 2004.

(51) Int. Cl.
*A61K 31/4184* (2006.01)
*C07D 235/12* (2006.01)

(52) U.S. Cl. ............... 514/322; 514/394; 546/199; 548/304.7; 548/309.4

(58) Field of Classification Search .......... 514/394, 514/322; 546/199; 548/304.7, 309.4
See application file for complete search history.

(56) References Cited

U.S. PATENT DOCUMENTS

| 5,059,621 A | 10/1991 | Shroot et al. | |
|---|---|---|---|
| 5,814,651 A * | 9/1998 | Duplantier et al. | ......... 514/394 |
| 2005/0070550 A1 | 3/2005 | Arienti et al. | |

FOREIGN PATENT DOCUMENTS

| EP | 0148431 A1 | 7/1985 |
|---|---|---|
| EP | 0209707 A2 | 1/1987 |
| EP | 0719765 A2 | 7/1996 |
| WO | WO 98/06703 A1 | 2/1998 |
| WO | WO 99/11627 A1 | 3/1999 |
| WO | WO 99/61019 A1 | 12/1999 |
| WO | WO 99/61020 A1 | 12/1999 |
| WO | WO 01/21771 A2 | 3/2001 |
| WO | WO 01/98465 A1 | 12/2001 |
| WO | WO 02/072090 A1 | 9/2002 |
| WO | WO 03/011219 A2 | 2/2003 |
| WO | WO 03/032984 A1 | 4/2003 |

OTHER PUBLICATIONS

Tominaga, K. et al. Role of Human Cds1 (Chk2) Kinase in DNA Damage Checkpoint and Its Regulation by p53. J. Biol. Chem. 1999, 274(44), 31463-31467.
Matsuoka, S. et al. Linkage of ATM to Cell Cycle Regulation by the Chk2 Protein Kinase. Science 1998, 282, 1893-1897.
Blasina, A. et al. A Human Homologue of the Checkpoint Kinase Cds1 Directly Inhibits Cdc25 Phosphatase. Curr. Biol. 1999, 9(1), 1-10.
Lee, J.-S. et al. hCds1-Mediated Phosphorylation of BRCA1 Regulates the DNA Damage Response. Nature 2000, 404, 201-204.
Falck, J. et al. The ATM-Chk2-Cdc25A Checkpoint Pathway Guards against Radioresistant DNA Synthesis. Nature 2001, 410, 842-847.
Buscemi, G. et al, Chk2 Activation Dependence on Nbs1 after DNA Damage. Mol. Cell. Biol. 2001, 21(15), 5214-5222.
Hirao, A. et al. Chk2 Is a Tumor Suppressor That Regulates Apoptosis in both an Ataxia Telangiectasia Mutated (ATM)-Dependent and an ATM-Independent Manner Mol. Cell. Biol. 2002, 22(18), 6521-6532.
Takai, H. et al. Chk2-Deficient Mice Exhibit Radioresistance and Defective p53-Mediated Transcription. EMBO J. 2002, 21(19), 5195-5205.
White, A.W et al. Resistance-Modifying Agents. 9. Synthesis and Biological Properties of Benzimidazole Inhibitors of the DNA Repair Enzyme Poly(ADP-ribose) Polymerase. J. Med. Chem. 2000, 43(22), 4084-4097.
Kim, J.S. et al. Structure-Activity Relationships of Benzimidazoles and Related Heterocycles as Topoisomerase I Poisons. Bioorg. Med. Chem. 1996, 4(4), 621-630.
McClure, K.J. et al. Novel Non-Benzimidazole Chk2 Kinase Inhibitors. Bioorg. Med. Chem. Lett. 2006, in press.
Arienti, K.L. et al. Checkpoint Kinase Inhibitors: SAR and Radioprotective Properties of a Series of 2-Arylbenzimidazoles. J. Med. Chem. 2005, 48, 1873-1885.
International Search Report dated Dec. 5, 2005, for corresponding international application PCT/US2005/023004.

* cited by examiner

*Primary Examiner*—Kamal A. Saeed
*Assistant Examiner*—Joseph R. Kosack
(74) *Attorney, Agent, or Firm*—John Harbour

(57) ABSTRACT

Aryl substituted benzimidazole and imidazo[4,5]pyridine ethers are described as inhibitors of Cds1 and useful as adjuvants to chemotherapy or radiation therapy in the treatment of cancer.

33 Claims, No Drawings

ARYL-SUBSTITUTED BENZIMIDAZOLE AND IMIDAZOPYRIDINE ETHERS

This application claims priority to provisional application, which is U.S. Ser. No. 60/584,460, filed Jun. 30, 2004. The complete disclosures of the aforementioned related U.S. patent applications are hereby incorporated herein by reference for all purposes.

FIELD OF THE INVENTION

The present invention relates to aryl-substituted benzimidazoles and imidazo[4,5]pyridines compounds, compositions containing them, and methods of using them.

BACKGROUND OF THE INVENTION

The maintenance of an intact genome is of crucial importance to every organism. The individual cell in a multicellular eukaryotic organism possesses sophisticated and intricate mechanisms to properly respond to DNA damage. Such mechanisms repair damaged DNA or trigger programmed cell death (apoptosis). In response to DNA damage, checkpoint kinases are thought to be intimately involved in these processes. These kinases are activated by upstream proteins, such as ATM (ataxia-telangiectasia mutated) and ATR (ataxia-telangiectasia mutated and rad3-related), and in turn trigger cell cycle arrest by inhibition of proteins such as Cdc25A or Cdc25C. The checkpoint kinases may also modulate the activity of other proteins that are thought to be involved in DNA repair and programmed cell death. Examples of such proteins are BRCA1 and p53.

The checkpoint kinase Cds1 (in man also known as Chk2) is conserved from yeast to man. A human homolog of the *Schizosaccharomyces pombe* Cds1 gene has been described (Tominaga, K. et al. *J. Biol. Chem.* 1999, 274(44), 31463-31467; Matsouka, S. et al. *Science* 1998, 282, 1893-1897; Blasina, A. et al. *Curr. Biol.* 1999, 9(1), 1-10). Human Cds1 was rapidly activated by phosphorylation in response to DNA damage in both normal cells and in p53-deficient cancer cells. High levels of hCds1 were observed in p53-deficient cells. In human cells Cds1 has been implicated in the regulation by phosphorylation of proteins such as p53, BRCA1, Cdc25A, and Cdc25C (See: Lee, J.-S. et al. *Nature* 2000, 404, 201-204; Falck, J. et al. *Nature* 2001, 410, 842-847; and Buscemi, G. et al. *Mol. Cell. Biol.* 2001, 21(15), 5214-5221). As described below, inhibition of Cds1 offers two strategies for improving the effectiveness of DNA-damaging cancer treatments.

Cancer cells are often deficient in the mechanisms responsible for maintaining an intact genome. In particular, they have often lost proper p53 function, which generally correlates with the progression of a tumor to a more aggressive state, such as the progression from a pre-invasive to invasive stage of colon cancer, or from a low grade to a high grade astrocytoma. Between 30% and 70% of all subtypes of tumors have a point mutation in one of the two p53 gene copies and have lost the other allele. P53-deficient cells are generally more resistant to radiation. It is thought that the lack of initiation of programmed cell death in cancer cells may render such cells less sensitive to DNA-damaging cancer treatments. The transcription factor p53 is of importance not only for the initiation of programmed cell death, but also in cell cycle arrest. Loss of p53 function may therefore leave cancer cells with limited protection against insult to the genome. Further disruption of DNA damage repair and cell cycle arrest by inhibition of kinases such as Cds1 could then render cancer cells unable to survive after DNA damage. Therefore, inhibition of Cds1 could, by removing the remaining components of DNA damage repair, render the cancer cells more susceptible to treatments such as chemical DNA-damaging agents or ionizing radiation.

Normal cells, on the other hand, have an intact p53 system, and will often undergo apoptosis in response to DNA-damaging treatments at a much lower dose than that required to kill cancer cells. Therefore, in such situations, normal cells will be at a disadvantage compared to cancer cells, and cancer treatments often have to be discontinued due to serious side effects caused by loss of normal cells before the cancer has been eradicated. Inhibition of Cds1, which would prevent this kinase from phosphorylating and thereby stabilizing p53, could therefore protect normal cells from the effects of ionizing radiation or DNA-damaging chemotherapeutics while still allowing these agents to be effective against p53-deficient cancer cells. This would have the effect of increasing the therapeutic potential of these agents. This view is supported by studies of mice deficient in Cds1 (See: Hirao, A. et al. *Mol. Cell. Biol.* 2002, 22(18), 6521-6532; Takai, H. et al. *EMBO J.* 2002, 21(19), 5195-5205; WO 01/98465 A1 Chugai Seiyaku Kabushiki Kaisha, Dec. 27, 2001). These animals showed increased resistance to the apoptosis caused by ionizing radiation over their wild-type counterparts. For example, it was shown that these animals were protected from apoptosis of intestinal cells, hair follicle cells, cells of the CNS, and thymus cells relative to their wild-type counterparts when treated with ionizing radiation. Cds1 knockout animals also showed increased survival when exposed to ionizing radiation. It is therefore logical to assume that chemical inhibitors of Cds1 would have therapeutic potential in the protection of patients from the deleterious side effects of radiation or DNA-damaging chemotherapeutics.

A p53 deficient tumor is a tumor wherein the functions mediated by p53 are lacking or suppressed due to genetic mutations in the gene encoding p53 or through deficiencies or disregulation of proteins that modulate p53 expression levels and function. Examples of such proteins are MDM2 and p14(ARF).

Additional examples of cell cycle checkpoint modulators in development include UCN-01 (CAS 112953-11-4), UCN-02, KW-2401, NSC-638850 (Kyowa Hakko/National Cancer Institute) and SB-218078 (CAS 135897-06-2) (Smith-Kline Beecham).

Additional relevant publications include DE 0148431 (T 7570), WO 01/21771 A2, WO 02/072090 A1, WO 03/011219 A2, and White, A. W. et al. *J. Med. Chem.* 2000, 43(22), 4084-4097.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety.

SUMMARY OF THE INVENTION

The present invention features compounds of formula (I):

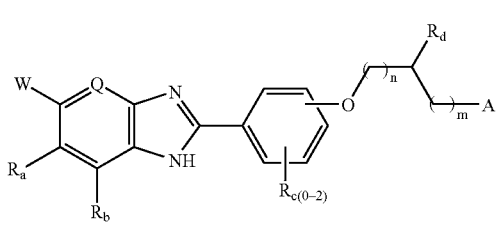

(I)

wherein
W is —COOH, —(CO)NH$_2$, or —(SO$_2$)NH$_2$;
Q is N or CH;
R$_a$ and R$_b$ are each independently selected from —H and halogen;
R$_c$ is absent or is independently selected from the group consisting of —OH, —CF$_3$, —C$_{1-4}$alkyl, —OC$_{1-4}$alkyl, —NO$_2$, and halo;
n is selected from the group consisting of 0, 1, and 2;
m is selected from the group consisting of 0, 1, and 2;
R$_d$ is —H or —C$_{1-4}$alkyl, optionally mono- or di-substituted with a substituent selected from the group consisting of —NH$_2$, —NHC$_{1-4}$alkyl, —N(C$_{1-4}$alkyl)$_2$, —OH, and —OC$_{1-4}$alkyl;
A is selected from the group consisting of —CR$_e$OH and —NR$_y$R$_z$, where if A is —NR$_y$R$_z$, m+n must be greater than zero;
R$_e$ is —H or —C$_{1-4}$alkyl, optionally mono- or di-substituted —C$_{1-4}$alkyl with a substituent selected from the group consisting of —NH$_2$, —NHC$_{1-4}$alkyl, —N(C$_{1-4}$alkyl)$_2$, —OH, —OC$_{1-4}$alkyl, —CF$_3$, and fluoro;
alternatively, R$_d$ and R$_e$ may be taken together with their carbons of attachment to form an aliphatic hydrocarbon ring, said ring having four to seven members, optionally having one or two unsaturated bonds in the ring, and optionally substituted with a substituent selected from the group consisting of —C$_{1-4}$alkyl, —OC$_{1-4}$alkyl, and fluoro;
R$_y$ is independently selected from the group consisting of —H, —C$_{1-4}$alkyl optionally substituted with —OC$_{1-4}$alkyl, and benzyl optionally mono- or di-substituted with —OC$_{1-4}$alkyl, —C$_{1-4}$alkyl, or halo;
alternatively, R$_d$ and R$_y$ may be taken together with their atoms of attachment to form a five to eight-membered heterocyclic ring, with the heterocyclic ring having zero or one unsaturated bonds, having zero, one, or two carbon members which is a carbonyl, having zero or one additional heteroatom members selected from the group consisting of O, S, —N=, >NH, and >NC$_{1-4}$alkyl and separated from the nitrogen of R$_y$ attachment by at least one carbon member, and optionally having a substituent selected from the group consisting of —C$_{1-4}$alkyl, —OC$_{1-4}$alkyl, and fluoro;
R$_z$ is —H or is selected from the group consisting of —C$_{1-6}$alkyl, —C$_{3-6}$cycloalkyl, —C$_{1-4}$alkylC$_{3-6}$cycloalkyl, phenyl, benzyl, pyridylmethyl, —C(O)C$_{1-6}$alkyl, —C(O)phenyl, —C(O)pyridyl, —C(O)OC$_{1-6}$alkyl, and —C(O)Obenzyl, each optionally mono-, di-, or tri-substituted with a substituent selected from the group consisting of —NH$_2$, —NHC$_{1-4}$alkyl, —N(C$_{1-4}$alkyl)$_2$, —OH, —OC$_{1-4}$alkyl, —C$_{1-4}$alkyl, and halo; and
alternatively, R$_y$ and R$_z$ may be taken together with the nitrogen of attachment to form an otherwise aliphatic hydrocarbon ring, said ring having five to seven members, optionally having one carbon replaced with >O, >S(=O)$_{0-2}$, =N—, >NH, and >N(C$_{1-4}$alkyl), optionally having one or two unsaturated bonds in the ring, and optionally having a substituent selected from the group consisting of —C$_{1-4}$alkyl, —OC$_{1-4}$alkyl, and fluoro;
and enantiomers, diastereomers, and pharmaceutically acceptable salts, esters or amides thereof.

The invention also features pharmaceutical compositions containing such compounds and methods of using such compositions in the treatment or prevention of cancer, particularly those that comprise p53-deficient tumors.

The invention also features a pharmaceutical composition comprising a compound of the invention and a pharmaceutically acceptable carrier; and methods of preparing or formulating such compositions. A composition of the invention may further include more than one compound of the invention, or a combination therapy (combination formulation or combination of differently formulated active agents).

The invention also provides methods of treating a subject suffering from cancer, said method comprising administering to said subject a therapeutically-effective amount of a compound or a pharmaceutical composition comprising a compound of formula (I) to a subject in need of such treatment.

Similarly, isomeric forms of the compounds of formula (I) and of their pharmaceutically acceptable salts, esters, and amides, are encompassed within the present invention, and reference herein to one of such isomeric forms is meant to refer to at least one of such isomeric forms. One of ordinary skill in the art will recognize that compounds according to this invention may exist, for example in a single isomeric form whereas other compounds may exist in the form of a regioisomeric mixture.

DETAILED DESCRIPTION OF THE INVENTION

Preferably, W is —(CO)NH$_2$.
Preferably, Q is CH.
Preferably, R$_a$ and R$_b$ are each independently —H, —Cl, or —F.
More preferably, R$_a$ is —H and R$_b$ is —Cl or —F.
Even more preferably, R$_a$ and R$_b$ are —H.
Preferably, R$_c$ is absent or is selected from the group consisting of —OH, —CH$_3$, —CH$_2$CH$_3$, —F, —Cl, —Br, —I, —CF$_3$, and —OCH$_3$.
More preferably, R$_c$ is selected from the group consisting of —F, —Cl, —CH$_3$, and —OCH$_3$.
Even more preferably, R$_c$ is absent.
Preferably, R$_d$ is selected from the group consisting of —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, and —C(CH$_3$)$_3$, where the alkyl members are optionally mono- or di-substituted.
More preferably, R$_d$ is selected from the group consisting of —H, —CH$_3$, —CH$_2$CH$_3$, —CH$_2$CH$_2$OCH$_3$, and —CH$_2$CH$_2$N(CH$_3$)$_2$.
Even more preferably, R$_d$ is —H.
Preferably, R$_e$ is selected from the group consisting of —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, and —C(CH$_3$)$_3$, where the alkyl members are optionally mono- or di-substituted.
More preferably, R$_e$ is selected from the group consisting of —H, —CH$_3$, —CH$_2$CH$_3$, —CH$_2$CH$_2$OCH$_3$, and —CH$_2$CH$_2$N(CH$_3$)$_2$.

Even more preferably, $R_e$ is —H or —CH$_3$.

Preferably, $R_d$ and $R_e$ taken together with their carbons of attachment form a hydrocarbon ring selected from the group consisting of cyclopentyl, cyclopentenyl, cyclohexyl, fluorocyclohexyl, methoxycyohexyl, and cycloheptyl.

Even more preferably, $R_d$ and $R_e$ taken together with their carbons of attachment form cyclopentyl or cyclohexyl.

Preferably, $R_y$ is selected from the group consisting of —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, and —C(CH$_3$)$_3$, where the alkyl members are optionally mono- or di-substituted.

Preferably, $R_y$ is selected from the group consisting of —H, —CH$_3$, —CH$_2$CH$_3$, —CH$_2$CH$_2$OCH$_3$, —CH$_2$CH$_2$CH$_3$, —CH(CH$_3$)$_2$, —CH$_2$CH$_2$N(CH$_3$)$_2$, and —CH$_2$CH$_2$CH$_2$CH$_3$.

More preferably, $R_y$ is —H or —CH$_3$.

Preferably, $R_d$ and $R_y$ taken together with their atoms of attachment form a heterocyclic ring selected from the group consisting of pyrrolidine, pyrrolidinone, 2,3-dihydropyrrole, piperidine, piperidinone, morpholine, thiomorpholine, piperazine, and piperazinone, where the rings are optionally substituted.

More preferably, $R_d$ and $R_y$ taken together with their atoms of attachment form a heterocyclic ring selected from the group consisting of pyrrolidinyl, piperidinyl, 4-fluoropiperidinyl, 4-methoxypiperidinyl, and 3-methylpiperidinyl. Even more preferably, $R_d$ and $R_y$ taken together with their atoms of attachment form a piperidine ring.

Preferably, $R_z$ is —H or is selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, cyclopentyl, cyclohexyl, cyclopropylethyl, phenyl, benzyl, pyridylmethyl, acetyl, propionyl, benzoyl, —C(O)pyridyl, —C(O)OC(CH$_3$)$_3$, and —C(O)Obenzyl, where each group member is optionally mono-, di-, or tri-substituted.

More preferably, $R_z$ is selected from the group consisting of —CH$_3$, 4-methylbenzyl, 4-methoxybenzyl, 4-chlorobenzyl, 3,4-dichlorobenzyl, acetyl, trifluoroacetyl, benzoyl, and —C(O)C(CH$_3$)$_3$.

Preferably, $R_y$ and $R_z$ are taken together with the nitrogen of attachment to form a ring selected from the group consisting of pyrrolidine, pyrrolidinone, 2,3-dihydropyrrole, piperidine, piperidinone, morpholine, thiomorpholine, piperazine, and piperazinone, where said rings are optionally substituted.

More preferably, $R_y$ and $R_z$ are taken together with the nitrogen of attachment to form a ring selected from the group consisting of pyrrolidinyl, piperidinyl, 4-fluoropiperidinyl, 4-methoxypiperidinyl, and 3-methylpiperidinyl.

Even more preferably, $R_y$ and $R_z$ taken together with their atoms of attachment form a piperidine ring.

Compounds of the present invention include closely related, pharmaceutically acceptable forms thereof, such as hydrates or solvated forms; isotopically-labelled forms; masked or protected forms; and isomeric forms. It is understood that some compounds referred to herein are chiral and/or have geometric isomeric centers, for example E- and Z-isomers. The present invention encompasses all such optical isomers, including single enantiomers, enantiomeric mixtures, racemic mixtures diastereomers tautomers atropisomers, and geometric isomers; and mixtures thereof, that possess the activity that characterizes the compounds of this invention. In addition, certain compounds referred to herein can exist in solvated (such as hydrates) as well as unsolvated forms. It is understood that this invention encompasses all such solvated and unsolvated forms that possess the activity that characterizes the compounds of this invention. Where chemical symbols are used, it is understood that they are read from left to right, and that otherwise their spatial orientation has no significance.

The invention encompasses stereochemically isomeric forms including diastereoisomers, as well as mixtures thereof in any proportion of the compounds of the present invention. The compounds of the present invention may also exist in their tautomeric forms. Such forms, although not explicitly indicated in the above and following formulae, are intended to be included within the scope of the present invention. For example, the present invention includes

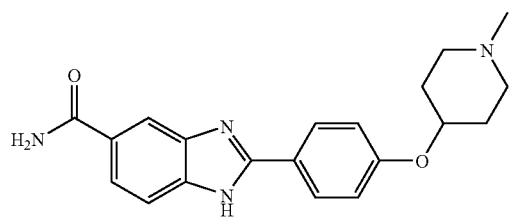

2-[4-(1-Methyl-piperidin-4-yloxy)-phenyl]-1H-benzoimidazole-5-carboxylic acid amide as well as

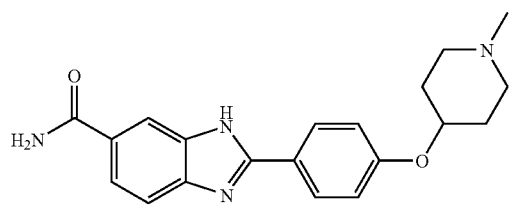

2-[4-(1-Methyl-piperidin-4-yloxy)-phenyl]-3H-benzoimidazole-5-carboxylic acid amide.

Compounds according to the present invention that have been modified to be detectable by some analytic technique are also within the scope of this invention. The compounds of the present invention may be labeled with radioactive elements such as $^{125}$I, $^{18}$F, $^{11}$C, $^{64}$Cu, and the like for use in imaging or for radioactive treatment of patients. An example of such compounds is an isotopically labeled compound, such as an $^{18}$F isotopically labeled compound that may be used as a probe in detection and/or imaging techniques, such as positron emission tomography (PET) and single-photon emission computed tomography (SPECT). Preferably, compounds of the present invention labeled with $^{18}$F or $^{11}$C may be used as a positron emission tomography (PET) molecular probe for studying Cds1-mediated disorders. Another example of such compounds is an isotopically labeled compound, such as a deuterium and/or tritium labeled compound, that may be used in reaction kinetic studies.

The compounds described herein may be reacted with an appropriate functionalized radioactive reagents using conventional chemistry to provide radiolabeled compounds.

Preferred compounds are selected from the group consisting of:

| EX | Compound Name |
|---|---|
| 1 | 2-[4-(3-Hydroxy-propoxy)-phenyl]-1H-benzoimidazole-5-carboxylic acid amide; |
| 2 | 2-[4-(2-Hydroxy-ethoxy)-phenyl]-1H-benzoimidazole-5-carboxylic acid amide; |

| EX | Compound Name |
|---|---|
| 3 | 2-[4-(3-Hydroxy-cyclopentyloxy)-phenyl]-1H-benzoimidazole-5-carboxylic acid amide; |
| 4 | 2-[4-(4-Hydroxy-cyclohexyloxy)-phenyl]-1H-benzoimidazole-5-carboxylic acid amide; |
| 5a | cis-2-[4-(4-Hydroxy-cyclohexylmethoxy)-phenyl]-1H-benzoimidazole-5-carboxylic acid amide; |
| 5b | trans-2-[4-(4-Hydroxy-cyclohexylmethoxy)-phenyl]-1H-benzoimidazole-5-carboxylic acid amide; |
| 6 | 2-[3-(3-Dimethylamino-propoxy)-phenyl]-1H-benzoimidazole-5-carboxylic acid amide; |
| 7 | 2-[4-(3-Dimethylamino-propoxy)-phenyl]-1H-benzoimidazole-5-carboxylic acid amide; |
| 8 | 2-[4-(3-Piperidin-1-yl-propoxy)-phenyl]-1H-benzoimidazole-5-carboxylic acid amide; |
| 9 | 2-[4-(2-Piperidin-1-yl-ethoxy)-phenyl]-1H-benzoimidazole-5-carboxylic acid amide; |
| 10 | 2-[4-(1-Methyl-piperidin-4-yloxy)-phenyl]-1H-benzoimidazole-5-carboxylic acid amide; |
| 11 | 2-[4-(1-Benzyl-piperidin-4-yloxy)-phenyl]-1H-benzoimidazole-5-carboxylic acid amide; |
| 12 | 2-[4-(1-Benzyl-piperidin-3-yloxy)-phenyl]-1H-benzoimidazole-5-carboxylic acid amide; |
| 13 | 2-[4-(1-Methyl-pyrrolidin-3-yloxy)-phenyl]-1H-benzoimidazole-5-carboxylic acid amide; |
| 14 | 2-[4-(1-Benzyl-pyrrolidin-3-yloxy)-phenyl]-1H-benzoimidazole-5-carboxylic acid amide; |
| 15 | 2-{2-[4-(5-Carbamoyl-1H-benzoimidazol-2-yl)-phenoxy]-ethyl}-piperidine-1-carboxylic acid tert-butyl ester; |
| 16 | 4-{2-[4-(5-Carbamoyl-1H-benzoimidazol-2-yl)-phenoxy]-ethyl}-piperidine-1-carboxylic acid tert-butyl ester; |
| 17 | 3-[4-(5-Carbamoyl-1H-benzoimidazol-2-yl)-phenoxy]-piperidine-1-carboxylic acid tert-butyl ester; |
| 18 | 4-[4-(5-Carbamoyl-1H-benzoimidazol-2-yl)-phenoxy]-piperidine-1-carboxylic acid tert-butyl ester; |
| 19 | 4-[4-(5-Carbamoyl-1H-benzoimidazol-2-yl)-phenoxymethyl]-piperidine-1-carboxylic acid tert-butyl ester; |
| 20 | 3-[4-(5-Carbamoyl-1H-benzoimidazol-2-yl)-phenoxymethyl]-piperidine-1-carboxylic acid tert-butyl ester; |
| 21 | 2-[4-(2-Piperidin-2-yl-ethoxy)-phenyl]-1H-benzoimidazole-5-carboxylic acid amide; |
| 22 | 2-[4-(2-Piperidin-4-yl-ethoxy)-phenyl]-1H-benzoimidazole-5-carboxylic acid amide; |
| 23 | 2-[4-(Piperidin-3-yloxy)-phenyl]-1H-benzoimidazole-5-carboxylic acid amide; |
| 24 | 2-[4-(Piperidin-4-yloxy)-phenyl]-1H-benzoimidazole-5-carboxylic acid amide; |
| 25 | 2-[4-(Piperidin-4-ylmethoxy)-phenyl]-1H-benzoimidazole-5-carboxylic acid amide; |
| 26 | 2-[4-(Piperidin-3-ylmethoxy)-phenyl]-1H-benzoimidazole-5-carboxylic acid amide; |
| 27 | 2-(4-{2-[1-(4-Methyl-benzyl)-piperidin-2-yl]-ethoxy}-phenyl)-1H-benzoimidazole-5-carboxylic acid amide; |
| 28 | 2-(4-{2-[1-(4-Methoxy-benzyl)-piperidin-2-yl]-ethoxy}-phenyl)-1H-benzoimidazole-5-carboxylic acid amide; |
| 29 | 2-(4-{2-[1-(4-Chloro-benzyl)-piperidin-2-yl]-ethoxy}-phenyl)-1H-benzoimidazole-5-carboxylic acid amide; |
| 30 | 2-(4-{2-[1-(3,4-Dichloro-benzyl)-piperidin-2-yl]-ethoxy}-phenyl)-1H-benzoimidazole-5-carboxylic acid amide; |
| 31 | 2-{4-[2-(1-Benzyl-piperidin-2-yl)-ethoxy]-phenyl}-1H-benzoimidazole-5-carboxylic acid amide; |
| 32 | 2-{4-[2-(1-Benzyl-piperidin-4-yl)-ethoxy]-phenyl}-1H-benzoimidazole-5-carboxylic acid amide; |
| 33 | 2-(4-{2-[1-(4-Methyl-benzyl)-piperidin-4-yl]-ethoxy}-phenyl)-1H-benzoimidazole-5-carboxylic acid amide; |
| 34 | 2-(4-{2-[1-(4-Methoxy-benzyl)-piperidin-4-yl]-ethoxy}-phenyl)-1H-benzoimidazole-5-carboxylic acid amide; |
| 35 | 2-(4-{2-[1-(4-Chloro-benzyl)-piperidin-4-yl]-ethoxy}-phenyl)-1H-benzoimidazole-5-carboxylic acid amide; |
| 36 | 2-(4-{2-[1-(3,4-Dichloro-benzyl)-piperidin-4-yl]-ethoxy}-phenyl)-1H-benzoimidazole-5-carboxylic acid amide; |
| 37 | 2-{4-[1-(4-Chloro-benzyl)-piperidin-3-yloxy]-phenyl}-1H-benzoimidazole-5-carboxylic acid amide; |
| 38 | 2-[4-(1-Benzyl-piperidin-3-ylmethoxy)-phenyl]-1H-benzoimidazole-5-carboxylic acid amide; |
| 39 | 2-{4-[1-(4-Methyl-benzyl)-piperidin-3-ylmethoxy]-phenyl}-1H-benzoimidazole-5-carboxylic acid amide; |
| 40 | 2-{4-[1-(4-Methoxy-benzyl)-piperidin-3-ylmethoxy]-phenyl}-1H-benzoimidazole-5-carboxylic acid amide; |
| 41 | 2-{4-[1-(4-Chloro-benzyl)-piperidin-3-ylmethoxy]-phenyl}-1H-benzoimidazole-5-carboxylic acid amide; |
| 42 | 2-{4-[1-(3,4-Dichloro-benzyl)-piperidin-3-ylmethoxy]-phenyl}-1H-benzoimidazole-5-carboxylic acid amide; |
| 43 | 2-[4-(1-Benzyl-piperidin-4-ylmethoxy)-phenyl]-1H-benzoimidazole-5-carboxylic acid amide; |
| 44 | 2-{4-[1-(4-Methyl-benzyl)-piperidin-4-ylmethoxy]-phenyl}-1H-benzoimidazole-5-carboxylic acid amide; |
| 45 | 2-{4-[1-(4-Methoxy-benzyl)-piperidin-4-ylmethoxy]-phenyl}-1H-benzoimidazole-5-carboxylic acid amide; |
| 46 | 2-{4-[1-(4-Methoxy-benzyl)-piperidin-4-ylmethoxy]-phenyl}-1H-benzoimidazole-5-carboxylic acid amide; |
| 47 | 2-{4-[1-(3,4-Dichloro-benzyl)-piperidin-4-ylmethoxy]-phenyl}-1H-benzoimidazole-5-carboxylic acid amide; |
| 48 | 2-{4-[2-(1-Acetyl-piperidin-2-yl)-ethoxy]-phenyl}-1H-benzoimidazole-5-carboxylic acid amide; |
| 49 | 2-{4-[2-(1-Acetyl-piperidin-4-yl)-ethoxy]-phenyl}-1H-benzoimidazole-5-carboxylic acid amide; |
| 50 | 2-[4-(1-Acetyl-piperidin-3-yloxy)-phenyl]-1H-benzoimidazole-5-carboxylic acid amide; |
| 51 | 2-[4-(1-Acetyl-piperidin-4-yloxy)-phenyl]-1H-benzoimidazole-5-carboxylic acid amide; |
| 52 | 2-[4-(1-Acetyl-piperidin-4-ylmethoxy)-phenyl]-1H-benzoimidazole-5-carboxylic acid amide; |
| 53 | 2-[4-(1-Acetyl-piperidin-3-ylmethoxy)-phenyl]-1H-benzoimidazole-5-carboxylic acid amide; |
| 54 | 2-{4-[2-(1-Benzoyl-piperidin-2-yl)-ethoxy]-phenyl}-1H-benzoimidazole-5-carboxylic acid amide; |
| 55 | 2-{4-[2-(1-Benzoyl-piperidin-4-yl)-ethoxy]-phenyl}-1H-benzoimidazole-5-carboxylic acid amide; and |
| 56 | 2-[4-(1-Benzoyl-piperidin-4-ylmethoxy)-phenyl]-1H-benzoimidazole-5-carboxylic acid amide. |

More preferred are compounds selected from the group consisting of:

| EX | Compound Name |
|---|---|
| 2 | 2-[4-(2-Hydroxy-ethoxy)-phenyl]-1H-benzoimidazole-5-carboxylic acid amide; |
| 5a | cis-2-[4-(4-Hydroxy-cyclohexylmethoxy)-phenyl]-1H-benzoimidazole-5-carboxylic acid amide; |
| 11 | 2-[4-(1-Benzyl-piperidin-4-yloxy)-phenyl]-1H-benzoimidazole-5-carboxylic acid amide; |
| 12 | 2-[4-(1-Benzyl-piperidin-3-yloxy)-phenyl]-1H-benzoimidazole-5-carboxylic acid amide; |
| 17 | 3-[4-(5-Carbamoyl-1H-benzoimidazol-2-yl)-phenoxy]-piperidine-1-carboxylic acid tert-butyl ester; |
| 19 | 4-[4-(5-Carbamoyl-1H-benzoimidazol-2-yl)-phenoxymethyl]-piperidine-1-carboxylic acid tert-butyl ester; |
| 27 | 2-(4-{2-[1-(4-Methyl-benzyl)-piperidin-2-yl]-ethoxy}-phenyl)-1H-benzoimidazole-5-carboxylic acid amide; |
| 28 | 2-(4-{2-[1-(4-Methoxy-benzyl)-piperidin-2-yl]-ethoxy}-phenyl)-1H-benzoimidazole-5-carboxylic acid amide; |
| 29 | 2-(4-{2-[1-(4-Chloro-benzyl)-piperidin-2-yl]-ethoxy}-phenyl)-1H-benzoimidazole-5-carboxylic acid amide; |
| 30 | 2-(4-{2-[1-(3,4-Dichloro-benzyl)-piperidin-2-yl]-ethoxy}-phenyl)-1H-benzoimidazole-5-carboxylic acid amide; |
| 31 | 2-{4-[2-(1-Benzyl-piperidin-2-yl)-ethoxy]-phenyl}-1H-benzoimidazole-5-carboxylic acid amide; |
| 37 | 2-{4-[1-(4-Chloro-benzyl)-piperidin-3-yloxy]-phenyl}-1H-benzoimidazole-5-carboxylic acid amide; |
| 38 | 2-[4-(1-Benzyl-piperidin-3-ylmethoxy)-phenyl]-1H-benzoimidazole-5-carboxylic acid amide; |
| 39 | 2-{4-[1-(4-Methyl-benzyl)-piperidin-3-ylmethoxy]-phenyl}-1H-benzoimidazole-5-carboxylic acid amide; |
| 40 | 2-{4-[1-(4-Methoxy-benzyl)-piperidin-3-ylmethoxy]-phenyl}-1H-benzoimidazole-5-carboxylic acid amide; |
| 41 | 2-{4-[1-(4-Chloro-benzyl)-piperidin-3-ylmethoxy]-phenyl}-1H-benzoimidazole-5-carboxylic acid amide; |

-continued

| EX | Compound Name |
|---|---|
| 45 | 2-{4-[1-(4-Methoxy-benzyl)-piperidin-4-ylmethoxy]-phenyl}-1H-benzoimidazole-5-carboxylic acid amide; |
| 46 | 2-{4-[1-(4-Methoxy-benzyl)-piperidin-4-ylmethoxy]-phenyl}-1H-benzoimidazole-5-carboxylic acid amide; |
| 54 | 2-{4-[2-(1-Benzoyl-piperidin-2-yl)-ethoxy]-phenyl}-1H-benzoimidazole-5-carboxylic acid amide; |
| 55 | 2-{4-[2-(1-Benzoyl-piperidin-4-yl)-ethoxy]-phenyl}-1H-benzoimidazole-5-carboxylic acid amide; and |
| 56 | 2-[4-(1-Benzoyl-piperidin-4-ylmethoxy)-phenyl]-1H-benzoimidazole-5-carboxylic acid amide. |

Even more preferred are compounds selected from the group consisting

| EX | Compound Name |
|---|---|
| 19 | 4-[4-(5-Carbamoyl-1H-benzoimidazol-2-yl)-phenoxymethyl]-piperidine-1-carboxylic acid tert-butyl ester; |
| 29 | 2-(4-{2-[1-(4-Chloro-benzyl)-piperidin-2-yl]-ethoxy}-phenyl)-1H-benzoimidazole-5-carboxylic acid amide; |
| 30 | 2-(4-{2-[1-(3,4-Dichloro-benzyl)-piperidin-2-yl]-ethoxy}-phenyl)-1H-benzoimidazole-5-carboxylic acid amide; |
| 31 | 2-{4-[2-(1-Benzyl-piperidin-2-yl)-ethoxy]-phenyl}-1H-benzoimidazole-5-carboxylic acid amide; |
| 37 | 2-{4-[1-(4-Chloro-benzyl)-piperidin-3-yloxy]-phenyl}-1H-benzoimidazole-5-carboxylic acid amide; |
| 38 | 2-[4-(1-Benzyl-piperidin-3-ylmethoxy)-phenyl]-1H-benzoimidazole-5-carboxylic acid amide; |
| 41 | 2-{4-[1-(4-Chloro-benzyl)-piperidin-3-ylmethoxy]-phenyl}-1H-benzoimidazole-5-carboxylic acid amide; |
| 54 | 2-{4-[2-(1-Benzoyl-piperidin-2-yl)-ethoxy]-phenyl}-1H-benzoimidazole-5-carboxylic acid amide; |
| 55 | 2-{4-[2-(1-Benzoyl-piperidin-4-yl)-ethoxy]-phenyl}-1H-benzoimidazole-5-carboxylic acid amide; and |
| 56 | 2-[4-(1-Benzoyl-piperidin-4-ylmethoxy)-phenyl]-1H-benzoimidazole-5-carboxylic acid amide. |

Compounds according to the present invention may be made according to processes within the skill of the art and/or according to processes of this invention, such as those described in the schemes and examples that follow and by matrix or combinatorial methods. To obtain the various compounds herein, starting materials may be employed that carry the ultimately desired substituents though the reaction scheme with or without protection as appropriate. Starting materials may be obtained from commercial sources or synthesized by methods known to one skilled in the art.

Table of Acronyms

| Term | Acronym |
|---|---|
| 1-Hydroxybenzotriazole | HOBt |
| 1,1'-Carbonyldiimidazole | CDI |
| Ethyl acetate | EtOAc |
| Diisopropyl diazodicarboxylate | DIAD |
| 1-(3-Dimethylaminopropyl)-3-ethylcarbodiimide | EDC |
| Trifluoroacetic acid | TFA |
| 4-(Dimethylamino)pyridine | DMAP |
| High Performance Liquid Chromatography | HPLC |
| Tetrahydrofuran | THF |
| N,N-Dimethylacetamide | DMA |
| N,N-Dimethylformamide | DMF |
| Acetic acid | AcOH |
| Methyl sulfoxide | DMSO |

It may be necessary to employ, in the place of the ultimately desired substituent, a suitable group, which may be carried through the reaction scheme and replaced as appropriate with the desired substituent. In particular, during any of the processes for preparation of the compounds of the present invention, it may be necessary and/or desirable to protect sensitive or reactive groups (e.g., hydroxyl, amino, or carbonyl) on any of the molecules concerned. Such compounds, precursors, or prodrugs are also within the scope of the invention. This modification may be achieved by means of conventional protecting groups, such as those described in "Protective Groups in Organic Chemistry", J. F. W. McOmie, ed., Plenum Press, 1973; and T. W. Greene & P. G. M. Wuts, "Protective Groups in Organic Synthesis", $3^{rd}$ ed., John Wiley & Sons, 1999. Some of these masked or protected compounds are pharmaceutically acceptable; others will be useful as intermediates. The protecting groups may be removed at a convenient subsequent stage using methods known in the art.

Embodiments of processes illustrated herein include, when chemically meaningful, one or more steps such as hydrolysis, halogenation, protection, and deprotection. These steps can be implemented in light of the teachings provided herein and the ordinary skill in the art.

Those of ordinary skill in the art will be able to modify and adapt the guidance provided herein to make compounds according to the present invention. The compounds of formula (I) may be prepared by a number of reaction schemes. Persons skilled in the art will recognize that certain compounds are more advantageously produced by one scheme as compared to the other. Synthetic intermediates and processes disclosed herein, and minor modifications thereof, are also within the scope of the invention.

Where the processes for the preparation of the compounds according to the invention give rise to mixture of stereoisomers, these isomers may be separated by conventional techniques such as resolution, for example by formation of diastereomeric salts, kinetic resolution including variants thereof, such as dynamic resolution, preferential crystallization, biotransformation, enzymatic transformation, and preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric amines, esters, or amides, followed by chromatographic separation and removal of the chiral auxiliary. Alternatively, the compounds may be separated using a chiral HPLC column. Regioisomeric mixtures may also be separated into their constituent regioisomers by conventional techniques. Similarly, compounds of the present invention may exist in atropisomeric forms, and such forms may be separated using conventional methods.

Examples of the described synthetic routes include Synthetic Examples 1 through 56. Compounds analogous to the target compounds of these examples can be made according to similar routes. Using these Schemes, the guidelines below, and the Examples, a person of skill in the art may develop analogous or similar methods for a given compound that are within the invention. The compounds of the present invention are useful in basic research and as pharmaceutical agents as described in the next section.

Scheme 1

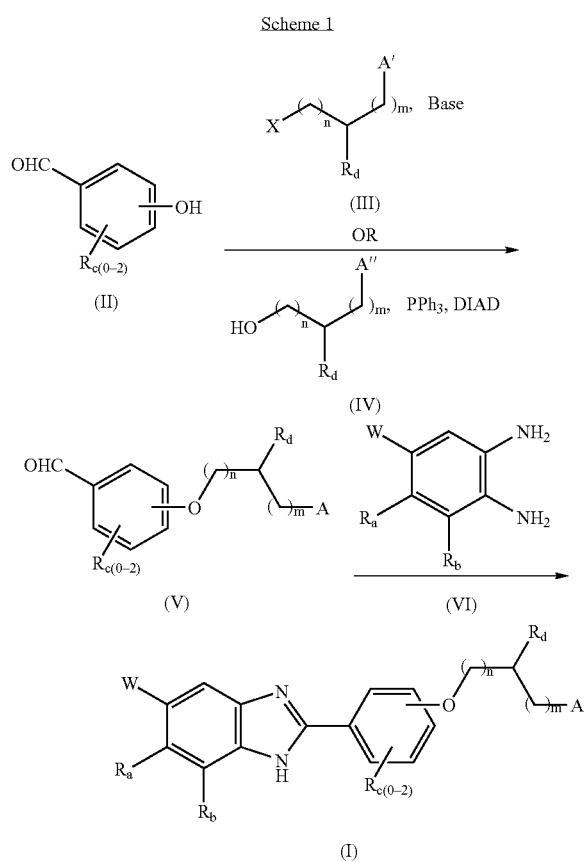

Broadly, compounds of formula I may be made according to scheme 1. Substituted hydroxy aldehydes of formula (II) may be commercially available or may be prepared using methods known to one skilled in the art. Aldehyde (II) can be converted to ethers of formula (V) using various means. In the case where A is —$CR_eOH$, phenols (II) can be alkylated with reagents (III) where A' represents —$CR_eOP$, if protection of the alcohol functionality is necessary, and X is a good leaving group such as bromide, chloride, iodide, oriosylate. Preferably, the leaving group is bromide. The alkylation is accomplished in the presence of a suitable base such as $Na_2CO_3$, $K_2CO_3$, or NaH, in a solvent such as DMF. Preferably, the base is $K_2CO_3$. Alternatively, where A is —$NR_yR_z$, alcohols of formula (IV) may be coupled with compounds of formula (II) under Mitsunobu conditions. Preferred conditions include $PPh_3$ and DIAD in a solvent such as $CH_2Cl_2$ or THF. Alkylating agents (III) and alcohols (IV) may be commercially available or may be prepared using methods known to one skilled in the art. Suitable protecting groups may be employed at various stages of the sequence, and, if desired, subsequently removed using methods known to one skilled in the art. For example, reactants of formula (IV) may be purchased or prepared where A" is an N-alkyl, N-benzyl, or N-Boc substituent prior to the alkylation step.

Aldehydes of formula (V) can be condensed with diamine (VI) in the presence of a dehydrating agent such as $Na_2S_2O_5$ to provide benzimidazoles (I). This reaction takes place in a solvent such as DMA or DMF, with the application of heat. Better yields might be obtained where the reaction is heated to a temperature of from 80° C. to 100° C.

Scheme 2

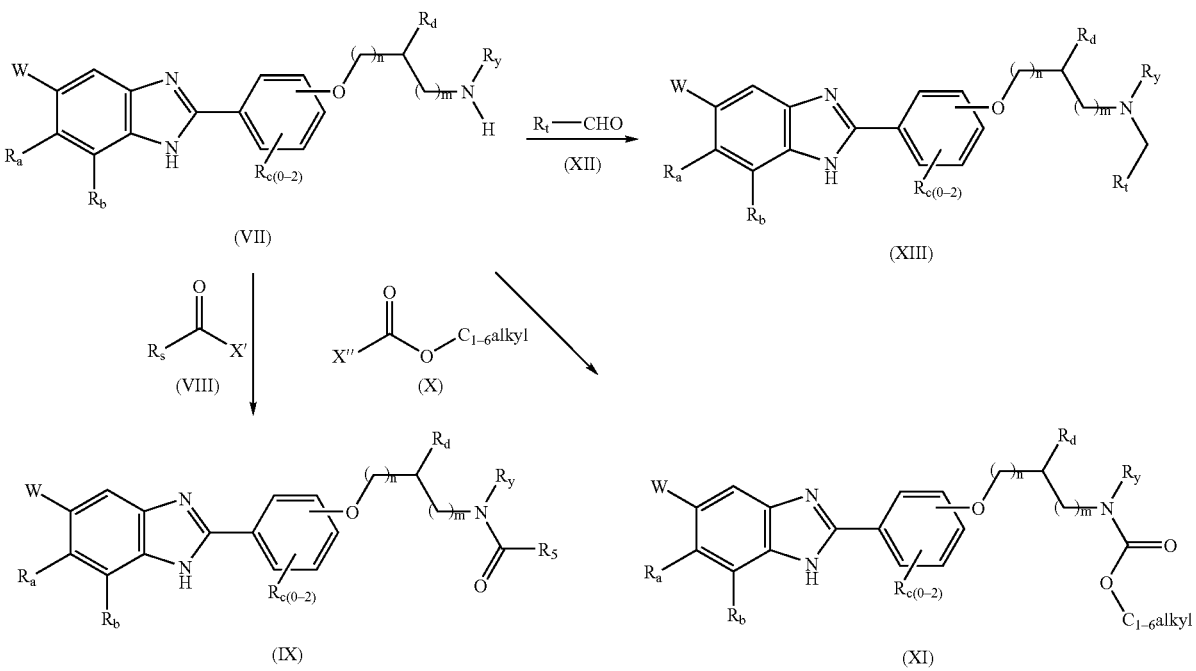

Compounds of formula (I) where A is —NHR$_y$, depicted in formula (VII), may be further processed into additional embodiments of formula (I) as shown in Scheme 2. Compounds of formula (VII) include primary (where R$_y$ is H) and secondary (where R$_y$ is alkyl, aryl, etc.) amines, and may be accessed using the sequence shown in Scheme 1. These amines (VII) may be acylated with agents of formula (VIII) where R$_s$ is optionally substituted C$_{1-6}$alkyl or phenyl, and X' is chosen to provide an adequate acylating agent. Where X' is halogen, preferably chloride, acylation occurs in the presence of a suitable base such as triethylamine in a solvent such as CH$_2$Cl$_2$. Where X' is —OH, acylation is accomplished using standard amino acid coupling methods. Preferred methods include CDI, or EDC/HOBt, in solvents such as THF.

If not purchased or introduced previously, carbamate groups may be introduced by reacting compounds of formula (VII) with a acyloxy reagent of formula (X) to form products of formula (XI). Where X" is chloride, a carbamoyl chloride reagent is employed. Where X" is —O(CO)C$_{1-6}$alkyl, a dicarbonate reagent is employed. Both reagents may be used with or without the presence of a suitable base, such as triethylamine, and in a suitable solvent such as CH$_2$Cl$_2$ or THF. Preferred reagents include di-tert-butyl-dicarbonate.

Amines of formula (VII) may also be reacted with aldehydes of formula (XII) under conditions of reductive amination to form alkylated amines (XIII), where R$_t$ is H, or optionally substituted —C$_{1-5}$alkyl or phenyl. Amines (VII) are treated with the aldehyde, with or without the addition of an activating agent such as molecular sieves, AcOH, or ZnCl$_2$, followed by a reducing agent such as NaCNBH$_3$ or Na(OAc)$_3$BH, in a solvent such as methanol, DMF, or THF. Preferred conditions employ molecular sieves and Na(OAc)$_3$BH in DMF. Alkyl and benzyl groups may also be introduced using standard amine alkylation chemistry known to one skilled in the art.

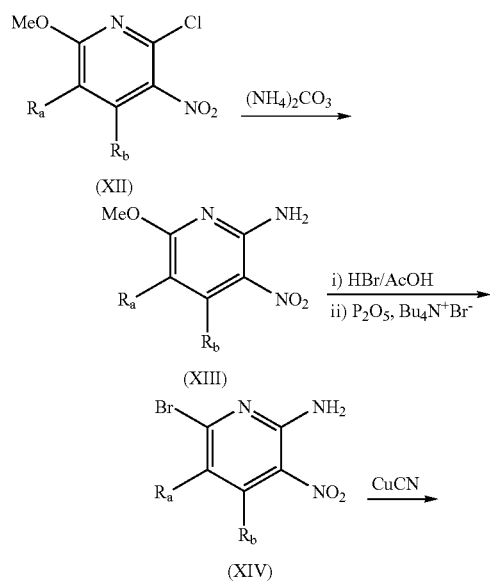

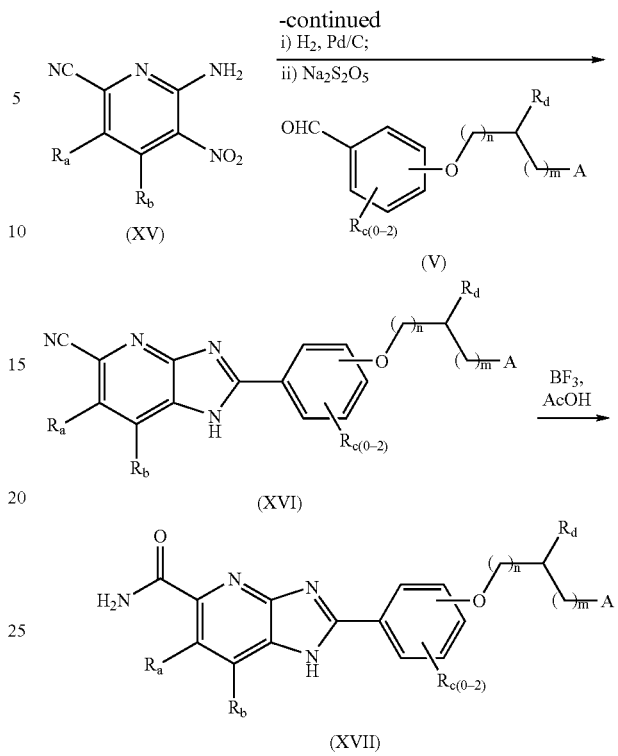

Compounds of general formula (XVII) can be synthesized using the methods outlined in Scheme 3. Treatment of pyridines (XII) with an ammonium equivalent such as (NH$_4$)$_2$CO$_3$ provides 2-aminopyridine (XII). Removal of the methyl group in (XII) with hydrobromic acid and acetic acid, followed by conversion to the bromide using a nucleophilic bromide source such as (C$_4$H$_9$)$_4$N$^+$Br$^-$, in the presence of P$_2$O$_5$, gives compounds (XIV). Treatment of the bromides with a metallic cyanide such as CuCN then results in the formation of compounds (XV). Reduction of the nitro group of (XV) using H$_2$ and Pd or other reducing agent, followed by condensation with an aryl aldehydes of type (V) in the presence of an oxidizing agent such as Na$_2$S$_2$O$_5$ provides imidazopyridines of general formula (XVI). The cyano group of (XVI) can then be converted to an amide of formula (XVII) by hydrolysis with BF$_3$ in acetic acid.

For therapeutic use, salts of the compounds of the present invention are those that are pharmaceutically acceptable. However, salts of acids and bases that are non-pharmaceutically acceptable may also find use, for example, in the preparation or purification of a pharmaceutically acceptable compound. All salts, whether pharmaceutically acceptable or not are included within the ambit of the present invention.

Pharmaceutically acceptable salts, esters, and amides of compounds according to the present invention refer to those salt, ester, and amide forms of the compounds of the present invention which would be apparent to the pharmaceutical chemist, i.e., those that are non-toxic and which would favorably affect the pharmacokinetic properties of said compounds of the present invention. Preferred salts, esters, and amides are those that are within a reasonable benefit/risk ratio, pharmacologically effective, and suitable for contact with the tissues of patients without undue toxicity, irritation, or allergic response. Salts, esters, and amides possess such pharmacokinetic properties to provide sufficient palatability, absorption, distribution, metabolism and excretion. Other factors, more practical in nature, which are also important in the selection, are cost of raw materials, ease of crystallization, yield, stability, hygroscopicity and flowability of the resulting bulk drug.

Examples of acids that may be used in the preparation of pharmaceutically acceptable salts include the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, ptoluenesulfonic acid and undecylenic acid.

Compounds of the present invention containing acidic protons may be converted into their therapeutically active non-toxic metal or amine addition salt forms by treatment with appropriate organic and inorganic bases. Appropriate base salt forms comprise, for example, the ammonium salts; the alkali and earth alkaline metal salts (e.g. lithium, sodium, potassium, magnesium, calcium salts, which may be prepared by treatment with, for example, magnesium hydroxide, calcium hydroxide, potassium hydroxide, zinc hydroxide, or sodium hydroxide); and amine salts made with organic bases (e.g. primary, secondary and tertiary aliphatic and aromatic amines such as L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine). See, e.g., S. M. Berge, et al., "Pharmaceutical Salts", J. Pharm. Sci., 1977, 66:1-19, which is incorporated herein by reference.

Examples of suitable esters include $C_{1-7}$alkyl, $C_{5-7}$cycloalkyl, phenyl, substituted phenyl, and phenyl$C_{1-6}$alkyl-esters. Preferred esters include methyl esters. Furthermore, examples of suitable esters include such esters where one or more carboxyl substituents is replaced with p-methoxybenzyloxy-carbonyl, 2,4,6-trimethylbenzyloxycarbonyl, 9-anthryloxycarbonyl, $CH_3SCH_2COO-$, tetrahydrofur-2-yloxycarbonyl, tetrahydropyran-2-yloxy-carbonyl, fur-2-yloxycarbonyl, benzoylmethoxycarbonyl, p-nitrobenzyloxy-carbonyl, 4-pyridylmethoxycarbonyl, 2,2,2-trichloroethoxycarbonyl, 2,2,2-tribromoethoxycarbonyl, t-butyloxycarbonyl, t-amyloxycarbonyl, diphenylmethoxy-carbonyl, triphenylmethoxycarbonyl, adamantyloxycarbonyl, 2-benzyloxyphenyloxycarbonyl, 4-methylthiophenyloxycarbonyl, or tetrahydropyran-2-yloxycarbonyl. Preferred pharmaceutically acceptable esters of the invention include $C_{1-7}$alkyl, $C_{5-7}$cycloalkyl, phenyl, and phenyl($C_{1-6}$)alkyl esters. More preferred esters include methyl esters.

Representative pharmaceutically acceptable amides of the invention include those derived from ammonia, primary $C_{1-6}$alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound that may not be specifically disclosed, but that converts to the specified compound in vivo after administration to the patient. Conventional procedures for the selection and preparation of suitable prodrug derivatives are described, for example, in "Design of Prodrugs", H. Bundgaard, ed., Elsevier, 1985.

The compounds of the present invention are Cds1 modulators, and as such, are useful, alone or in combination, in the treatment of patients (humans and other mammals) suffering from disorders or conditions that are modulated or regulated by Cds1, such as cancer. Compounds of the present invention are also useful as Cds1-inhibiting adjuvants. Where method involves the use or administration of a Cds1-inhibiting adjuvant, use or administration of at least one compound of the present invention will suffice.

Compounds of the present invention may be administered in pharmaceutical compositions to treat patients (humans and other mammals) suffering from disorders or conditions that are modulated or regulated by Cds1, such as cancer. The compounds of the present invention, alone or in combination, are useful for treating cancer in a subject in need thereof. Preferably, compounds of the present invention are useful in treating a p53-deficient cancer. Cancer types suitable for treatment with a compound of the present invention include cancers of the lung, prostate, colon, brain, head and neck, breast, stomach, liver, or ovary. A further aspect of the invention includes the treatment of a late-stage, e.g., stage 3 or stage 4, cancer.

The invention features a method for treating a subject with cancer, said method comprising administering to the subject a therapeutically effective amount of a pharmaceutical composition comprising at least one compound of the invention. The invention also provides a method for inhibiting Cds1 activity in a subject, wherein the method comprises administering to the subject a therapeutically effective amount of a pharmaceutical composition comprising at least one compound of the invention.

It is an object of the present invention to provide a Cds1-inhibiting adjuvant for use with ionizing radiation in the treatment of cancers.

It is another object of the present invention to provide a Cds1-inhibiting adjuvant for use with DNA-damaging chemotherapeutics in the treatment of cancers.

It is still another object of the present invention to provide a Cds1-inhibiting adjuvant for use with ionizing radiation and/or DNA-damaging chemotherapeutics that promotes the death of cancer cells damaged by such radiation or chemotherapeutics.

It is yet another object of the present invention to provide a Cds1-inhibiting adjuvant for use with ionizing radiation and/or DNA-damaging chemotherapeutics that prevents apoptosis of healthy cells damaged by such radiation or chemotherapeutics.

It is also an object of the present invention to provide a Cds1-inhibiting adjuvant for use with ionizing radiation and/or DNA-damaging chemotherapeutics that both promotes in a patient the death of cancer cells and prevents the apoptosis of healthy cells damaged by such radiation or chemotherapeutics.

It is also another object of the present invention to provide a Cds1-inhibiting adjuvant for use with ionizing radiation and/or DNA-damaging chemotherapeutics in the treatment of p53-deficient cancer cells.

It is an additional object of the present invention to provide a Cds1-inhibiting adjuvant for use with ionizing radiation and/or DNA-damaging chemotherapeutics that both promotes in a patient the death of p53-deficient cancer cells and prevents the apoptosis of healthy cells damaged by such radiation or chemotherapeutics.

It is an object of the present invention to provide a method for the treatment of cancer in a patient comprising exposing the cancer to ionizing radiation and administering a Cds1-inhibiting adjuvant.

It is another object of the present invention to provide a method for the treatment of cancer in a patient comprising administering a DNA-damaging chemotherapeutic and a Cds1-inhibiting adjuvant.

It is still another object of the present invention to provide a method to promote in a patient the death of cancer cells damaged by exposure to ionizing radiation and/or by administration of a DNA-damaging chemotherapeutic comprising the step of administering a Cds1-inhibiting adjuvant in conjunction with such therapies.

It is yet another object of the present invention to provide a method to prevent in a patient the apoptosis of healthy cells damaged by exposure to ionizing radiation and/or by administration of a DNA-damaging chemotherapeutic comprising the step of administering a Cds1-inhibiting adjuvant in conjunction with such therapies.

It is also an object of the present invention to provide a method to both promote in a patient the death of cancer cells and prevent the apoptosis of healthy cells damaged by exposure to ionizing radiation and/or by administration of a DNA-damaging chemotherapeutic comprising the step of administering a Cds1-inhibiting adjuvant in conjunction with such therapies.

It is also another object of the present invention to provide a method for the treatment of p53-deficient cancer cells in a patient comprising exposing the cancer cells to ionizing radiation and/or administering a DNA-damaging chemotherapeutic and administering a Cds1-inhibiting adjuvant.

It is an additional object of the present invention to provide a method to both promote in a patient the death of p53-deficient cancer cells and to prevent the apoptosis of healthy cells damaged by exposure to ionizing radiation and/or by administration of a DNA-damaging chemotherapeutic comprising the step of administering a Cds1-inhibiting adjuvant in conjunction with such therapies.

In another aspect, the invention provides a method for treating a subject suffering from a cancer, preferably comprising a p53-deficient tumor, said method comprising (a) administering to said subject a therapeutically effective amount of a pharmaceutical composition comprising at least one compound of formula (I) and (b) damaging the DNA of said subject, for example, by administration of a DNA-damaging treatment or agent, such as ionizing radiation or a chemical agent that causes DNA damage. In one aspect, the DNA damaging treatment is provided such that administration of the compound of formula (I) provides effective serum levels of the compound of formula (I) during the treatment and 12 hours to 5 days thereafter, for example, 1-2 days thereafter. In a further aspect, the method of treatment further includes administration of one or more additional anti-cancer agents, to provide in total three or four (or more) agents, to be administered in an effective anti-cancer amount. Multiple or combination therapies may allow use of lower amounts of one or more of the individual agents, when compared with monotherapy, and thereby reducing the incidence or degree of adverse effects.

Examples of such DNA-damaging chemical agents are compounds that cause DNA strand breaks directly such as bleomycin. DNA damage may also be caused by alkylating agents such as hexamethylamine, busulfan, carboplatin, carmustine, cisplatinum, cyclophosphamide, dacarbazine, ifosfamide, lomustine, mechlorethamine, melphalan, procarbazine, streptozocin or thiotepa, or combinations thereof. DNA damage may also be caused indirectly by topoisomerase inhibitors such as etoposide, irinotecan, teniposide, topotecan, and doxorubicin or by antimetabolites such as cladribine, cytarabine, floxuridine, 5-fluorouracil, gemcitibine, hydroxyurea, mercaptopurine, methotreaxate, pentostatin, thioguanine, and triemtrexate. Enhancement of DNA damaging effects and improved therapeutic responses can be obtained by combining anticancer agents such as those exemplified above.

The present invention also provides pharmaceutical compositions comprising one or more compounds of this invention in association with a pharmaceutically acceptable carrier and optionally additional pharmaceutical agents. The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes, or by inhalation. Preparations may also be designed to give slow release of the active ingredient. The preparation maybe in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives agents. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinyl-pyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or may be presented as a dry product for reconstitution with water or other suitable vehicles before use. Compositions of such liquid may contain pharmaceutically-acceptable excipients such as suspending agents (for example, sorbitol, methyl cellulose, sodium alginate, gelatin, hydroxyethylcellulose, carboxymethylcellulose, aluminium stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampules or disposable injection devices, in multi-dose forms such as vials from which the appropriate dose may be withdrawn, or in a solid form or pre-concentrate that can be used to prepare an injectable formulation. Another mode of administration of the compounds of the invention may utilize an ointment or a patch formulation to affect transdermal delivery. The compounds of this invention may also be administered by inhalation, via the nasal or oral routes using a spray formulation consisting of the compound of the invention and a suitable carrier.

Effective doses of the compounds of the present invention may be ascertained by conventional methods. The specific dosage level required for any particular patient will depend on a number of factors, including severity of the condition being treated, the route of administration, and the weight of the patient. Oral doses range from about 0.05 to 200 mg/kg, daily, taken in 1 to 4 separate doses. Some compounds of the invention may be orally dosed in the range of about 0.05 to about 50 mg/kg daily, others may be dosed at 0.05 to about 20 mg/kg daily, while still others may be dosed at 0.1 to about 10 mg/kg daily. Infusion doses can range from about 1 to 1000 mg/kg/min of inhibitor, admixed with a pharmaceutical carrier over a period ranging from several minutes to several days. For topical administration compounds of the present invention may be mixed with a pharmaceutical carrier at a concentration of about 0.1% to about 10% of drug to vehicle.

Methods are known in the art for determining effective doses for therapeutic and prophylactic purposes for the pharmaceutical compositions or the drug combinations of the present invention, whether or not formulated in the same composition. For therapeutic purposes, "effective dose" or "effective amount" refers to that amount of each active compound or pharmaceutical agent, alone or in combination, that elicits the biological or medicinal response in a tissue system, animal or human that is being sought by a researcher, veterinarian, medical doctor, or other clinician, which includes alleviation of the symptoms of the disease or disorder being treated. For prophylactic purposes (i.e., inhibiting the onset or progression of a disorder), the term "effective dose" or "effective amount" refers to that amount of each active compound or pharmaceutical agent, alone or in combination, that inhibits in a subject the onset or progression of a disorder as being sought by a researcher, veterinarian, medical doctor, or other clinician, the delaying of which disorder is mediated, at least in part, by the modulation of Cds1. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together. Combinations of three or more drugs are analogously possible. Methods of combination therapy include co-administration of a single formulation containing all active agents; essentially contemporaneous administration of more than one formulation; and administration of two or more active agents separately formulated.

EXAMPLES

General Experimental Details:

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Mass spectra were obtained on an Agilent series 1100 MSD using electrospray ionization (ESI) in either positive or negative mode as indicated.

HPLC retention times are reported in minutes, using the methods and conditions reported below.

Instrument: Agilent HP-1100
Solvent: $CH_3CN/H_2O/0.05\%$ TFA
Temperature: 30° C.
Wavelength: Dual detection at 220 nm and 254 nm
Method A: Chromolith SpeedRod column (6 µm, 4.6×50 mm) at 5 mL/min with a 3-minute linear gradient ramp from 15% $H_2O$ to 99% $H_2O$.
Method B: Xterra RP18 column (3.5 µm, 4.6×100 mm) at 1 mL/min with a 14-minute linear gradient ramp from 1% $H_2O$ to 99% $H_2O$.
Method C: Xterra RP18 column (3.5 µm, 4.6×100 mm) at 1 mL/min with a 10-minute linear gradient ramp from 1% $H_2O$ to 99% $H_2O$.

Example 1

2-[4-(3-Hydroxy-propoxy)-phenyl]-1H-benzoimidazole-5-carboxylic acid amide

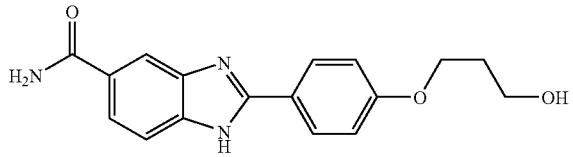

A. 4-(3-Hydroxy-propoxy)-benzaldehyde. To a solution of 4-hydroxybenzaldehyde (2.0 g, 16.4 mmol) and $K_2CO_3$ (3.9 g, 27.8 mmol) in DMF (20 mL) was added 3-bromopropanol (1.8 mL, 19.7 mmol). The mixture was stirred at room temperature (rt) for 16 h, diluted with $H_2O$ (60 mL), and extracted with EtOAc (3×20 mL). The combined organic layers were washed with 1 N NaOH (2×), $H_2O$ (1×), and brine (1×). The organic layer was dried ($Na_2SO_4$) and concentrated to afford 3.2 g (89%) of a yellow oil. This crude material was used without further purification in the next step. HPLC (Method A): $R_f$=0.54. MS (ESI+): mass calcd. for $C_{10}H_{12}O_3$, 180.08; m/z found, 181.1 [M+H]$^+$. $^1$H NMR (500 MHz, $CDCl_3$): 9.88 (s, 1H), 7.83 (d, J=8.8 Hz, 2H), 7.00 (d, J=8.8 Hz, 2H), 4.21 (t, J=6.2 Hz, 2H), 3.89-3.86 (m, 2H), 2.06-2.12 (m, 2H).

B. 2-[4-(3-Hydroxy-propoxy)-phenyl]-1H-benzoimidazole-5-carboxylic acid. To a solution of 4-(3-hydroxy-propoxy)-benzaldehyde (0.38 g, 2.1 mmol) and 3,4-diaminobenzoic acid (0.29 g, 1.9 mmol) in DMF (7 mL) was added $Na_2S_2O_5$ (0.47 g, 2.5 mmol). The reaction mixture was heated at 90° C. for 16 h. After cooling to rt, the mixture was filtered, rinsing with DMF. This resultant solution was used immediately in the next step.

C. 2-[4-(3-Hydroxy-propoxy)-phenyl]-1H-benzoimidazole-5-carboxylic acid amide. To a solution of 2-[4-(3-hydroxy-propoxy)-phenyl]-1H-benzoimidazole-5-carboxylic acid (0.95 mmol) in DMF (10 mL) was added HOBt (0.26 g, 1.92 mmol) and 1,3-diisopropylcarbodiimide (0.15 mL, 0.95 mmol). The mixture was stirred at rt for 15 min. Meanwhile, Rink amide resin (0.52 g, 0.32 mmol) was treated with 20% piperidine in DMF (6 mL) for 15 min. The resin was then successively rinsed with DMF (50 mL), methanol (50 mL), $CH_2Cl_2$ (50 mL), and more DMF (50 mL). Following this final rinse, the activated ester solution was poured in a cartridge vessel containing the resin, and the mixture was agitated on an orbital shaker for 18 h. Upon filtration, the resin was rinsed with DMF (50 mL), THF (50 mL), methanol (50 mL) and $CH_2Cl_2$ (50 mL). The resin was treated with 20% TFA in $CH_2Cl_2$ with 3% triethylsilane (15 mL) for 45 min. Filtration and rinsing with $CH_2Cl_2$ provided a solution that was azeotropically concentrated with toluene to provide the crude product as a brown residue. Further purification through reverse phase HPLC (C18; $H_2O$/$CH_3CN$/0.01% TFA) provided 40 mg (14%) of the title product. HPLC (Method C): $R_f$=4.10. MS (ESI+): mass calcd. for $C_{17}H_{17}N_3O_3$, 311.34; m/z found, 312.1 [M+H]$^+$. $^1$H NMR (500 MHz, $CD_3OD$): 8.28 (s, 1H), 8.11 (d, J=8.8 Hz, 2H), 8.06 (d, J=8.8 Hz, 1H), 7.81 (d, J=9.0 Hz, 1H), 7.27 (d, J=9.0 Hz, 2H), 4.26 (t, J=6.2 Hz, 2H), 3.35 (t, J=6.2 Hz, 2H), 2.08-2.02 (m, 2H).

Example 2

2-[4-(2-Hydroxy-ethoxy)-phenyl]-1H-benzoimidazole-5-carboxylic acid amide

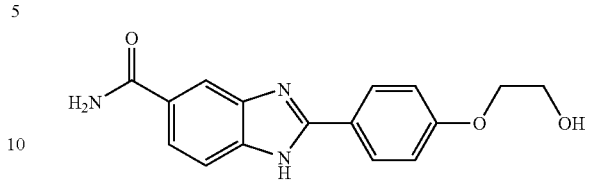

This compound was prepared using the methods outlined in Example 1, substituting bromoethanol for bromopropanol. HPLC (Method C): $R_f$=3.91. MS (ESI+): mass calcd. for $C_{16}H_{15}N_3O_3$, 297.11; m/z found, 298.1 [M+H]$^+$. $^1$H NMR (500 MHz, $CD_3OD$): 8.17 (s, 1H), 8.00 (d, J=9.1 Hz, 2H), 7.95 (d, J=8.7 Hz, 1H), 7.71 (d, J=8.5 Hz, 1H), 7.17 (d, J=9.1 Hz, 2H), 4.11 (t, J=4.7 Hz, 2H), 3.83 (t, J=4.7 Hz, 2H).

Example 3

2-[4-(3-Hydroxy-cyclopentyloxy)-phenyl]-1H-benzoimidazole-5-carboxylic acid amide

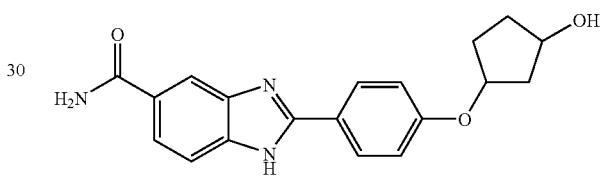

A. 4-(3-Hydroxy-cyclopentyloxy)-benzaldehyde. A solution of $Ph_3P$ (1.3 g, 5.0 mmol) and DIAD (1.0 g, 5.0 mmol) in $CH_2Cl_2$ (25 mL) was cooled to 0° C. After stirring for 15 min, 1,3-cyclopentanediol (0.5 g, 5.0 mmol) was added, followed by 4-hydroxy-benzaldehyde (0.6 g, 5.0 mmol). The mixture was stirred at rt for 48 h, then was diluted with satd. aq. $NaHCO_3$ (40 mL) and extracted with $CH_2Cl_2$ (3×, 20 mL). The combined organic layers were dried ($Na_2SO_4$) and concentrated. Purification by flash column chromatography (60% EtOAc in hexanes) yielded the desired aldehyde as a translucent yellow oil (0.4 g, 37%). $^1$H NMR (500 MHz, $CD_3OD$): 9.88 (s, 1H), 7.83 (d, J=8.8 Hz, 2H), 6.98 (d, J=8.5 Hz, 2H), 4.93-4.89 (m, 1H), 4.42-4.38 (m, 1H), 2.15-1.91 (m, 6H).

B. 2-[4-(3-Hydroxy-cyclopentyloxy)-phenyl]-1H-benzoimidazole-5-carboxylic acid. To a solution of the aldehyde (0.4 g, 1.7 mmol) and 3,4 diaminobenzoic acid (0.3 g, 1.7 mmol) in DMF (9 mL) was added $Na_2S_2O_5$ (0.4 g, 2.2 mmol). The reaction mixture was heated at 90° C. for 12 h. After cooling to rt, the mixture was filtered and rinsed with additional DMF (5 mL). This resultant solution was used immediately in the next step.

C. 2-[4-(3-Hydroxy-cyclopentyloxy)-phenyl]-1H-benzoimidazole-5-carboxylic acid amide. To a solution of 2-[4-(3-hydroxy-cyclopentyloxy)-phenyl]-1H-benzoimidazole-5-carboxylic acid (1.7 mmol) in DMF (6 mL) was added HOBt (0.5 g, 3.4 mmol) and 1,3-diisopropylcarbodiimide (0.2 mL, 1.7 mmol). The mixture was stirred at rt for 15 min. Meanwhile, Rink amide resin (1.9 g, 1.1 mmol) was treated with 20% piperidine in DMF (6 mL) for 15 min. The resin was then successively rinsed with DMF (50 mL), methanol (50 mL), $CH_2Cl_2$ (50 mL), and more DMF (50 mL). The activated ester solution was poured in a cartridge vessel containing the resin, and the mixture was agitated on an orbital shaker for 18 h. Upon filtration, the resin was rinsed with DMF (50 mL), THF (50 mL), methanol (50 mL) and CH$_2$Cl$_2$ (50 mL). The resin was treated with 20% TFA in CH$_2$Cl$_2$ with 3% triethylsilane (8 mL) for 1 h. Filtration and rinsing with CH$_2$Cl$_2$ provided a solution that was azeotropically concentrated with toluene to provide the crude product as a brown residue. Further purification through reverse phase HPLC (C18; H$_2$O/CH$_3$CN/0.01% TFA) provided 130 mg (23%) of the title product. HPLC (Method A): R$_t$=0.42. MS (ESI+): mass calcd. for C$_{19}$H$_{19}$N$_3$O$_3$, 337.14; m/z found, 338.1 [M+H]$^+$. $^1$H NMR (500 MHz, CD$_3$OD): 8.17 (d, J=1.0 Hz, 1H), 7.99 (d, J=11.9 Hz, 2H), 7.94 (dd, J=1.5, 8.6 Hz, 1H), 7.70 (d, J=8.7 Hz, 1H), 7.12 (d, J=7.0 Hz, 2H), 4.88-4.85 (m, 1H), 4.25-4.21 (m, 1H), 2.39-2.33 (m, 1H), 2.03-1.96 (m, 1H), 1.94-1.81 (m, 1H), 1.76-1.73 (m, 1H), 1.73-1.69 (m, 2H), 1.0 (d, J=6.5 Hz, 1H).

Example 4

2-[4-(4-Hydroxy-cyclohexyloxy)-phenyl]-1H-benzoimidazole-5-carboxylic acid amide

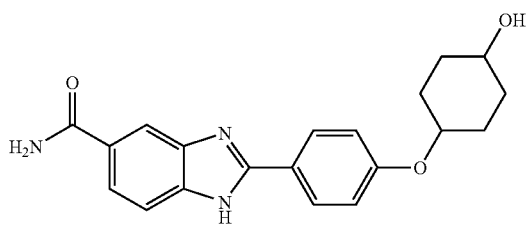

This compound was prepared using the methods outlined in Example 3, substituting 1,4-cyclohexanediol for 1,3-cyclopentanediol. HPLC (Method C): R$_t$=4.98. MS (ESI+): mass calcd. for C$_{20}$H$_{21}$N$_3$O$_3$, 351.16; m/z found, 352.2 [M+H]$^+$. $^1$H NMR (500 MHz, CD$_3$OD): 8.12 (s, 1H), 7.99-7.96 (m, 2H), 7.85 (d, J=8.5 Hz, 1H), 7.63 (d, J=8.4 Hz, 1H), 7.10 (t, J=9.3 Hz, 2H), 4.53-4.41 (m, 1H), 3.68-3.62 (m, 1H), 2.08-2.05 (m, 1H), 1.93-1.90 (m, 2H), 1.68-1.64 (m, 3H), 1.51-1.48 (m, 1H), 1.41-1.39 (m, 1H), 1.00 (d, J=6.5 Hz, 1H).

Example 5a cis-2-[4-(4-Hydroxy-cyclohexylmethoxy)-phenyl]-1H-benzoimidazole-5-carboxylic acid amide.

Example 5b trans-2-[4-(4-Hydroxy-cyclohexylmethoxy)-phenyl]-1H-benzoimidazole-5-carboxylic acid amide

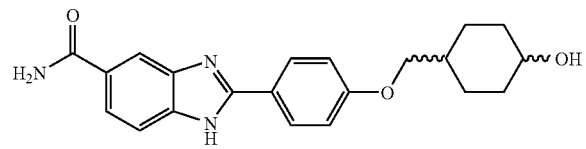

A. 4-(tert-Butyl-dimethyl-silanyloxy)-cyclohexanecarboxylic acid ethyl ester. To a solution of tert-butyldimethylsilyl chloride (10.6 g, 70 mmol) and imidazole (9.9 g, 145 mmol) in DMF (20 mL) was added 4-hydroxy-cyclohexanecarboxylic acid ethyl ester (9.4 mL, 58 mmol). The mixture was stirred at 35° C. for 12 h, diluted with EtOAc (100 mL), washed with H$_2$O (3×), dried (Na$_2$SO$_4$), and concentrated. The resulting white solid was isolated in quantitative yield (16.6 g) and was used in the next step without purification.

B. [4-tert-Butyl-dimethyl-silanyloxy)-cyclohexyl]-methanol. To a solution of LiAlH$_4$ (1 M in THF, 87 mL, 87 mmol) in THF (400 mL) was added 4-(tert-butyl-dimethyl-silanyloxy)-cyclohexanecarboxylic acid ethyl ester (16.6 g, 58 mmol). The mixture was stirred at 70° C. for 5 h, then was cooled to 0° C., diluted with H$_2$O (3.4 mL), and allowed to warm to rt. The mixture was then cooled again, treated with 10% aq. NaOH (3.4 mL), allowed to warm to rt, stirred for 15 min, cooled to 0° C., and quenched with H$_2$O (10 mL). Following 72 h of stirring at rt, the reaction mixture was filtered through diatomaceous earth, rinsing thoroughly with Et$_2$O. The filtrate was concentrated to yield a pale yellow oil. Flash column chromatography (60% EtOAc in hexanes) afforded the separated cis and trans isomers of the desired product as colorless oils (combined 14.2 g, 86%). Trans isomer: $^1$H NMR (500 MHz, CD$_3$OD): 3.96-3.93 (m, 1H), 3.31 ((d, J=5.8 Hz, 2H), 1.65-1.59 (m, 2H), 1.46-1.35 (m, 7H), 0.86 (s, 9H). Cis isomer: $^1$H NMR (500 MHz, CD$_3$OD): 3.54-3.47 (m, 1H), 3.28 (d, J=6.4 Hz, 2H), 1.85-1.80 (m, 2H), 1.76-1.71 (m, 2H), 1.37-1.28 (m, 1H), 1.26-1.18 (m, 2H), 0.96-0.88 (m, 2H), 0.834 (s, 9H).

C. 4-[4-(tert-Butyl-dimethyl-silanyloxy)-cyclohexyl-methoxy]-benzaldehyde. A solution of Ph$_3$P (0.6 g, 2.2 mmol) and DIAD (0.5 g, 2.2 mmol) in CH$_2$Cl$_2$ (7 mL) was cooled to 0° C. After stirring for 15 min, [4-(tert-butyl-dimethyl-silanyloxy)-cyclohexyl]-methanol (cis and trans run separately with 0.5 g, 2.0 mmol) was added, followed by 4-hydroxy-benzaldehyde (0.3 g, 2.2 mmol). The mixture stirred at rt for 24 h, then was diluted with 1 N NaOH (25 mL) and extracted with CH$_2$Cl$_2$ (3×, 20 mL). The combined organic layers were dried (Na$_2$SO$_4$) and concentrated. Purification by flash column chromatography (40% EtOAc in hexanes) yielded the separate cis and trans aldehydes (54% for both cis and trans reactions). Trans isomer: $^1$H NMR (500 MHz, CD$_3$OD): 9.76 (s, 1H), 7.79 (d, J=9.1 Hz, 2H), 7.00 (d, J=8.8 Hz, 2H), 3.99-3.96 (m, 1H), 3.84 (d, J=6.3 Hz, 2H), 3.26-3.24 (m, 1H), 1.81-1.74 (m, 1H), 1.68-1.63 (m, 1H), 1.57-1.53 (m, 1H), 1.50-1.44 (m, 1H), 0.85 (s, 9H). Cis isomer: $^1$H NMR (500 MHz, CD$_3$OD): 9.74 (s, 1H), 7.77 (d, J=8.5 Hz, 2H), 6.98 (d, J=8.8 Hz, 2H), 3.82 (d, J=6.5 Hz, 2H), 3.58-3.52 (m, 1H), 1.88-1.82 (m, 4H), 1.73-1.65 (m, 1H), 1.31-1.23 (m, 2H), 1.15-1.06 (m, 2H), 0.82 (s, 9H).

D. 2-[4-(4-Hydroxy-cyclohexylmethoxy)-phenyl]-1H-benzoimidazole-5-carboxylic acid amide. To a solution of 4-[4-(tert-butyl-dimethyl-silanyloxy)-cyclohexylmethoxy]-benzaldehyde (0.10 g, 0.29 mmol) and 3,4-diaminobenzamide (0.04 g, 0.29 mmol) in DMF (1 mL) was added Na$_2$S$_2$O$_5$ (0.07 g, 0.37 mmol). The mixture was heated to 90° C. for 12 h. The mixture was cooled to rt, filtered, and purified by reverse phase HPLC (C18; H$_2$O/CH$_3$CN/0.01% TFA). The acidic HPLC conditions removed the silyl-protecting group to afford the cis (5%) and trans (2%) products as TFA salts. Trans isomer: HPLC (Method C): R$_t$=5.00. MS (ESI+): mass calcd. for C$_{21}$H$_{23}$N$_3$O$_3$, 365.17; m/z found, 366.5 [M+H]$^+$. $^1$H NMR (500 MHz, CD$_3$OD): 8.20-8.19 (m, 1H), 8.02 (d, J=9.0 Hz, 2H), 7.97 (d, J=2.0, 8.5 Hz, 1H), 7.72 (d, J=9.0 Hz, 1H), 7.19-7.16 (m, 2H), 3.92 (d, J=6.0 Hz, 2H), 3.90-3.88 (m, 1H), 1.90-1.80 (m, 1H), 1.75-1.64 (m, 2H), 1.62-1.50 (m, 6H). Cis isomer: HPLC (Method C): R$_t$=5.24. MS (ESI+): mass calcd. for $C_{21}H_{23}N_3O_3$, 365.17; m/z found, 366.5 [M+H]$^+$. $^1$H NMR (500 MHz, DMSO-d$_6$): 8.19-8.18 (m, 1H), 8.15 (d, J=9.0 Hz, 2H), 8.13-8.11 (m, 1H), 7.91 (dd, J=1.5, 8.5 Hz, 1H), 7.72 (d, J=8.5 Hz, 1H), 7.43 (br s, 1H), 7.21 (d, J=9.0 Hz, 2H), 3.91 (d, J=6.5 Hz, 3H), 1.91-1.81 (m, 4H), 1.74-1.66 (m, 1H), 1.23-1.03 (m, 4H).

Example 6

2-[3-(3-Dimethylamino-propoxy)-phenyl]-1H-benzoimidazole-5-carboxylic acid amide

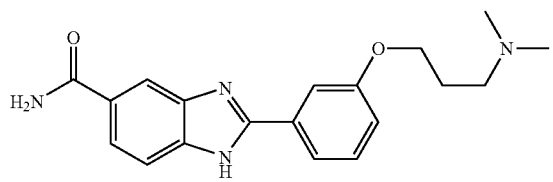

A. 3-(3-Dimethylamino-propoxy)-benzaldehyde. To 0° C. solution of Ph$_3$P (3.2 g, 12 mmol) in CH$_2$Cl$_2$ (15 mL) was slowly added diisopropyl azodicarboxylate (2.4 mL, 12 mmol). This solution was stirred at 0° C. for 15 min before the addition of 3-hydroxybenzaldehyde (1.5 g, 12 mmol), 3-dimethylamino-1-propanol (1.5 mL, 12 mmol), and CH$_2$Cl$_2$ (15 mL). The mixture was allowed to warm to rt, was stirred for 16 h and then was extracted with 1 N HCl (3×). The combined aqueous layers were treated with K$_2$CO$_3$ and extracted with CH$_2$Cl$_2$ (4×). The organic layers were combined, dried (Na$_2$SO$_4$), and concentrated. Purification through flash column chromatography (1% satd. NH$_3$ in methanol/9% methanol/90% CH$_2$Cl$_2$) provided 0.85 g (34%) of the aldehyde. HPLC (Method A): R$_f$=0.28. MS (ESI+): mass calcd. for $C_{12}H_{17}NO_2$, 207.13; m/z found, 208.2 [M+H]$^+$. $^1$H NMR (400 MHz, CD$_3$OD): 9.94(s, 1H), 7.49-7.46 (m, 2H), 7.43-7.42 (m, 1H), 7.25-7.21 (m, 1H), 4.08 (t, J=6.2 Hz, 2H), 2.55-2.51 (m, 2H), 2.28 (s, 6H), 2.02-1.95 (m, 2H).

B. 2-[3-(3-Dimethylamino-propoxy)-phenyl]-1H-benzoimidazole-5-carboxylic acid. To a solution of the aldehyde (0.28 g, 1.4 mmol) and 3,4-diaminobenzoic acid (0.19 g, 1.2 mmol) in DMF (3 mL) was added Na$_2$S$_2$O$_5$ (0.31 g, 1.6 mmol). The reaction mixture was heated to 90° C. for 6 h. The mixture was cooled to rt, filtered, and rinsed with DMF (5 mL). This resultant solution was used immediately in the next step.

C. 2-[3-(3-Dimethylamino-propoxy)-phenyl]-1H-benzoimidazole-5-carboxylic acid amide. To a solution of 2-[3-(3-dimethylamino-propoxy)-phenyl]-1H-benzoimidazole-5-carboxylic acid (1.2 mmol) in DMF (8 mL) was added CDI (0.5 g, 3.1 mmol). After 30 min, (NH$_4$)$_2$CO$_3$ (0:6 g, 6.2 mmol) was added and the solution was stirred for an additional 16 h. The slurry was filtered, and the filtrate was concentrated. The residue was purified by reverse phase HPLC (C18; H$_2$O/CH$_3$CN/0.01% TFA) to give 56 mg (13%) of the title product. HPLC (Method B): R$_f$=5.50. MS (ESI+): mass calcd. for $C_{19}H_{22}N_4O_2$, 338.17; m/z found, 339.2 [M+H]$^+$. $^1$H NMR (500 MHz, CD$_3$OD): 8.19 (s, 1H), 7.90 (d, J=8.5 Hz, 1H), 7.71-7.70 (m, 1H), 7.69-7.67 (m, 1H), 7.65-7.62 (m, 1H), 7.51-7.48 (m, 1H), 7.19-7.17 (m, 1H), 4.17 (t, J=5.8 Hz, 2H), 3.30 (m, 2H), 2.88 (s, 6H), 2.23-2.19 (m, 2H).

Example 7

2-[4-(3-Dimethylamino-propoxy)-phenyl]-1H-benzoimidazole-5-carboxylic acid amide

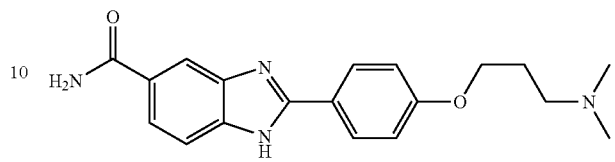

This compound was prepared using the methods outlined in Example 6, substituting 4-hydroxybenzaldehyde for 3-hydroxybenzaldehyde. HPLC (Method A): R$_f$=0.20. MS (ESI+): mass calcd. for $C_{19}H_{22}N_4O_2$, 338.17; m/z found, 339.1 [M+H]$^+$. $^1$H NMR (500 MHz, CD$_3$OD): 8.28 is, 1H), 8.08 (d, J=8.6 Hz, 1H), 8.01 (d, J=6.9 Hz, 2H), 7.70(d, J=8.6 Hz, 1H), 7.15 (d, J=7.0 Hz, 2H), 4.15 (t, J=5.7 Hz, 2H), 3.31-3.27 (m, 2H), 2.86 (s, 6H), 2.22-2.17 (m, 2H).

Example 8

2-[4-(3-Piperidin-1-yl-propoxy)-phenyl]-1H-benzoimidazole-5-carboxylic acid amide

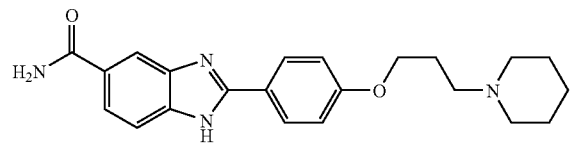

This compound was prepared using the methods outlined in Example 6, substituting 1-piperidinepropanol for 3-dimethylamino-1-propanol and 4-hydroxybenzaldehyde for 3-hydroxybenzaldehyde. HPLC (Method B): R$_f$=5.66. MS (ESI+): mass calcd. for $C_{22}H_{26}N_4O_2$, 378.21; m/z found, 379.2 [M+H]$^+$. $^1$H NMR (400 MHz, CD$_3$OD): 8.17 (s, 1H), 8.03 (d, J=9.1 Hz, 2H), 7.94 (d, J=8.6 Hz, 2H), 7.70 (d, J=8.6 Hz, 1H), 7.16 (d, J=9.1 Hz, 2H), 4.16 (t, J=5.6 Hz, 2H), 3.54-3.51 (br d, 2H), 3.26-3.23 (m, 2H), 2.92-2.85 (m, 2H), 2.24-2.17 (m, 2H), 1.93-1.87 (m, 2H), 1.79-1.64 (m, 3H), 1.50-1.40 (m, 1H).

Example 9

2-[4-(2-Piperidin-1-yl-ethoxy)-phenyl]-1H-benzoimidazole-5-carboxylic acid amide

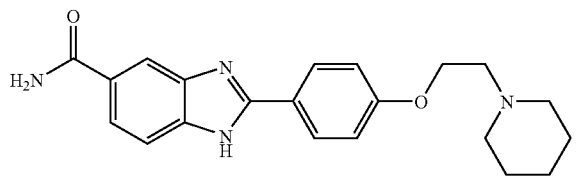

This compound was prepared using the methods outlined in Example 6, substituting 1-piperidineethanol for 3-dimethylamino-1-propanol and 4-hydroxybenzaldehyde for 3-hydroxybenzaldehyde. HPLC (Method B): $R_t$=5.54. MS (ESI+): mass calcd. for $C_{21}H_{24}N_4O_2$, 364.19; m/z found, 365.2 [M+H]+. $^1$H NMR (400 MHz, $CD_3OD$): 8.27 (s, 1H), 8.16 (d, J=8.8 Hz, 2H), 8.01 (d, J=10.7 Hz, 1H), 7.78 (d, J=10.7 Hz, 1H), 7.32 (d, J=8.8 Hz, 2H), 4.54-4.51 (m, 2H), 3.68-3.60 (m, 4H), 3.14-3.08 (m, 2H), 2.00-1.96 (m, 2H), 1.85-1.80 (m, 3H), 1.56-1.48 (m, 1H).

Example 10

2-[4-(1-Methyl-piperidin-4-yloxy)-phenyl]-1H-benzoimidazole-5-carboxylic acid amide

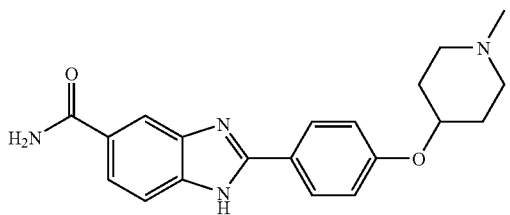

This compound was prepared using the methods outlined in Example 6, substituting 4-hydroxy-1-methylpiperidine for 3-dimethylamino-1-propanol and 4-hydroxybenzaldehyde for 3-hydroxybenzaldehyde. HPLC (Method B): $R_t$=5.43. MS (ESI+): mass calcd. for $C_{20}H_{22}N_4O_2$, 350.17; m/z found, 351.2 [M+H]+. $^1$H NMR (500 MHz, $CD_3OD$): 8.17 (s, 1H), 8.05-8.01 μm, 2H), 7.95 (d, J=8.6 Hz, 1H), 7.70 (d, J=8.6 Hz, 1H), 7.69-7.20 (m, 2H), 3.57-3.54 (m, 1H), 3.37-3.35 (m, 1H), 3.28-3.23 (m, 2H), 3.13-3.10 (m, 1H), 2.84 (s, 3H), 2.40-2.37 (m, 1H), 2.20-2.17 (m, 1H), 2.12-2.05 (m, 1H), 1.95-1.85 (m, 1H).

Example 11

2-[4-(1-Benzyl-piperidin-4-yloxy)-phenyl]-1H-benzoimidazole-5-carboxylic acid amide

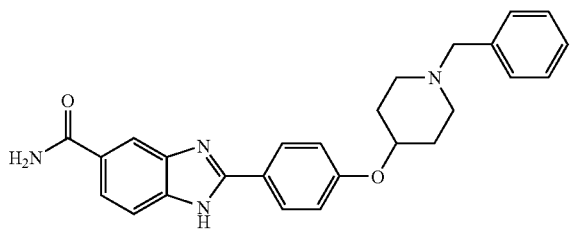

This compound was prepared using the methods outlined in Example 6, substituting 1-benzyl-4-hydroxypiperidine for 3-dimethylamino-1-propanol and 4-hydroxybenzaldehyde for 3-hydroxybenzaldehyde. HPLC (Method C): $R_t$=4.19. MS (ESI+): mass calcd. for $C_{26}H_{26}N_4O_2$, 426.21; m/z found, 427.2 [M+H]+. $^1$H NMR (400 MHz, $CD_3OD$): 8.05 (br s, 1H), 7.93 (d, J=8.8 Hz, 2H), 7.69 (d, J=8.3 Hz, 1H), 7.51-7.50 (m, 1H), 7.28-7.18 (m, 5H), 7.00 (d, J=9.0 Hz, 2H), 4.48-4.45 (m, 1H), 3.55 (br s, 2H), 2.79-2.70 (m, 2H), 2.43-2.36 (m, 2H), 2.00-1.94 (m, 2H), 1.80-1.70 (m, 2H).

Example 12

2-[4-(1-Benzyl-piperidin-3-yloxy)-phenyl]-1H-benzoimidazole-5-carboxylic acid amide

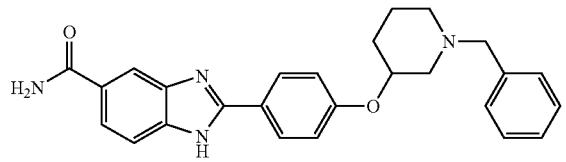

This compound was prepared using the methods outlined in Example 6, substituting 1-benzyl-3-hydroxypiperidine for 3-dimethylamino-1-propanol and 4-hydroxybenzaldehyde for 3-hydroxybenzaldehyde. HPLC (Method C): $R_t$=4.18. MS (ESI+): mass calcd. for $C_{26}H_{26}N_4O_2$, 426.21; m/z found, 427.3 [M+H]+. $^1$H NMR (500 MHz, $CD_3OD$): 8.27 (s, 1H), 8.15-8.12 (m, 2H), 8.05 (d, J=8.6 Hz, 1H), 7.58 (d, J=8.6 Hz, 1H), 7.61-7.55 (m, 2H), 7.31-7.29 (m, 3H), 7.31 (d, J=8.3 Hz, 1H), 7.25-7.24 (m, 1H), 4.75-4.71 (m, 1H), 4.50-4.45 (m, 1H), 4.37 (br s, 1H), 4.19 (br s, 1H), 3.69-3.53 (m, 1H), 3.59-3.56 (m, 1H), 2.52-2.43 (m, 1H), 2.27-2.05 (m, 3H), 1.95-1.87 (m, 1H).

Example 13

2-[4-(1-Methyl-pyrrolidin-3-yloxy)-phenyl]-1H-benzoimidazole-5-carboxylic acid amide

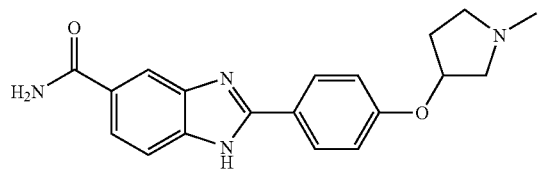

This compound was prepared using the methods outlined in Example 6, substituting 1-methyl-pyrrolidin-3-ol for 3-dimethylamino-1-propanol and 4-hydroxybenzaldehyde for 3-hydroxybenzaldehyde. HPLC (Method A): $R_t$=0.19. MS (ESI+): mass calcd. for $C_{19}H_{20}N_4O_2$, 336.16; m/z found, 337.1 [M+H]+. $^1$H NMR (500 MHz, $CD_3OD$): 8.17 (s, 1H), 8.17-8.04 (m, 2H), 7.93 (dd, J=1.6, 8.6 Hz, 1H), 7.70 (d, J=8.6 Hz, 1H), 7.18 (d, J=8.8 Hz, 2H), 5.29-5.23 (m, 1H), 3.94-3.63 (m, 2H), 3.50-3.13 (m, 2H), 2.89 (s, 3H), 2.75-2.56 (m, 1H), 2.38-2.13 (m, 1H).

Example 14

2-[4-(1-Benzyl-pyrrolidin-3-yloxy)-phenyl]-1H-benzoimidazole-5-carboxylic acid amide

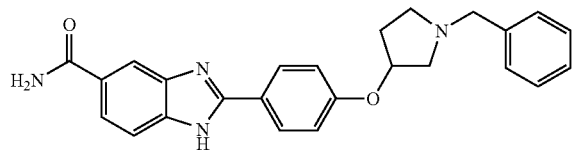

This compound was prepared using the methods outlined in Example 6, substituting 1-benzyl-pyrrolidin-3-ol for 3-dimethylamino-1-propanol and 4-hydroxybenzaldehyde for 3-hydroxybenzaldehyde. HPLC (Method C): $R_t$=4.60. MS (ESI+): mass calcd. for $C_{25}H_{24}N_4O_2$, 412.19; m/z found, 413.1 [M+H]+. 1H NMR (500 MHz, CD3OD): 8.17 (d, J=0.8 Hz, 1H), 8.05 (d, J=8.8 Hz, 2H), 7.91 (d, J=8.6 Hz, 1H), 7.70 (d, J=8.7 Hz, 1H), 7.46-7.45 (m, 2H), 7.40-7.39 (m, 3H), 7.16 (d, J=8.6 Hz, 2H), 5.28 (br s, 1H), 4.41 (s, 2H), 3.75-3.31 (m, 4H), 2.76-2.37 (m, 1H), 2.36-2.18 (m, 1H).

Example 15

2-{2-[4-(5-Carbamoyl-1H-benzoimidazol-2-yl)-phenoxy]-ethyl}-piperidine-1-carboxylic acid tert-butyl ester

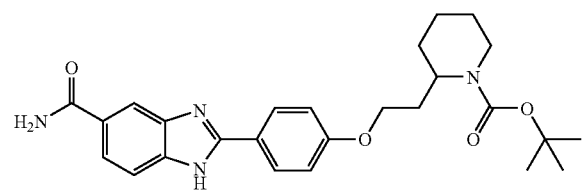

A. 2-(2-Hydroxy-ethyl)-piperidine-1-carboxylic acid tert-butyl ester. To an ice-cold solution of 2-piperidineethanol (3.0 g, 23 mmol) in CH2Cl2 (20 mL) was slowly added a solution of di-tert-butyl-dicarbonate (5.3 mL, 23 mmol) in CH2Cl2 (25 mL). After stirring at rt for 16 h, the solution was washed with 1 N NaOH (1×), H2O (2×) and brine (1×). Drying over Na2SO4 and concentration gave the crude product as a pale yellow oil that was used without further purification. 1H NMR (400 MHz, CD3OD): 4.32-4.29 (m, 1H), 3.93-3.88 (m, 1H), 3.49-3.46 (m, 2H), 2.83-2.75 (m, 1H), 1.98-1.92 (m, 1H), 1.65-1.56 (m, 5H), 1.42 (s, 9H), 1.35-1.30 (m, 1H).

B. 2-{2-[4-(5-Carbamoyl-1H-benzoimidazol-2-yl)-phenoxy]-ethyl}-piperidine-1-carboxylic acid tert-butyl ester. This compound was prepared according to the methods described in Example 6, substituting 2-(2-hydroxy-ethyl)-piperidine-1-carboxylic acid tert-butyl ester for dimethylaminopropanol and 4-hydroxybenzaldehyde for 3-hydroxybenzaldehyde. HPLC (Method C): R$_t$=5.54. MS (ESI+): mass calcd. for C26H32N4O4, 464.24; m/z found, 465.2 [M+H]+. 1H NMR (500 MHz, CD3OD): 8.04 (br s, 1H), 7.94 (d, J=8.8 Hz, 2H), 7.69 (d, J=8.2 Hz, 1H), 7.51 (br s, 1H), 6.98 (d, J=8.9 Hz, 2H), 4.46-4.44 (m, 1H), 3.97-3.93 (m, 2H), 3.90-3.88 (m, 1H), 2.90-2.75 (m, 1H), 2.23-2.18 (m, 1H), 1.85-1.72 (m, 1H), 1.57-1.53 (m, 5H), 1.32-1.05 (m, 10H).

Example 16

4-{2-[4-(5-Carbamoyl-1H-benzoimidazol-2-yl)-phenoxy]-ethyl}-piperidine-1-carboxylic acid tert-butyl ester.

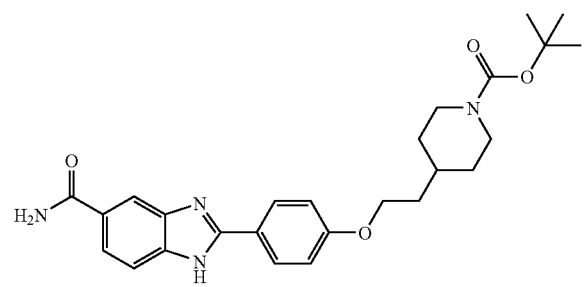

This compound was prepared using the methods outlined in Example 15, substituting 4-piperidineethanol for 2-piperidineethanol. HPLC (Method C): R$_t$=5.61. MS (ESI+): mass calcd. for C26H32N4O4, 464.24; m/z found, 465.2 [M+H]+. 1H NMR (500 MHz, CD3OD): 8.06 (br s, 1H), 7.94 (d, J=8.8 Hz, 2H), 7.69 (d, J=8.2 Hz, 1H), 7.52 (br s, 1H), 6.98 (d, J=9.0 Hz, 2H), 4.02 (t, J=5.9 Hz, 2H), 4.00-3.95 (m, 2H), 2.67 (br s, 2H), 1.68-1.62 (m, 5H), 1.35 (s, 9H), 1.12-1.02 (m, 2H).

Example 17

3-[4-(5-Carbamoyl-1H-benzoimidazol-2-yl)-phenoxy]-piperidine-1-carboxylic acid tert-butyl ester.

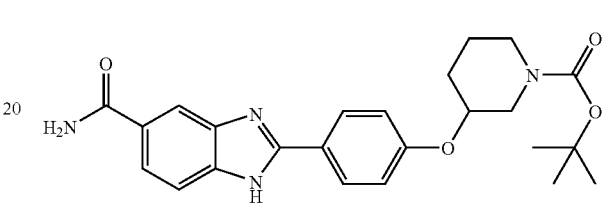

This compound was prepared using the methods outlined in Example 15, substituting 3-hydroxypiperidine for 3-dimethylamino-1-propanol. HPLC (Method C): R$_t$=5.20. MS (ESI+): mass calcd. for C24H28N4O4, 436,21; m/z found, 437.4 [M+H]+. 1H NMR (500 MHz, CD3OD): 8.19(s, 1H), 8.03-8.02 (m, 2H), 7.97 (d, J=8.6 Hz, 1H), 7.72 (d, J=8.6 Hz, 1H), 7.18 (d, J=8.9 Hz, 2H), 4.53 (br s, 1H), 3.85 (br s, 1H), 3.64 (br s, 1H), 3.46-3.35 (m, 2H), 3.17-3.07 (m, 1H), 2.00-1.80 (m, 3H), 1.50-1.47 (m, 1H), 1.37 (m, 3H), 1.18 (br s, 5H).

Example 18

4-[4-(5-Carbamoyl-1H-benzoimidazol-2-yl)-phenoxy]-piperidine-1-carboxylic acid tert-butyl ester.

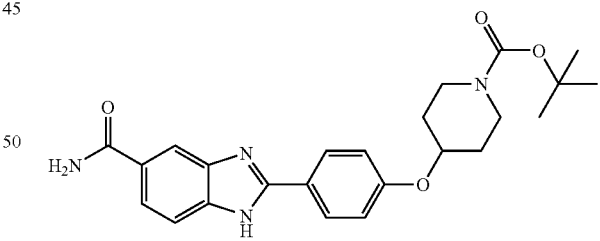

This compound was prepared using the methods outlined in Example 15, substituting 4-hydroxy-piperidine-1-carboxylic acid tert-butyl ester for 3-dimethylamimo-1-propanol and 4-hydroxybenzaldehyde for 3-hydroxybenzaldehyde. HPLC (Method C): R$_t$=5.29. MS (ESI+): mass calcd. for C24H28N4O4, 436.52; m/z found, 437.5 [M+H]+. 1H NMR (500 MHz, DMSO-d6): 8.14-8.10 (m, 3H), 7.98 (s, 1H), 7.77 (dd, J=1.5, 8.4 Hz, 1H), 7.58 (d, J=8.4 Hz, 1H), 7.27 (s, 1H), 7.21-7.16 (m, 2H), 4.72-4.68 (m, 1H), 3.72-3.68 (m, 2H), 3.36-3.21 (m, 2H), 1.98-1.95 (m, 2H), 1.58-1.55 (m, 2H), 1.42 (s, 9H).

Example 19

4-[4-(5-Carbamoyl-1H-benzoimidazol-2-yl)-phenoxymethyl]-piperidine-1-carboxylic acid tert-butyl ester

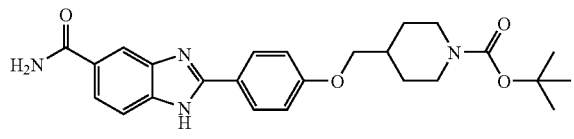

This compound was prepared using the methods outlined in Example 15, substituting 4-hydroxymethyl-piperidine-1-Carboxylic acid tert-butyl ester for 3-dimethylamino-1-propanol and 4-hydroxybenzaldehyde for 3-hydroxybenzaldehyde. HPLC (Method C): $R_t$=6.59. MS (ESI+): mass calcd. for $C_{25}H_{30}N_4O_4$, 450.54; m/z found, 451.2 [M+H]$^+$. $^1$H NMR (500 MHz, CD$_3$OD): 8.18 (d, J=1.2 Hz, 1H), 8.06 (d, J=8.8 Hz, 2H), 7.86 (dd, J=1.6, 8.5 Hz, 1H), 7.66 (d, J=8.5 Hz, 1H), 7.13 (d, J=8.9, 2H), 4.16 (d, J=13.2 Hz, 2H), 3.96 (d, J=6.3 Hz, 2H), 2.93-2.75 (m, 2H), 2.05-2.03 (m, 1H), 1.87 (d, J=11.7 Hz, 2H), 1.47 (m, 9H), 1.35-1.28 (m, 2H).

Example 20

3-[4-(5-Carbamoyl-1H-benzoimidazol-2-yl)-phenoxymethyl]-piperidine-1-carboxylic acid tert-butyl ester

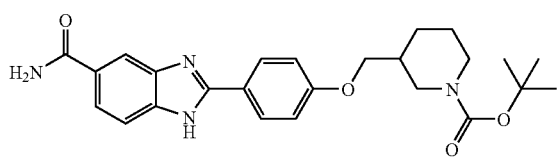

This compound was prepared using the methods outlined in Example 15, substituting 3-hydroxymethyl-piperidine-1-carboxylic acid tertbutyl ester for 3-dimethylamino-1-propanol and 4-hydroxybenzaldehyde for 3-hydroxybenzaldehyde. HPLC (Method C): $R_t$=5.61. MS (ESI+): mass calcd. for $C_{25}H_{30}N_4O_4$, 450.54; m/z found, 451.1 [M+H]$^+$. $^1$H NMR (500 MHz, CD$_3$OD): 8.15 (s, 1H), 8.06 (d, J=8.8 Hz, 2H), 7.80 (dd, J=1.5, 8.5 Hz, 1H), 7.62-7.61 (m, 1H), 7.11 (d, J=9.1 Hz, 2H), 4.17-3.76 (m, 1H), 4.00-3.92 (m, 3H), 3.12-2.81 (m, 2H), 2.07-1.98 (m, 1H), 1.96-1.89 (m, 1H), 1.77-1.69 (m, 1H), 1.56-1.31 (m, 2H), 1.43 (s, 9H).

Example 21

2-[4-(2-Piperidin-2-yl-ethoxy)-phenyl]-1H-benzoimidazole-5-carboxylic acid amide

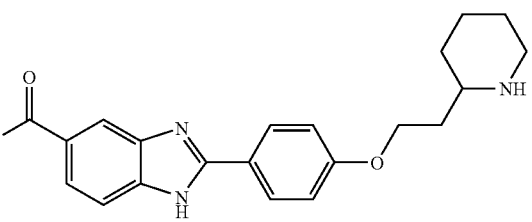

To an ice-cold solution of 2-{2-[4-(5-carbamoyl-1H-benzoimidazol-2-yl)-phenoxy]-ethyl}-piperidine-1-carboxylic acid tert-butyl ester (0.65 g, 1.4 mmol) in CH$_2$Cl$_2$ (15 mL) was slowly added TFA (3.8 mL). The solution was stirred and gradually warmed to rt over 2 h. All solvent was removed via toluene azeotrope to provide the 0.68 g (100%) of the product as a yellow solid. HPLC (Method C): $R_t$=3.87. MS (ESI+): mass calcd. for $C_{21}H_{24}N_4O_2$, 364.19; m/z found, 365.1 [M+H]$^+$. $^1$H NMR (400 MHz, CD$_3$OD): 6.20 (s, 1H), 8.05 (d, J=8.7 Hz, 2H), 7.79 (d, J=10.7 Hz, 1H), 7.73 (d, J=10.7 Hz, 1H), 7.20 (d, J=8.7 Hz, 2H), 4.23-4.19 (m, 2H), 3.31-3.28 (m, 2H), 3:03-2.89 (m, 1H), 2.17-2.11 (m, 1H), 2.10-1.98 (m, 2H), 1.83-1.76 (m, 2H), 1.64-1.44 (m, 3H).

Example 22

2-[4-(2-Piperidin-4-yl-ethoxy)-phenyl]-1H-benzoimidazole-5-carboxylic acid amide

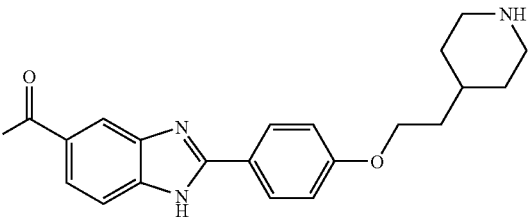

This compound was prepared using the methods outlined in Example 21, substituting 4-{2-[4-(5-carbamoyl-1H-benzoimidazol-2-yl)-phenoxy]-ethyl}-piperidine-1-carboxylic acid tert-butyl ester for 2-{2-[4-(5-carbamoyl-1H-benzoimidazol-2-yl)-phenoxy]-ethyl}-piperidine-1-carboxylic acid tert-butyl ester. HPLC (Method C): $R_t$=3.94. MS (ESI+): mass calcd. for $C_{21}H_{24}N_4O_2$, 364.19; m/z found, 365.1 [M+H]$^+$. $^1$H-NMR (400 MHz, CD$_3$OD): 8.19 (s, 1H), 8.02 (d, J=8.9 Hz, 2H), 7.95 (d, J=8.6 Hz, 1H), 7.70 (d, J=8.6 Hz, 1H), 7.16 (d, J=8.9 Hz, 2H), 4.15-4.11 (m, 2H), 3.32-3.24 (m, 2H), 2.95-2.88 (m, 2H), 1.97-1.93 (m, 2H), 1.90-1.81 (m, 1H), 1.81-1.75 (m, 2H), 1.45-1.36 (m, 2H).

Example 23

2-[4-(Piperidin-3-yloxy)-phenyl]-1H-benzoimidazole-5-carboxylic acid amide

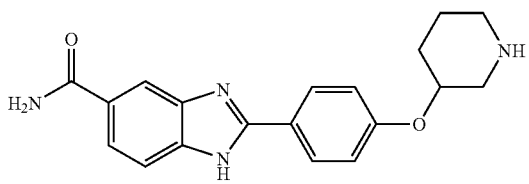

This compound was prepared using the methods outlined in Example 21, substituting 3-[4-(5-carbamoyl-1H-benzoimidazol-2-yl)-phenoxy]-piperidine-1-carboxylic acid tert-butyl ester for 2-{2-[4-(5-carbamoyl-1H-benzoimidazol-2-yl)-phenoxy]-ethyl}-piperidine-1-carboxylic acid tert-butyl ester. HPLC (Method C): $R_f$=3.68. MS (ESI+): mass calcd. for $C_{19}H_{20}N_4O_2$, 336.16; m/z found, 337.3 [M+H]$^+$. $^1$H NMR (400 MHz, CD$_3$OD): 8.11 (s, 1H), 7.96 (d, J=8.8 Hz, 2H), 7.75 (d, J=8.5 Hz, 1H), 7.54 (d, J=8.5 Hz, 1H), 7.03 (d, J=8.9 Hz, 2H), 4.39-4.35 (m, 1H), 3.10-3.06 (m, 1H), 2.78-2.67 (m, 3H), 2.08-1.96 (m, 1H), 1.83-1.74 (m, 1H), 1.72-1.65 (m, 1H), 1.55-1.46 (m, 1H).

Example 24

2-[4-(Piperidin-4-yloxy)-phenyl]-1H-benzoimidazole-5-carboxylic acid amide

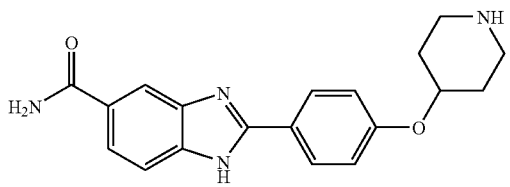

This compound was prepared using the methods outlined in Examples 6 and 21, substituting 4-hydroxy-piperidine-1-arboxylic acid tert-butyl ester for 3-dimethylamino-1-propanol and 4-hydroxybenzaldehyde for 3-hydroxybenzaldehyde. HPLC (Method C): $R_f$=3.69. MS (ESI+): mass calcd. for $C_{19}H_{20}N_4O_2$, 336.40; m/z found, 337.4 [M+H]$^+$. $^1$H NMR (400 MHz, CD$_3$OD): 8.30 (s, 1H), 8.17-8.14 (m, 2H), 8.09 (dd, J=1.5, 8.6 Hz, 1H), 7.84 (d, J=8.6 Hz, 1H), 7.36 (d, J=9.0 Hz, 2H), 4.96-4.93 (m, 1H), 3.47-3.33 (m, 2H), 3.32-3.24 (m, 2H), 2.26-2.23 (m, 2H), 2.11-2.08 (m, 2H).

Example 25

2-[4-(Piperidin-4-ylmethoxy)-phenyl]-1H-benzoimidazole-5-carboxylic acid amide

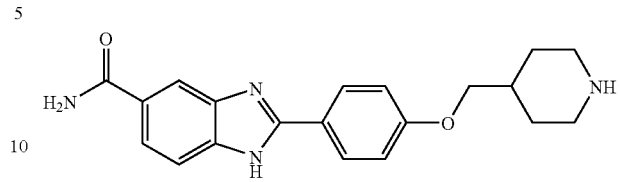

This compound was prepared using the methods outlined in Examples 6 and 21, substituting 4-hydroxymethyl-piperidine-1-carboxylic acid tert-butyl ester for 3-dimethylamino-1-propanol and 4-hydroxybenzaldehyde for 3-hydroxybenzaldehyde. HPLC (Method C): $R_f$=4.15. MS (ESI+): mass calcd. for $C_{20}H_{22}N_4O_2$, 350.42; m/z found, 351.2 [M+H]$^+$. $^1$H NMR (400 MHz, CD$_3$OD): 8.20 (s, 1H), 8.05-7.98 (m, 3H), 7.74 (d, J=8.6 Hz, 1H), 7.19 (d, J=8.9 Hz, 2H), 3.98 (d, J=6.0 Hz, 2H), 3.38 (d, J=12.7 Hz, 2H), 2.98 (t, J=12.7 Hz, 2H), 2.20-2.04 (m, 1H), 2.02 (d, J=14.6 Hz, 2H), 1.58-1.55 (m, 2H).

Example 26

2-[4-(Piperidin-3-ylmethoxy)-phenyl]-1H-benzoimidazole-5-carboxylic acid amide

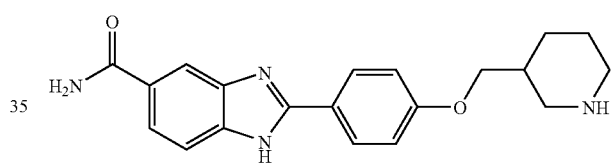

This compound was prepared using the methods outlined in Examples 6 and 21, substituting 3-hydroxymethyl-piperidine-1-carboxylic acid tert-butyl ester for 3-dimethylamino-1-propanol and 4-hydroxybenzaldehyde for 3-hydroxybenzaldehyde. HPLC (Method C): $R_f$=3.82. MS (ESI+): mass calcd. for $C_{20}H_{22}N_4O_2$, 350.42; m/z found, 351.1 [M+H]$^+$. $^1$H NMR (500 MHz, CD$_3$OD): 8.30 (s, 1H), 8.14 (d, J=8.8 Hz, 2H), 8.09 (dd, J=1.1, 8.5 Hz, 1H), 7.83 (d, J=8.6 Hz, 1H), 7.29 (dd, J=2.8, 11.7 Hz, 2H), 4.19-4.16 (m, 1H), 4.09-4.05 (m, 1H), 3.60-3.56 (m, 1H), 3.41 (d, J=10.0 Hz, 1H), 3.01-2.92 (m, 2H), 2.40-2.31 (m, 1H), 2.03 (d, J=10.0 Hz, 2H), 1.87-1.78 (m, 1H), 1.58-1.51 (m, 1H).

Example 27

2-(4-{2-[1-(4-Methyl-benzyl)-piperidin-2-yl]-ethoxy}-phenyl)-1H-benzoimidazole-5-carboxylic acid amide

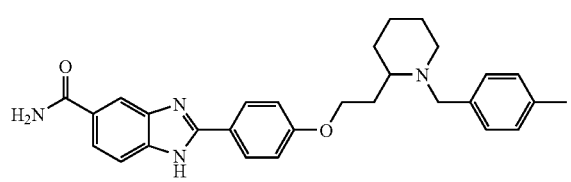

To a solution of 2-[4-(2-piperidin-2-yl-ethoxy)-phenyl]-1H-benzoimidazole-5-carboxylic acid amide (0.10 g, 0.27 mmol) in DMF (1 mL) was added p-tolualdehyde (70 μL, 0.59 mmol), activated 4 Å molecular sieves, and NaB(OAc)$_3$H (0.175 g, 0.82 mmol). The solution was stirred for 16 h and additional portions of aldehyde (1 equiv.) and NaB(OAc)$_3$H (3 equiv.) were added. When HPLC monitoring indicated reaction completion, the solution was quenched with 1 N NaOH and purified by reverse phase HPLC (C18; H$_2$O/CH$_3$CN/0.01% TFA), providing 60 mg (48%) of product. HPLC (Method C): R$_t$=4.60. MS (ESI+): mass calcd. for C$_{29}$H$_{32}$N$_4$O$_2$, 468.25; m/z found, 469.4 [M+H]$^+$. $^1$H NMR (500 MHz, CD$_3$OD): 8.18 (s, 1H), 8.04 (d, J=8.4 Hz, 2H), 7.94 (d, J=8.6 Hz, 1H), 7.70 (d, J=8.6 Hz, 1H), 7.34-7.32 (m, 2H), 7.23-7.20 (m, 2H), 7.15-7.13 (m, 2H), 4.33-4.10 (m, 3H), 3.45-3.39 (m, 1H), 3.15-3.07 (m, 1H), 2.90-2.85 (m, 1H), 2.72-2.67 (m, 1H), 2.42-2.37 (m, 1H), 2.20-2.10 (m, 1H), 1.93 (br s, 1H), 1.88-1.73 (m, 2H), 1.73-1.45(m, 3H).

Example 28

2-(4-{2-[1-(4-Methoxy-benzyl)-piperidin-2-yl]-ethoxy}-phenyl)-1H-benzoimidazole-5-carboxylic acid amide

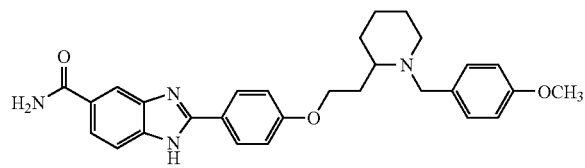

This compound was prepared using the methods outlined in Example 27, substituting p-anisaldehyde for p-tolualdehyde. HPLC (Method C): R$_t$=4.48. MS (ESI+): mass calcd. for C$_{29}$H$_{32}$N$_4$O$_3$, 484.25; m/z found, 485.4 [M+H]$^+$. $^1$H NMR (500 MHz, CD$_3$OD): 8.17 (s, 1H), 8.03 (d, J=8.6 Hz, 2H), 7.92 (d, J=8.6 Hz, 1H), 7.69 (d, J=8.6 Hz, 1H), 7.38-7.35 (m, 2H), 7.16-7.14 (m, 2H), 6.95-6.92 (m, 2H), 4.30-4.17 (m, 3H), 3.73 (s, 3H), 3.40-3.38(m, 1H), 3.12-3.09 (m, 1H), 2.90-2.87 (m, 1H), 2.71-2.68 (m, 1H), 2.39-2.27 (m, 1H), 2.18-2.14 (m, 1H), 1.95-1.92 (m, 1H), 1.84-1.78 (m, 2H), 1.68-1.50 (m, 3H).

Example 29

2-(4-{2-[1-(4-Chloro-benzyl)-piperidin-2-yl]-ethoxy}-phenyl)-1H-benzoimidazole-5-carboxylic acid amide

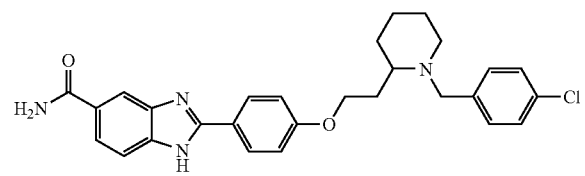

This compound was prepared using the methods outlined in Example 27, substituting p-chlorobenzaldehyde for p-tolualdehyde. HPLC (Method C): R$_t$=4.62. MS (ESI+): mass calcd. for C$_{28}$H$_{29}$ClN$_4$O$_2$, 488.20; m/z found, 489.3 [M+H]$^+$. $^1$H NMR (500 MHz, CD$_3$OD): 8.19 (s, 1H), 8.04 (d, J=8.8 Hz, 2H), 7.97 (d, J=8.6 Hz, 1H), 7.71 (d, J=8.6 Hz, 1H), 7.47-7.45 (m, 2H), 7.42-7.40 (m, 2H), 7.17-7.14 (m, 2H), 4.35-4.17 (m, 3H), 3.47-3.41 (m, 1H), 3.17-3.07 (m, 1H), 2.95-2.88 (m, 1H), 2.72-2.66 (m, 1H), 2.39-2.26 (m, 1H), 2.23-2.15 (m, 1H), 1.95-1.90 (m, 1H), 1.89-1.77 (m, 2H), 1.77-1.50 (m, 3H).

Example 30

2-(4-{2-[1-3,4-Dichloro-benzyl)-piperidin-2-yl]-ethoxy}-phenyl)-1H-benzoimidazole-5-carboxylic acid amide

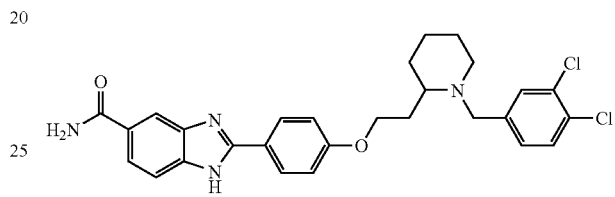

This compound was prepared using the methods outlined in Example 27, substituting 3,4-dichlorobenzaldehyde for p-tolualdehyde. HPLC (Method C): R$_t$=4.80. MS (ESI+): mass calcd. for C$_{28}$H$_{28}$Cl$_2$N$_4$O$_2$, 522.16; m/z found, 523.3 [M+H]$^+$. $^1$H NMR (500 MHz, CD$_3$OD): 8.18 (s, 1H), 8.03 (d, J=8.5 Hz, 2H), 7.94 (d, J=8.3 Hz, 1H), 7.71-7.69 (m, 2H), 7.60-7.55 (m, 1H), 7.42-7.40 (m, 1H), 7.16-7.14 (m, 2H), 4.44-4.13 (m, 3H), 3.46-3.39 (m, 1H), 3.16-3.09 (m, 1H), 3.00-2.87 (m, 1H), 2.72-2.62 (m, 1H), 2.40-2.20 m, 1H), 2.27-2.10 (m, 2H), 1.99-1.88 (m, 1H), 1.88-1.46 (m, 4H).

Example 31

2-{4-[2-(1-Benzyl-piperidin-2-yl)-ethoxy]-phenyl}-1H-benzoimidazole-5-carboxylic acid amide

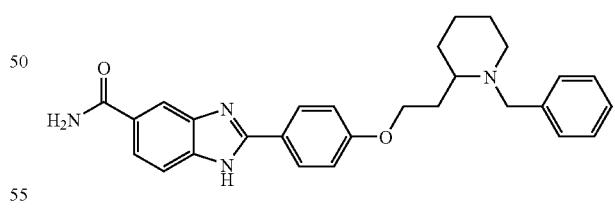

This compound was prepared using the methods outlined in Example 27, substituting benzaldehyde for p-tolualdehyde. HPLC (Method C): R$_t$=4.41. MS (ESI+): mass calcd. for C$_{28}$H$_{30}$N$_4$O$_2$, 454.24; m/z found, 455.4 [M+H]$^+$. $^1$H NMR (500 MHz, CD$_3$OD): 8.17 (s, 1H), 8.03 (d, J=8.4 Hz, 2H), 7.92 (d, J=8.5 Hz, 1H), 7.69 (d, J=8.5 Hz, 1H), 7.47-7.44 (m, 2H), 7.42-7.39 (m, 3H), 7.18-7.12 (m, 2H), 4.40-4.32 (m, 1H), 4.30-4.14 (m, 2H), 3.46-3.42 (m, 1H), 3.16-3.08 (m, 1H), 2.92-2.86 (m, 1H), 2.76-2.68 (m, 1H), 2.43-2.25 (m, 1H), 2.20-2.15 (m, 1H), 1.98-1.90 (m, 1H), 1.87-1.76 (m, 2H), 1.70-1.47 (m, 3H).

Example 32

2-{4-[2-(1-Benzyl-piperidin-4-yl)-ethoxy]-phenyl}-1H-benzoimidazole-5-carboxylic acid amide

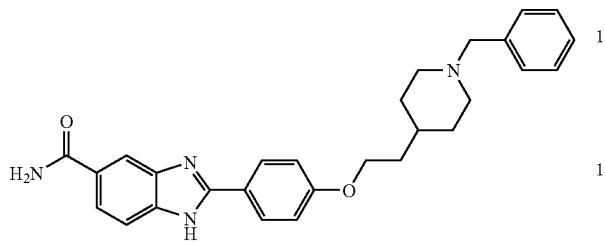

This compound was prepared using the methods outlined in Example 27, substituting benzaldehyde for p-tolualdehyde and 2-[4-(2-piperidin-4-yl-ethoxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): $R_f$=4.41. MS (ESI+): mass calcd. for $C_{28}H_{30}N_4O_2$, 454.24; m/z found, 455.4 [M+H]$^+$. $^1$H NMR (500 MHz, CD$_3$OD): 8.15 (s, 1H), 8.00 (d, J=8.9 Hz, 2H), 7.91 (d, J=8.5 Hz, 1H), 7.67 (d, J=8.7 Hz, 1H), 7.40 (br m, 5H), 7.12 (d, J=8.8 Hz, 2H), 4.21 (s, 2H), 4.11 (t, J=6.1 Hz, 2H), 3.43-3.40 (m, 2H), 2.95-2.89 (m, 2H), 2.00-1.97 (m, 2H), 1.87-1.78 (m, 1H), 1.78-1.72 (m, 2H), 1.48-1.37 (m, 2H).

Example 33

2-(4-{2-[1-(4-Methyl-benzyl)-piperidin-4-yl]-ethoxy}-phenyl)-1H-benzoimidazole-5-carboxylic acid amide

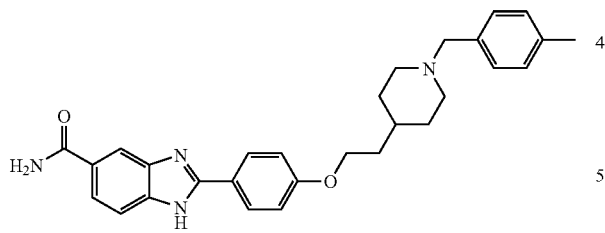

This compound was prepared using the methods outlined in Example 27, substituting 2-[4-(2-piperidin-4-yl-ethoxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): $R_f$=4.63. MS (ESI+): mass calcd. 4 or $C_{29}H_{32}N_4O_2$, 468.25; m/z found, 469.4 [M+H]$^+$. $^1$H NMR (500 MHz, CD$_3$OD): 8.16 (s, 1H), 8.00 d, J=8.9 Hz, 2H), 7.91 (d, J=9.0 Hz, 1H), 7.68 (d, J=8.9 Hz, 1H), 7.27 (d, J=8.1 Hz, 2H), 7.20 (d, J=7.9 Hz, 2H), 7.12 (d, J=8.9 Hz, 2H), 4.15 (s, 2H), 4.10 (t, J=6.1 Hz, 2H), 3.41-3.37 (m, 2H), 2.92-2.89 (m, 2H), 2.29 (s, 3H), 1.99-1.96 (m, 2H), 1.85-1.78 (m, 1H), 1.78-1.71 (m, 2H), 1.48-1.36(m, 2H).

Example 34

2-(4-{2-[1-(4-Methoxy-benzyl)-piperidin-4-yl]-ethoxy}-phenyl)-1H-benzoimidazole-5-carboxylic acid amide

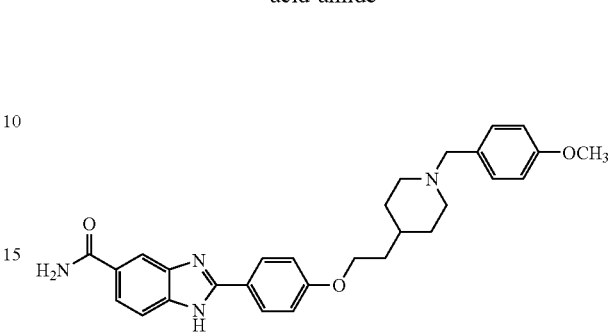

This compound was prepared using the methods outlined in Example 27, substituting p-anisaldehyde for p-tolualdehyde and 2-[4-(2-piperidin-4-yl-ethoxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): $R_f$=4.49. MS (ESI+): mass calcd. for $C_{29}H_{32}N_4O_3$, 484.25; m/z found, 485.4 [M+H]$^+$. $^1$H NMR (500 MHz, CD$_3$OD): 8.17 (s, 1H), 8.00 (d, J=8.8 Hz, 2H), 7.93 (d, J=8.5 Hz, 1H), 7.69 (d, J=8.5 Hz, 1H), 7.31 (d, J=8.7 Hz, 2H), 7.13 (d, J=8.8 Hz, 2H), 6.92 (d, J=8.7 Hz, 2H), 4.13 (s, 2H), 4.13-4.11 (m, 2H), 3.73 (s, 3H), 3.41-3.38 (m, 2H), 2.94-2.85 (m, 2H), 1.99-1.96 (m, 2H), 1.86-1.79 (m, 1H), 1.79-1.71 (m, 2H), 1.47-1.36 (m, 2H).

Example 35

2-(4-{2-[1-(4-Chloro-benzyl)-piperidin-4-yl]-ethoxy}-phenyl)-1H-benzoimidazole-5-carboxylic acid amide

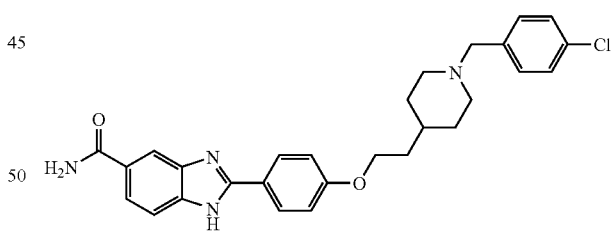

This compound-was prepared using the methods outlined in Example 27, substituting p-chlorobenzaldehyde for p-tolualdehyde and 2-[4-(2-piperidin-4-yl-ethoxy)phenyl]-1H-benzoimidazole-5-carboxylic acid amide for 2-[4-(2piperidin-2-yl-ethoxy)-phenyl]-1H-benzoimidazole-5-carboxylic acid amide. HPLC (Method C): $R_f$=4.65. MS (ESI+): mass calcd. for $C_{28}H_{29}ClN_4O_2$, 488.20; m/z found, 489.4 [M+H]$^+$. $^1$H NMR (500 MHz, CD$_3$OD): 8.17 (s, 1H), 8.01 (d, J=8.7 Hz, 2H), 7.93 (d, J=8.6 Hz, 1H), 7.69 (d, J=8.5 Hz, 1H), 7.41 (app s, 4H), 7.13 (d, J=8.5 Hz, 2H), 4.20 (s, 2H), 4.12-4.10 (m, 2H), 3.43-3.39 (m, 2H), 2.95-2.89 (m, 2H), 1.99-1.96 (m, 2H), 1.85-1.78 (m, 1H), 1.78-1.70 (m, 2H), 1.47-1.40 (m, 2H).

Example 36

2-(4-{2-[1-(3,4-Dichloro-benzyl)-piperidin-4-yl]-ethoxy}-phenyl)-1H-benzoimidazole-5-carboxylic acid amide

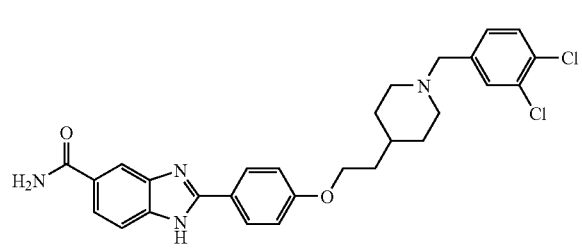

This compound was prepared using the methods outlined in Example 27, substituting 3,4-dichlorobenzaldehyde for p-tolualdehyde and 2-[4-(2-piperidin-4-yl-ethoxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): $R_f$=4.85. MS (ESI+): mass calcd. for $C_{28}H_{28}Cl_2N_4O_2$, 522.16; m/z found, 523.3 [M+H]$^+$. $^1$H NMR (500 MHz, CD$_3$OD): 8.17 (s, 1H), 8.01 (d, J=8.8 Hz, 2H), 7.93 (d, J=8.6 Hz, 1H), 7.69 (d, J=8.5 Hz, 1H), 7.64 (s, 1H), 7.56 (d, J=8.2 Hz, 1H), 7.35 (d, J=8.2 Hz, 1H), 7.13 (d, J=8.7 Hz, 2H), 4.21 (s, 2H), 4.12-4.10 (m, 2H), 3.42-3.40 (m, 2H), 2.98-2.89 (m, 2H), 2.00-1.97 (m, 2H), 1.87-1.78 (m, 1H), 1.78-1.70 (m, 2H), 1.47-1.43 (m, 2H).

Example 37

2-{4-[1-(4-Chloro-benzyl)-piperidin-3-yloxy]-phenyl}-1H-benzoimidazole-5-carboxylic acid amide

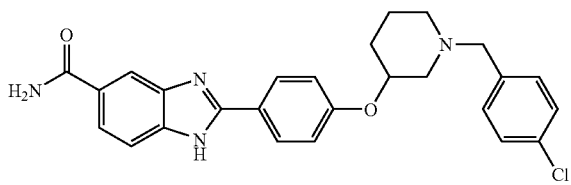

This compound was prepared using the methods outlined in Example 27, substituting p-chlorobenzaldehyde for p-tolualdehyde and 2-[4-(piperidin-3-yloxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): $R_f$=4.44. MS (ESI+): mass calcd. for $C_{26}H_{25}ClN_4O_2$, 460.17; m/z found, 461.3 [M+H]$^+$. $^1$H NMR (500 MHz, CD$_3$OD): 8.18 (s, 1H), 8.03 (d, J=8.9 Hz, 2H), 7.95 (d, J=8.5 Hz, 1H), 7.71 (d, J=8.5 Hz, 1H), 7.44 (d, J=8.5 Hz, 2H), 7.39 (d, J=8.5 Hz, 2H), 7.22 (d, J=9.0 Hz, 2H), 4.40-4.22(m, 2H), 3.58-3.40 (m, 2H), 3.37-3.14 (m, 2H), 3.14-2.95 (m, 1H), 2.16-1.97 (m, 2H), 1.88-1.70 (m, 2H).

Example 38

2-[4-(1-Benzyl-piperidin-3-ylmethoxy)-phenyl]-1H-benzoimidazole-5-carboxylic acid amide

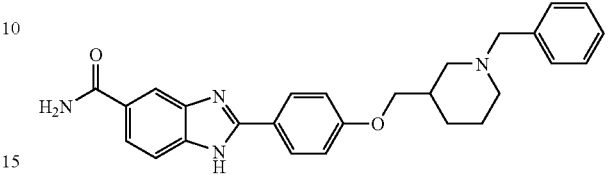

This compound was prepared using the methods outlined in Example 27, substituting 2-[4-(piperidin-3-ylmethoxy)-phenyl]-1H-benzoimidazole-5-carboxylic acid amide for 2-[4-(2-piperidin-2-yl-ethoxy)-phenyl]-1H-benzoimidazole-5-arboxylic acid amide and benzaldehyde for p-tolualdehyde. HPLC (Method C): $R_f$=4.33. MS (ESI+): mass calcd. for $C_{27}H_{28}N_4O_2$, 440.55; m/z found, 441.4 [M+H]$^+$. $^1$H NMR (500 MHz, CD$_3$OD): 8.15 Hz, 1H), 8.01 (d, J=9.1 Hz, 2H), 7.88 (dd, J=1.4, 8.8 Hz, 1H), 7.65 (d, J=8.5 Hz, 1H), 7.45-7.41 (m, 5H), 7.25-7.21 (m, 1H), 7.10 (d, J=8.8 Hz, 2H), 4.31-4.24 (m, 2H), 4.07-4.04 (m, 1H), 3.95-3.92 (m, 1H), 3.62-3.59 (m, 1H), 3.45-3.41 (m, 1H), 2.91-2.85 (m, 2H), 2.33-2.25 (m, 1H), 2.00-1.89 (m, 2H), 1.79-1.69 (m, 1H), 1.45-1.36 (m, 1H).

Example 39

2-{4-[1-(4-Methyl-benzyl)-piperidin-3-ylmethoxy]-phenyl}-1H-benzoimidazole-5-carboxylic acid amide

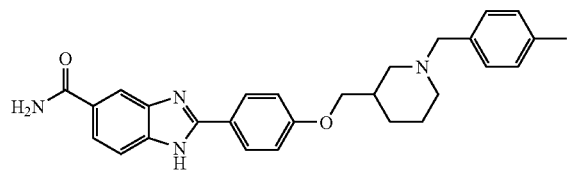

This compound was prepared using the methods outlined in Example 27, substituting 2-[4-(piperidin-3-ylmethoxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): $R_f$=4.56. MS (ESI+): mass calcd. for $C_{28}H_{30}N_4O_2$, 454.58; m/z found, 455.4 [M+H]$^+$. $^1$H NMR (500 MHz, CD$_3$OD): 8.14 (s, 1H), 8.01 (d, J=8.8 Hz, 2H), 7.89 (dd, J=1.7, 8.6 Hz, 1H), 7.64 (d, J=8.5 Hz, 1H), 7.31 (d, J=8.3 Hz, 2H), 7.23 (d, J=8.0 Hz, 2H), 7.10 (d, J=8.8 Hz, 2H), 4.23-4.22 (m, 2H), 4.07-4.04 (m, 1H), 3.95-3.91 (m, 1H), 3.61-3.57 (m, 1H), 3.44-3.40 (m, 1H), 2.89-2.83 (m, 2H), 2.33-2.23 (m, 1H), 2.30 (s, 3H), 1.99-1.89 (m, 2H), 1.79-1.68 (m, 1H), 1.44-1.36 (m, 1H).

Example 40

2-{4-[1-(4-Methoxy-benzyl)-piperidin-3-yl-methoxy]-phenyl}-1H-benzoimidazole-5-carboxylic acid amide

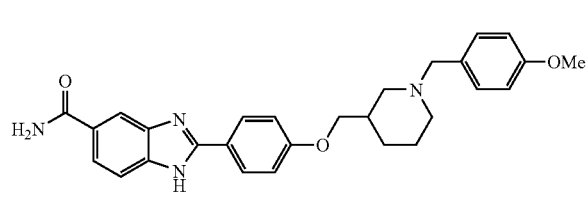

This compound was prepared using the methods outlined in Example 27, substituting 2-[4-(piperidin-3-ylmethoxy)-phenyl]-1H-benzoimidazole-5-carboxylic acid amide for 2-[4-(2-piperidin-2-yl-ethoxy)-phenyl]-1H-benzoimidazole-5-carboxylic acid amide and p-anisaldehyde for p-tolualdehyde. HPLC (Method C): $R_t$=4.42. MS (ESI+): mass calcd. for $C_{28}H_{30}N_4O_3$, 470.58; m/z found, 471.4 [M+H]$^+$. $^1$H NMR (500 MHz, CD$_3$OD): 8.14 (s, 1H), 8.01 (d, J=8.8 Hz, 2H), 7.86 (dd, J=1.5, 8.7 Hz, 1H), 7.64 (d, J=8.8 Hz, 1H), 7.34 (d, J=8.8 Hz, 2H), 7.10 (d, J=8.8 Hz, 2H), 6.95 (d, J=8.8 Hz, 2H), 4.21-4.19 (m, 2H), 4.07-4.04 (m, 1H), 3.95-3.92 (m, 1H), 3.74(s, 3H), 3.61-3.56 (m, 1H), 3.44-3.40 (m, 1H), 2.00-1.89 (m, 2H), 1.79-1.67 (m, 1H), 1.45-1.35 m, 1H).

Example 41

2-{4-[1-(4-Chloro-benzyl)-piperidin-3-ylmethoxy]-phenyl}-1H-benzoimidazole-5-carboxylic acid amide

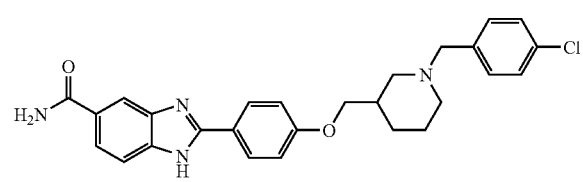

This compound was prepared using the methods outlined in Example 27, substituting 2-[4-(piperidin-3-ylmethoxy)-phenyl]-1H-benzoimidazole-5-carboxylic acid amide for 2-[4-(2-piperidin-2-yl-ethoxy)-phenyl]-1H-benzoimidazole-5-carboxylic acid amide and p-chlorobenzaldehyde for p-tolualdehyde. HPLC (Method C): $R_t$=4.57. MS (ESI+): mass calcd. for $C_{27}H_{27}ClN_4O_2$, 474.18; m/z found, 475.3 [M+H]$^+$. $^1$H NMR (500 MHz, CD$_3$OD): 8.13 (s, 1H), 8.00 (d, J=8.8 Hz, 2H), 7.85 (dd, J=1.5, 8.7 Hz, 1H), 7.63 (d, J=8.5 Hz, 1H), 7.43 (s, 4H), 7.10 (d, J=8.8 Hz, 2H), 4.28-4.27 (m, 2H), 4.08-4.04 (m, 1H), 3.95-3.91 (m, 1H), 3.62-3.57 (m, 1H), 3:45-3.40 (m, 1H), 2.91-2.85 (m, 2H), 2.32-2.24(m, 1H), 2.01-1.89 (m, 2H), 1.80-1.69 (m, 1H), 1.46-1.36 (m, 1H).

Example 42

2-{4-[1-(3,4-Dichloro-benzyl)-piperidin-3-yl-methoxy]-phenyl}-1H-benzoimidazole-5-carboxylic acid amide

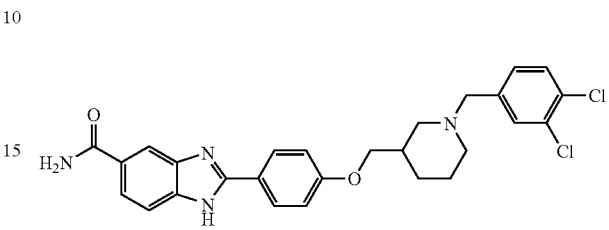

This compound was prepared using the methods outlined in Example 27, substituting 2-[4-(piperidin-3-ylmethoxy)-phenyl]-1H benzoimidazole-5-carboxylic acid amide for 2-[4-(2-piperidin-2-yl-ethoxy)-phenyl]-1H-benzoimidazole-5-carboxylic acid amide and 3,4-dichlorobenzaldehyde for p-tolualdehyde. HPLC (Method C): $R_t$=4.79. MS (ESI+): mass calcd. for $C_{27}H_{26}Cl_2N_4O_2$, 508.14; m/z found, 509.3 [M+H]$^+$. $^1$H NMR (500 MHz, CD$_3$OD): 8.17 (s, 1H), 8.02 (d, J=9.1 Hz, 2H), 7.92 (dd, J=1.5, 8.7 Hz, 1H), 7.67 (m, 2H), 7.58 (d, J=8.3 Hz, 1H), 7.28 (dd, J=2.0, 8.4 Hz, 1H), 7.13 (d, J=9.1 Hz, 2H), 4.32-4.25 (m, 2H), 4.08-4.05 (m, 1H), 3.98-3.94 (m, 1H), 3.61-3.58 (m, 1H), 3.45-3.41 (m, 1H), 2.92-2.87 (m, 2H), 2.36-2.25 (m, 1H), 2.00-1.90 (m, 2H), 1.81-1.71 (m, 1H), 1.46-1.36 (m, 1H).

Example 43

2-[4-(1-Benzyl-piperidin-4-ylmethoxy)-phenyl]-1H-benzoimidazole-5-carboxylic acid amide

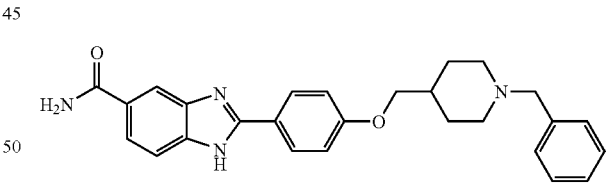

This compound was prepared using the methods outlined in Example 27, substituting 2-[4-(piperidin-4-ylmethoxy)-phenyl]-1H-benzoimidazole-5-carboxylic acid amide for 2-[4-(2-piperidin-2-yl-ethoxy)-phenyl]-1H-benzoimidazole-5-carboxylic acid amide and benzaldehyde for p-tolualdehyde. HPLC (Method C): $R_t$=4.37. MS (ESI+): mass calcd. for $C_{27}H_{28}N_4O_2$, 440.55; m/z found, 441.4 [M+H]$^+$. $^1$H NMR (500 MHz, CD$_3$OD): 8.16 (s, 1H), 8.00 (d, J=8.8 Hz, 2H), 7.91 (dd, J=1.5, 8.6 Hz, 1H), 7.67 (d, J=8.5 Hz, 1H), 7.44-7.40 (m, 5H), 7.25-7.20 (m, 1H), 7.12 (d, J=9.5 Hz, 2H), 4.24 (s, 2H), 3.95 (d, J=5.5 Hz, 2H), 3.48 (d, J=12.4 Hz, 2H), 3.00 (t, J=12.5 Hz, 1H), 2.08-2.02 (m, 3H), 1.66-1.56 (m, 2H).

Example 44

2-{4-[1-(4-Methyl-benzyl)-piperidin-4-ylmethoxy]-phenyl}-1H-benzoimidazole-5-carboxylic acid amide

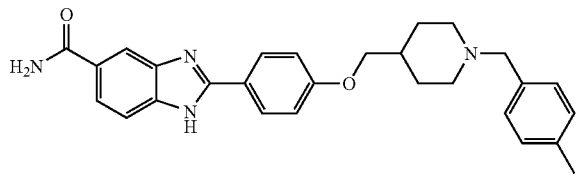

This compound was prepared using the methods outlined in Example 27, substituting 2-[4-(piperidin-4-ylmethoxy)-phenyl]-1H-benzoimidazole-5-carboxylic acid amide for 2-[4-(piperidin-2-yl-ethoxy)-phenyl]-1H-benzoimidazole-5-carboxylic acid amide. HPLC (Method C): $R_t$=4.56. MS (ESI+): mass calcd. for $C_{28}H_{30}N_4O_2$, 454.24; m/z found, 455.4 $[M+H]^+$. $^1$H NMR (400 MHz, CD$_3$OD): 8.12 (s, 1H), 7.99 (d, J=9.1 Hz, 2H), 7;84 (dd, J=1.7, 8.5 Hz, 1H), 7.62 (d, J=8.6 Hz, 1H), 7.30 (d, J=8.1 Hz, 2H), 7.23 (d, J=8.1 Hz, 2H), 7.09 (d, J=8.8 Hz, 2H), 4.19 (s, 2H), 3.94 (d, J=5.8 Hz, 2H), 3.50-3.45 (m, 2H), 3.02-2.94 (m, 2H), 2.30 (s, 3H), 2.09-2.03 (m, 3H), 1.65-1.52 (m, 2H).

Example 45

2-{4-[1-(4-Methoxy-benzyl)-piperidin-4-ylmethoxy]-phenyl}-1H-benzoimidazole-5-carboxylic acid amide

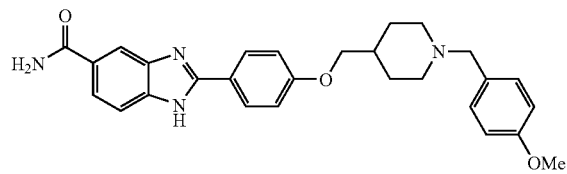

This compound was prepared using the methods outlined in Example 27, substituting 2-[4-(piperidin-4-ylmethoxy)-phenyl]-1H-benzoimidazole-5-carboxylic acid amide for 2-[4-(2-piperidin-2-yl-ethoxy)-phenyl]-1H-benzoimidazole-5-carboxylic acid amide and p-anisaldehyde for p-tolualdehyde. HPLC (Method C): $R_t$=4.48. MS (ESI+): mass calcd. for $C_{28}H_{30}N_4O_3$, 470.23; m/z found, 471.4 $[M+H]^+$. $^1$H NMR (500 MHz, CD$_3$OD): 8.05 (s, 1H), 7.94 (d, J=8.8 Hz, 2H), 7.70 (dd, J=1.6, 8.6 Hz, 1H), 7.51 (d, J=8.3 Hz, 1H), 7.15 (d, J=8.5 Hz, 2H), 6.99 (d, J=8.8 Hz, 2H), 6.79 (d, J=8.5 Hz, 2H), 3.83 (d, J=5.8 Hz, 2H), 3.69 (s, 3H), 3.40 (s, 2H), 2.87 (d, J=12.5 Hz, 2H), 1.97 (t, J=11.8 Hz, 2H), 1.79-1.73 (m, 3H), 1.41-1.31 (m, 2H).

Example 46

2-{4-[1-(4-Methoxy-benzyl)-piperidin-4-yl-methoxy]-phenyl}-1H-benzoimidazole-5-carboxylic acid amide

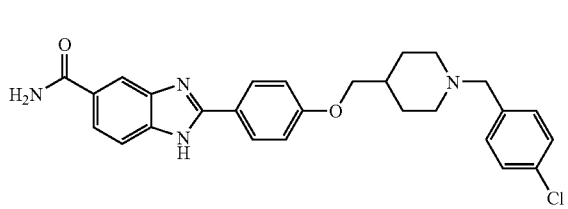

This compound was prepared using the methods outlined in Example 27, substituting 2-[4-(piperidin-4-ylmethoxy)-phenyl]-1H-benzoimidazole-5-carboxylic acid amide for 2-[4-(2-piperidin-2-yl-ethoxy)-phenyl]-1H-benzoimidazole-5-carboxylic acid amide and p-chlorobenzaldehyde for p-tolualdehyde. HPLC (Method C): $R_t$=4.63. MS (ESI+): mass calcd. for $C_{27}H_{27}ClN_4O_2$, 474.18; m/z found, 475.3 $[M+H]^+$. $^1$H NMR (400 MHz, CD$_3$OD): 8.12 (s, 1H), 7.99 (d, J=8.8 Hz, 2H), 7.83 (dd, J=1.5, 8.6 Hz, 1H), 7.62 (d, J=8.6 Hz, 1H), 7.46-7.41 (m, 4H), 7.09 (d, J=9.1 Hz, 2H), 4.24 (s, 2H), 3.94 (d, J=5.8 Hz, 2H), 3.51-3.45 (m, 2H), 3.04-2.95 (m, 2H), 2.14-2.02 (m, 3H), 1.66-1.53 (m, 2H), 1.25-1.18 (m, 1H).

Example 47

2-{4-[1-(3,4-Dichloro-benzyl)-piperidin-4-yl-methoxy]-phenyl}-1H-benzoimidazole-5-carboxylic acid amide

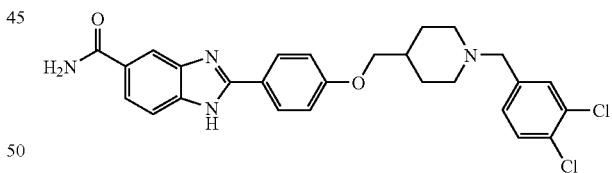

This compound was prepared using the methods outlined in Example 27, substituting 2-[4-(piperidin-4-ylmethoxy)-phenyl]-1H-benzoimidazole-5-carboxylic acid amide for 2-[4-(2-piperidin-2-yl-ethoxy)-phenyl]-1H-benzoimidazole-5-carboxylic acid amide and 3,4-dichlorobenzaldehyde for p-tolualdehyde. HPLC (Method C): $R_t$=4.84. MS (ESI+): mass calcd. for $C_{27}H_{26}Cl_2N_4O_2$, 508.14; m/z found, 509.3 $[M+H]^+$. $^1$H NMR (500 MHz, CD$_3$OD): 8.14 (s, 1H), 8.00 (d, J=8.5 Hz, 2H), 7.87 (dd, J=1.7, 8.5 Hz, 1H), 7.67 (d, J=1.9 Hz, 1H), 7.65 (d, J=8.5 Hz, 1H), 7.59 (d, J=8.0 Hz, 1H), 7.37 (dd, J=1.9, 8.2 Hz, 1H), 7.11 (d, J=8.8 Hz, 2H), 4.25 (s, 2H), 3.95 (d, J=4.9 Hz, 2H), 3.52-3.45 (m, 2H), 3.05-2.97 (m, 2H), 2.11-2.04 (m, 3H), 1.66-1.55 (m, 2H).

Example 48

2-{4-[2-(1-Acetyl-piperidin-2-yl)-ethoxy]-phenyl}-1H-benzoimidazole-5-carboxylic acid amide

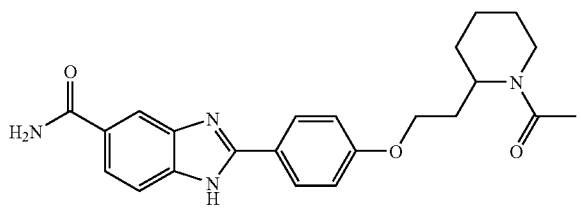

To a solution of 2-[4-(2-piperidin-2-yl-ethoxy)-phenyl]-1H-benzoimidazole-5-carboxylic acid amide (75 mg, 0.21 mmol) and 4-(dimethylamino)pyridine (13 mg, 0.10 mmol) in DMF (0.5 mL) was added acetic anhydride (20 μL, 0.23 mmol). The reaction mixture was stirred for 18 h before additional acetic anhydride (1 equiv.) and DMAP (3 equiv.) were added. After an additional 24 h, HPLC monitoring indicated reaction completion. The crude material was purified by reverse phase HPLC (C18; H$_2$O/CH$_3$CN/0.01% TFA), providing 39 mg (47%) of product. HPLC (Method C): R$_t$=4.70. MS (ESI+): mass calcd. for C$_{23}$H$_{26}$N$_4$O$_3$, 406.20; m/z found, 407.3 [M+H]$^+$. $^1$H NMR (400 MHz, CD$_3$OD): 8.18 (s, 1H), 8.03-7.96 (m, 3H), 7.71 (d, J=8.6 Hz, 1H), 7.18 (d, J=9.0 Hz, 1H), 7.13 (d, J=9.0 Hz, 1H), 4.41-4.26 (m, 1H), 4.15-3.94 (m, 1H), 4.04-3.98 (m, 1H), 3.69-3.64 (m, 1H), 2.67-2.60 (m, 1H), 2.41-2.21 (m, 1H), 1.97 (s, 3H), 1.98-1.85 (m, 1H), 1.72-1.52 (m, 5H), 1.48-1.23 (m, 1H).

Example 49

2-{4-[2-(1-Acetyl-piperidin-4-yl)-ethoxy]-phenyl}-1H-benzoimidazole-5-carboxylic acid amide

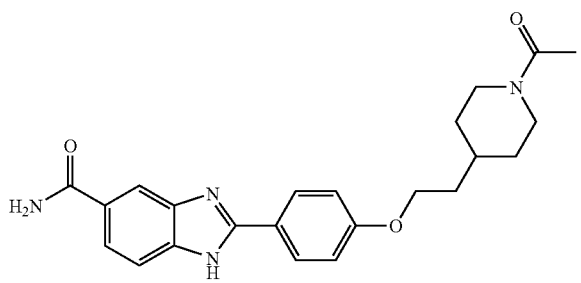

This compound was prepared using the methods outlined in Example 48, substituting 2-[4-(2-piperidin-4-yl-ethoxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): R$_t$=4.57. MS (ESI+): mass calcd. for C$_{23}$H$_{26}$N$_4$O$_3$, 406.20; m/z found, 407.4 [M+H]$^+$. $^1$H NMR (400 MHz, DMSO-d$_6$): 8.20-8.07 (m, 4H), 7.90 (d, J=8.2 Hz, 1H), 7.70 (d, J=7.8 Hz, 1H), 7.43 (br s, 1H), 7.23 (d, J=8.5 Hz, 2H), 4.42-4.31 (m, 1H), 4.21-4.11 (m, 2H), 3.86-3.75 (m, 2H), 3.07-2.96 (m, 1H), 1.99 (s, 3H), 1.82-1.67 (m, 5H), 1.22-0.98 (m, 2H).

Example 50

2-[4-(1-Acetyl-piperidin-3-yloxy)-phenyl]-1H-benzoimidazole-5-carboxylic acid amide

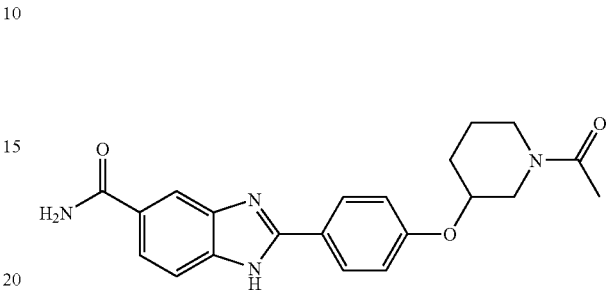

This compound was prepared using the methods outlined in Example 48, substituting 2-[4-(piperidin-3-yloxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): R$_t$=4.41. MS (ESI+): mass calcd. for C$_{21}$H$_{22}$N$_4$O$_3$, 378.17; m/z found, 379.3 [M+H]$^+$. $^1$H NMR (500 MHz, CD$_3$OD): 8.18 (s, 1H), 8.04-7.95 (m, 3H), 7.72 (d, J=8.5 Hz, 1H), 7.21-7.16 (m, 2H), 4.53-4.50 (m, 1H), 3.99-3.95 (m, 1H), 3.85-3.79 (m, 1H), 3.63-3.56 (m, 1H), 3.50-3.43 (m, 1H), 2.04-2.00 (m, 1H), 1.91 (s, 3H), 1.89-1.80 (m, 1H), 1.78-1.70 (m, 1H), 1.60-1.46 (m, 1H).

Example 51

2-[4-(1-Acetyl-piperidin-4-yloxy)-phenyl]-1H-benzoimidazole-5-carboxylic acid amide

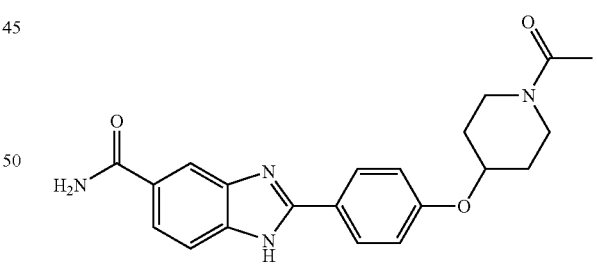

This compound was prepared using the methods outlined in Example 48, substituting 2-[4-(piperidin-4-yloxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): R$_t$=4.29. MS (ESI+): mass calcd. for C$_{21}$H$_{22}$N$_4$O$_3$, 378.43; m/z found, 379.3 [M+H]$^+$. $^1$H NMR (400 MHz, CD$_3$OD): 8.06 (s, 1H), 7.97 (d, J=8.0 Hz, 2H), 7.53 (s, 1H), 7.07 (d, J=7.2 Hz, 2H), 4.70-4.66 (m, 1H), 3.79-3.74 (m, 1H), 3.72-3.67 (m, 1H), 3.50-3.41 (m, 2H), 2.95 (m, 1H), 2.04 (s, 3H), 2.00-1.96 (m, 1H), 1.94-1.89 (m, 1H), 1.78-1.71 (m, 1H), 1.70-1.63 (m, 1H).

Example 52

2-[4-(1-Acetyl-piperidin-4-ylmethoxy)-phenyl]-1H-benzoimidazole-5-carboxylic acid amide

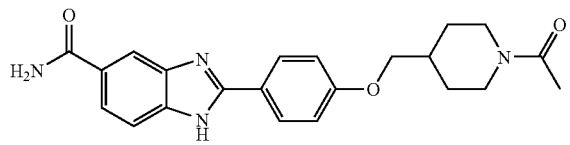

This compound was prepared using the methods outlined in Example 48, substituting 2-[4-(piperidin-4-ylmethoxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): $R_t$=4.41. MS (ESI+): mass calcd. for $C_{22}H_{24}N_4O_3$, 392.46; m/z found, 393.3 [M+H]$^+$. $^1$H NMR (500 MHz, CD$_3$OD): 8.06 (br s, 1H), 7.95 (dd, J=1.9, 7.0 Hz, 2H), 7.70 (d, J=8.4 Hz, 1H), 7.50 (br s, 1H), 7.01 (dd, J=2.0, 6.9 Hz, 2H), 4.49 (d, J=13.3 Hz, 1H), 3.88-3.86 (m, 3H), 3.08-3.07 (m, 1H), 2.60-2.54 (m, 1H), 2.03-2.02 (m, 1H), 2.02 (s, 3H), 1.93-1.80 (m, 2H), 1.38-1.13 (m, 2H).

Example 53

2-[4-(1-Acetyl-piperidin-3-ylmethoxy)-phenyl]-1H-benzoimidazole-5-carboxylic acid amide

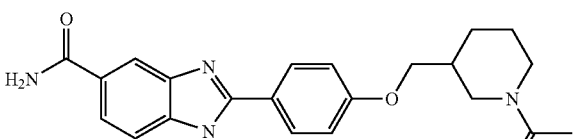

This compound was prepared using the methods outlined in Example 48, substituting 2-[4-piperidin-3-ylmethoxy)-phenyl]-1H-benzoimidazole-5-carboxylic acid amide for 2-[4-2-piperidin-2-yl-ethoxy)-phenyl]-1H-benzoimidazole-5-carboxylic acid amide. HPLC (Method C): $R_t$=4.50. MS (ESI+): mass calcd. for $C_{22}H_{24}N_4O_3$, 392.46; m/z found, 393.4 [M+H]$^+$. $^1$H NMR (500 MHz, CD$_3$OD): 8.05 (s, 1H), 7.97-7.94 (m, 2H), 7.70 (d, J=8.5 Hz, 1H), 7.52-7.51 (m, 1H), 7.04-7.00 (m, 2H), 4.46-4.42 (m, 1H), 4.07-3.73 (m, 1H), 3.95-3.81(m, 2H), 3.15-3.05 (m, 1H), 2.93-2.88 (m, 1H), 2.65-2.61 (m, 1H), 2.01 (d, J=6.5 Hz, 3H), 1.89-1.86 (m, 1H), 1.75-1.65 (m, 1H), 1.53-1.38 (m, 2H).

Example 54

2-{4-[2-(1-Benzoyl-piperidin-2-yl)-ethoxy]-phenyl}-1H-benzoimidazole-5-carboxylic acid amide

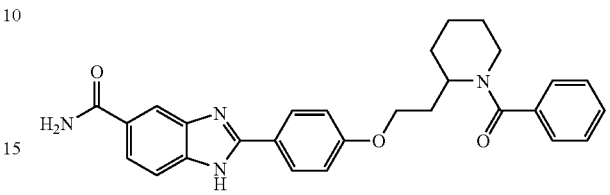

A solution of benzoic acid (75 mg, 0.62 mmol) and EDC (59 mg, 0.31 mmol) in DMF (1 mL) was stirred for 2 h and then was treated with 2-[4-(2-piperidin-2-yl-ethoxy)-phenyl]-1H-benzoimidazole-5-carboxylic acid amide (75 mg, 0.21 mmol) and DMAP (65 mg, 0.53 mmol). The mixture was stirred for 18 h, and the crude material was purified by reverse phase HPLC (C18; H$_2$O/CH$_3$CN/0.01% TFA), providing 46 mg (66%) of the title compound. HPLC (Method C): $R_t$=5.15. MS (ESI+): mass calcd. for $C_{28}H_{28}N_4O_3$, 468.22; m/z found, 469.4 [M+H]$^+$. $^1$H NMR (400 MHz, CD$_3$OD): 8.19 (s, 1H), 8.00-7.96 (m, 3H), 7.72 (d, J=8.6 Hz, 1H), 7.36-7.25 (m, 2H), 7.25-7.10 (m, 4H), 6.95-6.90 (m, 1H), 4.20-4.07 (m, 2H), 3.92-3.90 (m, 1H), 3.48-3.43 (m, 1H), 2.45-2.35 (m, 1H), 2.12-1.81 (m, 1H), 1.81-1.30 (m, 7H).

Example 55

2-{4-[2-(1-Benzoyl-piperidin-4-yl)-ethoxy]-phenyl}-1H-benzoimidazole-5-carboxylic acid amide

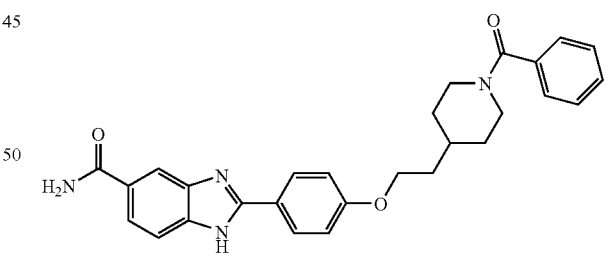

This compound was prepared using the methods outlined in Example 54, substituting 2-[4-(2-piperidin-4-yl-ethoxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): $R_t$=5.17. MS (ESI+): mass calcd. for $C_{28}H_{28}N_4O_3$, 468.22; m/z found, 469.4 [M+H]$^+$. $^1$H NMR (400 MHz, DMSO-d$_6$): 8.20-8.10 (m, 4H), 7.90 (d, J=8.3 Hz, 1H), 7.70 (d, J=8.3 Hz, 1H), 7.47-7.4.0 (m, 4H), 7.40-7.35 (m, 2H), 7.26-7.20 (m, 2H), 4.56-4.42 (m, 1H), 4.21-4.12 (m, 2H), 3.63-3.50 (m, 1H), 3.11-2.96 (m, 1H), 2.85-2.71 (m, 1H), 1.91-1.63 (m, 5H), 1.30-1.11 (m, 2H).

Example 56

2-[4-(1-Benzoyl-piperidin-4-ylmethoxy)-phenyl]-1H-benzoimidazole-5-carboxylic acid amide

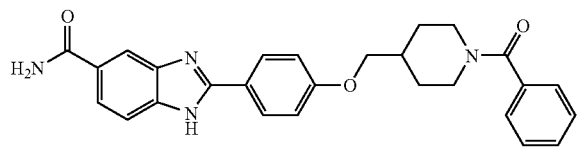

This compound was prepared using the methods outlined in Example 54, substituting 2-[4-(piperidin-4-ylmethoxy)-phenyl]-1H-benzoimidazole-5-carboxylic acid amide for 2-[4-(2-piperidin-2-yl-ethoxy)-phenyl]-1H-benzoimidazole-5-carboxylic acid amide. HPLC (Method C): $R_t$=6.05. MS (ESI+): mass calcd. for $C_{27}H_{26}N_4O_3$, 454.20; m/z found, 455.5 [M+H]$^+$. $^1$H NMR (400 MHz, CD$_3$OD): 8.05 (s, 1H), 7.94 (d, J=9.3 Hz, 2H), 7.70 (dd, J=1.5, 8.6 Hz, 1H), 7.51 (d, J=7.8 Hz, 1H), 7.38-7.35 (m, 2H), 7.34-7.30 (m, 3H), 6.99 (d, J=8.8 Hz, 2H), 4.61 (d, J=11.8 Hz, 1H), 3.87-3.85 (μm, 2H), 3.69 (d, J=12.1 Hz, 1H), 3.10-3.04 (m, 1H), 2.85-2.82 (m, 1H), 2.11-2.00 (m, 1H), 1.90 (d, J=11.6 Hz, 1H), 1.74 (d, J=8.6 Hz, 1H), 1.37-1.23 (m, 2H).

Example 57

Determination of Compound Inhibition of Human Cds1 Activity

For the determination of human Cds1 activity in the presence of Cds1 inhibitory compounds, such compounds were incubated in an aqueous mixture at pH 7.4 containing 50 mM HEPES, 100 mM NaCl, 10 mM MgCl$_2$, 5 nM recombinant human Cds1, 10 μM synthetic peptide substrate SGLYRSPSMPENLNRPR having an N-terminal biotin, 1 μM adenosine triphosphate, 50 μCi/mL of [γ-$^{33}$P] adenosine triphosphate, and a protease inhibitor mixture. The reaction mixtures were incubated at 37° C. for 3 h. The peptide substrate was captured from the reaction mixture by incubating the reaction mixture with streptavidin conjugated to agarose beads and 50 mM adenosine triphosphate. The agarose beads were washed repeatedly with a 0.1% solution of Tween®-20 in phosphate-buffered saline, pH 7.4. Enzyme activity at different Cds1 inhibitory compound concentrations was determined by measuring the amount of radioactive phosphate bound to the substrate peptide by scintillation counting. Results are expressed as IC$_{50}$ in Table 1 below.

TABLE 1

| Example | Cds1 Inhibition IC$_{50}$ (nM) |
|---|---|
| 1 | 73 |
| 2 | 52 |
| 3 | 72 |
| 4 | 80 |
| 5a | 54 |
| 5b | 400 |
| 6 | 836 |
| 7 | 122 |
| 8 | 110 |
| 9 | 174 |
| 10 | 233 |
| 11 | 52 |
| 12 | 63 |
| 13 | 659 |
| 14 | 84 |
| 15 | 89 |
| 16 | 134 |
| 17 | 65 |
| 18 | 93 |
| 19 | 41 |
| 20 | 84 |
| 21 | 138 |
| 22 | 97 |
| 23 | 180 |
| 24 | 710 |
| 25 | 231 |
| 26 | 158 |
| 27 | 61 |
| 28 | 74 |
| 29 | 53 |
| 30 | 30 |
| 31 | 45 |
| 32 | 90 |
| 33 | 90 |
| 34 | 95 |
| 35 | 82 |
| 36 | 157 |
| 37 | 14 |
| 38 | 37 |
| 39 | 57 |
| 40 | 55 |
| 41 | 35 |
| 42 | 75 |
| 43 | 70 |
| 44 | 76 |
| 45 | 67 |
| 46 | 60 |
| 47 | 110 |
| 48 | 292 |
| 49 | 86 |
| 50 | 100 |
| 51 | 140 |
| 52 | 78 |
| 53 | 140 |
| 54 | 52 |
| 55 | 23 |
| 56 | 52 |

Example 58

Determination of the Effect of Cds1 Inhibitory Compounds on Radiation-induced Apoptosis in Isolated Primary Cells Spleen cells were isolated from C57/BL6 mice as follows: spleens were disrupted by grinding between two frosted glass slides, and cells were passed through a cell strainer. Erythrocytes were lysed by incubation in ammonium chloride solution followed by careful washing of cells in isotonic medium. The spleen cells were plated in 60 mm petri dishes at 5×10$^6$ cells/mL in RPMI medium containing 10% fetal calf serum and Cds1 inhibitor. One hour after plating of cells with compound, the cells were dosed with 0.5-1 Gy from a $^{137}$Cs γ-radiation source. Determination of apoptotic cells by Annexin V staining was performed using the Annexin V-FITC Apoptosis Detection Kit™ (Cat# PF032 Oncogene Research Products) according to the manufacturer's instructions. Briefly, 6-24 h after irradiation, the cells were washed with buffered isotonic salt solution and suspended at 1×10$^6$ cells/mL in binding buffer (10 mM HEPES pH 7.4, 150 mM NaCl, 2.5 mM CaCl$_2$, 1 mM MgCl$_2$, 4% bovine serum albumin) containing 80 ng/mL Annexin V labeled with FITC and 0.4 µg/mL anti-B220 antibody labeled with allophycocyanin. The cells were then pelleted and re-suspended in binding buffer containing 0.6 µg/mL propidium iodide. The stained cells were analyzed on a FACS machine (Fluorescence Activated Cell Sorter™, Becton Dickinson). The fraction of viable, non-apoptotic cells was determined by quantifying the number of cells that did not stain with propidium iodide or Annexin V versus the total number of cells. Fractions of non-apoptotic B-cells or total cells were determined separately based on staining with the B220 antibody mentioned above.

Example 59

Determination of Effect of Cds1 Inhibitors on Radiation-induced Caspase Activity in Human CD4$^+$ T-Cells Human CD4$^+$ T-cells were isolated from the blood of healthy donors as follows. Whole heparinized blood was layered over Ficoll-Paque (Amersham Pharmacia Biotech, Uppsala, Sweden) and centrifuged 20 min at 560 g. Mononuclear cells were harvested and subjected to positive selection with anti-human CD4-coated MACS MicroBeads (Miltenyi, Auburn, Calif.). Purified CD4$^+$ T-cells were transferred to growth medium (RPMI with 10% fetal calf serum, 50% IU/mL penicillin and 50 µg/mL streptomycin). The cells were dispensed to wells of 96-well-tissue culture plates at 200,000 cells/well. Either a Cds1 inhibitory compound in DMSO or the same volume of vehicle was added to each well. The reaction mixtures were incubated at 37° C. for 1 h, exposed to 10 Gy of γ-radiation, and then incubated for 24 h. The CD4$^+$ T-cells were harvested by centrifugation and lysed to release caspase-3. Caspase-3 and caspase-7 specific fluorogenic peptide substrate Acetyl-Asp-Glu-Val-Asp-(7-amino-4-methyl-coumarin) was added to each sample (final concentration=100 µM). Three hours after the addition of peptide, the caspase activity of each sample was determined fluorometrically using a Millipore Cytofluor fluorescent plate reader ($\lambda_{ex}$=360 nm, $\lambda_{em}$=460 nm).

Example 60

Determination of the Effect of Cds1 Inhibitory Compounds on Radiation-induced Apoptosis in Human CD4$^+$ T-Cells.

Human CD4$^+$ T-cells were isolated from the blood of healthy donors and cultured as described in Example 59. The cells were dispensed to wells of 96-well tissue culture plates at 200,000 cells/well. Either a Cds1 inhibitory compound in DMSO or the same volume of vehicle was added to each well. The reaction mixtures were incubated at 37° C. for 1 h, exposed to 10 Gy of γ-radiation, and then incubated for 24 h. Determination of apoptotic cells by Annexin V staining was performed as described in Example 58.

Example 61

Determination of the Effect of Cds1 Inhibitory Compounds on Radiation-induced Apoptosis in Splenocytes In Vivo Female C57/BL mice, 6-8 weeks of age, are dosed by oral gavage or by injection with Cds1 inhibitory compound before and at regular intervals after radiation exposure. One to three hours after first compound dose, the animals are irradiated with γ-rays administered to the whole animal at adose between 0.5 and 4 Gy. At times between 4 and 24 h after irradiation, the animals are sacrificed, and the tissues of interest are excised. Cell apoptosis is quantified using Annexin V staining as described in Example 58. Apoptosis can be studied in a variety of tissues. In some cases other methods for quantification of apoptosis than the method described in Example 58 may be more appropriate. Thus, apoptosis can also be determined by detection of DNA degradation by TUNEL staining, as described by Darzynkiewicz and Bedner (In *Analysis of Apoptotic Cells by Flow and Laser Scanning Cytometry*, Reed, J. C., Ed.; Methods of Enzymology, Vol. 322; Academic Press: San Diego, 2000; 18-39). Briefly, cells or tissues are fixed with formaldehyde and permeabilized with ethanol, and DNA ends are then labeled by attaching nucleotide derivatives such as BrdUTP using the enzyme terminal deoxynucleotidyl transferase. DNA ends can then be detected by incubating the cells or tissues with fluorescently-labeled antibodies reactive with BrdU. Quantification can be done by laser scanning cytometry, by visual microscopical examination or by FACS.

What is claimed is:

1. A compound having Cds1 modulating activity of formula (I):

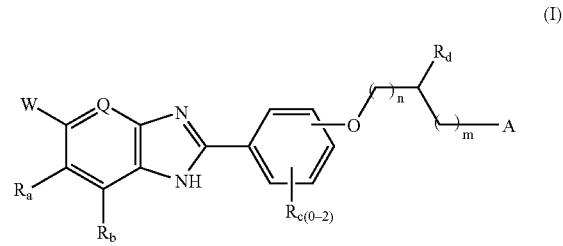

(I)

wherein
W is —COOH, —(CO)NH$_2$, or —(SO$_2$)NH$_2$;
Q is N or CH;
$R_a$ and $R_b$ are each independently selected from —H and halogen;
$R_c$ is absent or is independently selected from the group consisting of —OH, —CF$_3$, —C$_{1-4}$alkyl, —OC$_{1-4}$alkyl, —NO$_2$, and halo;
n is selected from the group consisting of 0, 1, and 2;
m is selected from the group consisting of 0, 1, and 2;
$R_d$ is —H or —C$_{1-4}$alkyl, optionally mono- or di-substituted with a substituent selected from the group consisting of —NH$_2$, —NHC$_{1-4}$alkyl, —N(C$_{1-4}$alkyl)$_2$, —OH, and —OC$_{1-4}$alkyl;
A is selected from the group consisting of —CR$_e$OH and —R$_y$R$_z$, where if A is —NR$_y$R$_z$, m+n must be greater than zero;
$R_e$ is —H or —C$_{1-4}$alkyl, optionally mono- or di-substituted —C$_{1-4}$alkyl with a substituent selected from the group consisting of —NH$_2$, —NHC$_{1-4}$alkyl, —N(C$_{1-4}$alkyl)$_2$, —OH, —OC$_{1-4}$alkyl, —CF$_3$, and fluoro;
alternatively, $R_d$ and $R_e$ may be taken together with their carbons of attachment to form an aliphatic hydrocarbon ring, said ring having four to seven members, optionally having one or two unsaturated bonds in the ring, and optionally substituted with a substituent selected from the group consisting of —C$_{1-4}$alkyl, —OC$_{1-4}$alkyl, and fluoro;

$R_y$ is independently selected from the group consisting of —H, —$C_{1-4}$alkyl optionally substituted with —$OC_{1-4}$alkyl, and benzyl optionally mono- or di-substituted with —$OC_{1-4}$alkyl, —$C_{1-4}$alkyl, or halo;

alternatively, $R_d$ and $R_y$ may be taken together with their atoms of attachment to form a five to eight-membered heterocyclic ring, with the heterocyclic ring having zero or one unsaturated bonds, having zero, one, or two carbon members which is a carbonyl, having zero or one additional heteroatom members selected from the group consisting of O, S, —N=, >NH, and >N$C_{1-4}$alkyl and separated from the nitrogen of $R_y$ attachment by at least one carbon member, and optionally having a substituent selected from the group consisting of —$C_{1-4}$alkyl, —$OC_{1-4}$alkyl, and fluoro;

$R_z$ is —H or is selected from the group consisting of —$C_{1-6}$alkyl, —$C_{3-6}$cycloalkyl, —$C_{1-4}$alkyl$C_{3-6}$cycloalkyl, phenyl, benzyl, pyridylmethyl, —C(O)$C_{1-6}$alkyl, —C(O)phenyl, —C(O)pyridyl, —C(O)O$C_{1-6}$alkyl, and —C(O)Obenzyl, each optionally mono-, di-, or tri-substituted with a substituent selected from the group consisting of —$NH_2$, —NH$C_{1-4}$alkyl, —N($C_{1-4}$alkyl)$_2$, —OH, —$OC_{1-4}$alkyl, —$C_{1-4}$alkyl, and halo; and alternatively, $R_y$ and $R_z$ may be taken together with the nitrogen of attachment to form an otherwise aliphatic hydrocarbon ring, said ring having five to seven members, optionally having one carbon replaced with >O, >S(=O)$_{0-2}$, =N—, >NH, and >N($C_{1-4}$alkyl), optionally having one or two unsaturated bonds in the ring, and optionally having a substituent selected from the group consisting of —$C_{1-4}$alkyl, —$OC_{1-4}$alkyl, and fluoro;

and enantiomers, diastereomers, and pharmaceutically acceptable salts, esters or amides thereof.

2. The compound of claim 1 wherein W is —(CO)$NH_2$.

3. The compound of claim 1 wherein Q is CH.

4. The compound of claim 1 wherein $R_a$ and $R_b$ are each independently —H, —Cl, or —F.

5. The compound of claim 1 wherein $R_a$ is —H and $R_b$ is —Cl or —F.

6. The compound of claim 1 wherein $R_a$ and $R_b$ are —H.

7. The compound of claim 1 wherein $R_c$ is absent or is selected from the group consisting of —OH, —$CH_3$, —$CH_2CH_3$, —F, —Cl, —Br, —I, —$CF_3$, and —$OCH_3$.

8. The compound of claim 1 wherein $R_c$ is selected from the group consisting of —F, —Cl, —$CH_3$, and —$OCH_3$.

9. The compound of claim 1 wherein $R_c$ is absent.

10. The compound of claim 1 wherein $R_d$ is selected from the group consisting of —H, —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, and —C($CH_3$)$_3$, where the alkyl members are optionally mono- or di-substituted.

11. The compound of claim 1 wherein $R_d$ is selected from the group consisting of —H, —$CH_3$, —$CH_2CH_3$, —$CH_2CH_2OCH_3$, and —$CH_2CH_2N(CH_3)_2$.

12. The compound of claim 1 wherein $R_d$ is —H.

13. The compound of claim 1 wherein $R_e$ is selected from the group consisting of —H, —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, and —C($CH_3$)$_3$, where the alkyl members are optionally mono- or di-substituted.

14. The compound of claim 1 wherein $R_e$ is selected from the group consisting of —H, —$CH_3$, —$CH_2CH_3$, —$CH_2CH_2OCH_3$, and —$CH_2CH_2N(CH_3)_2$.

15. The compound of claim 1 wherein $R_e$ is —H or —$CH_3$.

16. The compound of claim 1 wherein $R_d$ and $R_e$ taken together with their carbons of attachment form a hydrocarbon ring selected from the group consisting of cyclopentyl, cyclopentenyl, cyclohexyl, fluorocyclohexyl, methoxycyclohexyl, and cycloheptyl.

17. The compound of claim 1 wherein $R_d$ and $R_e$ taken together with their carbons of attachment form cyclopentyl or cyclohexyl.

18. The compound of claim 1 wherein $R_y$ is selected from the group consisting of —H, —$CH_3$, —$CH_2CH_3$, —$CH_2CH_2CH_3$, —CH($CH_3$)$_2$, —$CH_2(CH_2CH_2CH_3$, —CH($CH_3$)$CH_2CH_3$, and —C($CH_3$)$_3$, where the alkyl members are optionally mono- or di-substituted.

19. The compound of claim 1 wherein $R_y$ is selected from the group consisting of —H, —$CH_3$, —$CH_2CH_3$, —$CH_2CH_2OCH_3$, —$CH_2CH_2CH_3$, —CH($CH_3$)$_2$, —$CH_2CH_2N(CH_3)_2$, and —$CH_2CH_2CH_2CH_3$.

20. The compound of claim 1 wherein $R_y$ is —H or —$CH_3$.

21. The compound of claim 1 wherein $R_d$ and $R_y$ taken together with their atoms of attachment form a heterocyclic ring selected from the group consisting of pyrrolidine, pyrrolidinone, 2,3-dihydropyrrole, piperidine, piperidinone, morpholine, thiomorpholine, piperazine, and piperazinone, where the rings are optionally substituted.

22. The compound of claim 1 wherein $R_d$ and $R_y$ taken together with their atoms of attachment form a heterocyclic ring selected from the group consisting of pyrrolidinyl, piperidinyl, 4-fluoropiperidinyl, 4-methoxy piperidinyl, and 3-methylpiperidinyl.

23. The compound of claim 1 wherein $R_d$ and $R_y$ taken together with their atoms of attachment form a piperidine ring.

24. The compound of claim 1 wherein $R_z$ is —H or is selected from the group consisting of —$CH_3$, —$CH_2CH_3$, —$CH_2CH_2CH_3$, —CH($CH_3$)$_2$, —$CH_2CH_2CH_2CH_3$, cyclopentyl, cyclohexyl, cyclopropylethyl, phenyl, benzyl, pyridylmethyl, acetyl, propionyl, benzoyl, —C(O)pyridyl, —C(O)OC($CH_3$)$_3$, and —C(O)Obenzyl, where each group member is optionally mono-, di-, or tri-substituted.

25. The compound of claim 1 wherein $R_z$ is selected from the group consisting of —$CH_3$, 4-methylbenzyl, 4-methoxybenzyl, 4-chlorobenzyl, 3,4-dichlorobenzyl, acetyl, trifluoroacetyl, benzoyl, and —C(O)C($CH_3$)$_3$.

26. The compound of claim 1 wherein $R_y$ and $R_z$ are taken together with the nitrogen of attachment to form a ring selected from the group consisting of pyrrolidine, pyrrolidinone, 2,3-dihydropyrrole, piperidine, piperidinone, morpholine, thiomorpholine, piperazine, and piperazinone, where said rings are optionally substituted.

27. The compound of claim 1 wherein $R_y$ and $R_z$ are taken together with the nitrogen of attachment to form a ring selected from the group consisting of pyrrolidinyl, piperidinyl, 4-fluoropiperidinyl, 4-methoxypiperidinyl, and 3-methylpiperidinyl.

28. The compound of claim 1 wherein $R_y$ and $R_z$ taken together with their atoms of attachment form a piperidine ring.

29. A compound selected from the group consisting of:
2-[4-(3-Hydroxy-propoxy)-phenyl]-1H-benzoimidazole-5-carboxylic acid amide;
2-[4-(2-Hydroxy-ethoxy)-phenyl]-1H-benzoimidazole-5-carboxylic acid amide;
2-[4-(3-Hydroxy-cyclopentyloxy)-phenyl]-1H-benzoimidazole-5-carboxylic acid amide;
2-[4-(4-Hydroxy-cyclohexyloxy)-phenyl]-1H-benzoimidazole-5-arboxylic acid amide;

2-[4-(4-Hydroxy-cyclohexylmethoxy)-phenyl]-1H-benzoimidazole-5-carboxylic acid amide (cis and trans isomers);

2-[3-(3-Dimethylamino-propoxy)phenyl]-1H-benzoimidazole-5-carboxylic acid amide;

2-[4-(3-Dimethylamino-propoxy)-phenyl]-1H-benzoimidazole-5-carboxylic acid amide;

2-[4-(3-Piperidin-1-yl-propoxy)-phenyl]-1H-benzoimidazole-5-carboxylic acid amide;

2-[4-(2-Piperidin-1-yl-ethoxy)-phenyl]-1H-benzoimidazole-5-carboxylic acid amide;

2-[4-(1-Methyl-piperidin-4-yloxy)-phenyl]-1H-benzoimidazole-5-carboxylic acid amide;

2-[4-(1-Benzyl-piperidin-4-yloxy)-phenyl]-1H-benzoimidazole-5-carboxylic acid amide;

2-[4-(1-Benzyl-piperidin-3-yloxy)-phenyl]-1H-benzoimidazole-5-carboxylic acid amide;

2-[4-(1-Methyl-pyrrolidin-3-yloxy)-phenyl]-1H-benzoimidazole-5-carboxylic acid amide;

2-[4-(1-Benzyl-pyrrolidin-3-yloxy)-phenyl]-1H-benzoimidazole-5-carboxylic acid amide;

2-{2-[4-(5-Carbamoyl-1H-benzoimidazol-2-yl)-phenoxy]-ethyl}-piperidine-1-carboxylic acid tert-butyl ester;

4-{2-[4-(5-Carbamoyl-1H-benzoimidazol-2-yl)-phenoxy]-ethyl}-piperidine-1-carboxylic acid tert-butyl ester;

3-[4-(5-Carbamoyl-1H-benzoimidazol-2-yl)-phenoxy]-piperidine-1-carboxylic acid tert-butyl ester;

4-[4-(5-Carbamoyl-1H-benzoimidazol-2-yl)-phenoxy]-piperidine-1-carboxylic acid tert-butyl-ester;

4-[4-(5-Carbamoyl-1H-benzoimidazol-2-yl)-phenoxymethyl]-piperidine-1-carboxylic acid tert-butyl ester;

3-[4-(5-Carbamoyl-1H-benzoimidazol-2-yl)-phenoxymethyl]-piperidine-1-carboxylic acid tert-butyl ester;

2-[4-(2-Piperidin-2-yl-ethoxy)-phenyl]-1H-benzoimidazole-5-carboxylic acid amide;

2-[4-(2-Piperidin-4-yl-ethoxy)-phenyl]-1H-benzoimidazole-5-carboxylic acid amide;

2-[4-(Piperidin-3-yloxy)-phenyl]-1H-benzoimidazole-5-carboxylic acid amide;

2-[4-(Piperidin-4-yloxy)-phenyl]-1H-benzoimidazole-5-carboxylic acid amide;

2-[4-(Piperidin-4-ylmethoxy)-phenyl]-1H-benzoimidazole-5-carboxylic acid amide;

2-[4-(Piperidin-3-ylmethoxy)-phenyl]-1H-benzoimidazole-5-carboxylic acid amide;

2-(4-{2-[1-(4-Methyl-benzyl)-piperidin-2-yl]-ethoxy}-phenyl)-1H-benzoimidazole-5-carboxylic acid amide;

2-(4-{2-[1-(4-Methoxy-benzyl)-piperidin-2-yl]-ethoxy}-phenyl)-1H-benzoimidazole-5-carboxylic acid amide;

2-(4-{2-[1-(4-Chloro-benzyl)-piperidin-2-yl]-ethoxy}-phenyl)-1H-benzoimidazole-5-carboxylic acid amide;

2-(4-{2-[1-(3,4-Dichloro-benzyl)-piperidin-2-yl]-ethoxy}-henyl)-1H-benzoimidazole-5-carboxylic acid amide;

2-(4-{2-(1-Benzyl-piperidin-2-yl)-ethoxy-}-phenyl)-1H-benzoimidazole-5-carboxylic acid amide;

2-{4-[2-(1-Benzyl-piperidin-4-yl)-ethoxy]-phenyl}-1H-benzoimidazole-5-carboxylic acid amide;

2-(4-{2-[1-(4-Methyl-benzyl)-piperidin-4-yl]-ethoxy}-phenyl)-1H-benzoimidazole-5-carboxylic acid amide;

2-(4-{2-[1-(4-Methoxy-benzyl)-piperidin-4-yl]-ethoxy}-phenyl)-1H-benzoimidazole-5-carboxylic acid amide;

2-(4-{2-[1-(4-Chloro-benzyl)-piperidin-4-yl]-ethoxy}-phenyl)-1H-benzoimidazole-5-carboxylic acid amide;

2-(4-{2-[1-3,4-Dichloro-benzyl)-piperidin-4-yl]-ethoxy}-phenyl)-1H-benzoimidazole-5-carboxylic acid amide;

2-{4-[1-(4-Chloro-benzyl)-piperidin-3-yloxy]-phenyl}-1H-benzoimidazole-5-carboxylic acid amide;

2-[4-(1-Benzyl-piperidin-3-ylmethoxy)-phenyl]-1H-benzoimidazole-5-carboxylic acid amide;

2-{4-[1-(4-Methyl-benzyl)-piperidin-3-ylmethoxy]-phenyl}-1H-benzoimidazole-5-carboxylic acid amide;

2-{4-[1-(4-Methoxy-benzyl)-piperidin-3-ylmethoxy]-phenyl}-1H-benzoimidazole-5-carboxylic acid amide;

2-{4-[1-(4-Chloro-benzyl)-piperidin-3-ylmethoxy]-phenyl}-1H-benzoimidazole-5-carboxylic acid amide;

2-{4-[1-(3,4-Dichloro-benzyl)-piperidin-3-ylmethoxy]-phenyl}-1H-benzoimidazole-5-carboxylic acid amide;

2-[4-(1-Benzyl-piperidin-4-ylmethoxy)-phenyl]-1H-benzoimidazole-5-carboxylic acid amide;

2-{4-[1-(4-Methyl-benzyl)-piperidin-4-ylmethoxy]-phenyl}-1H-benzoimidazole-5-carboxylic acid amide;

2-{4-[1-(4-Methoxy-benzyl)-piperidin-4-ylmethoxy]-phenyl}-1H-benzoimidazole-5-carboxylic acid amide;

2-{4-[1-(4-Methoxy-benzyl)-piperidin-4-ylmethoxy]-phenyl}-1H-benzoimidazole-5-carboxylic acid amide;

2-{4-[1-(3,4-Dichloro-benzyl)-piperidin-4-ylmethoxy]-phenyl}-1H-benzoimidazole-5-carboxylic acid amide;

2-{4-[2-(1-Acetyl-piperidin-2-yl)-ethoxy]-phenyl}-1H-benzoimidazole-5-carboxylic acid amide;

2-{4-[2-(1-Acetyl-piperidin-4-yl)-ethoxy]-phenyl}-1H-benzoimidazole-5-carboxylic acid amide;

2-[4-(1-Acetyl-piperidin-3-yloxy)-phenyl]-1H-benzoimidazole-5-carboxylic acid amide;

2-[4-(1-Acetyl-piperidin-4-yloxy)-phenyl]-1H-benzoimidazole-5-carboxylic acid amide;

2-[4-(1-Acetyl-piperidin-4-ylmethoxy)-phenyl]-1H-benzoimidazole-5-carboxylic acid amide;

2-[4-(1-Acetyl-piperidin-3-ylmethoxy)-phenyl]-1H-benzoimidazole-5-carboxylic acid amide;

2-{4-[2-(1-Benzoyl-piperidin-2-yl)-ethoxy]-phenyl}-1H-benzoimidazole-5-carboxylic acid amide;

2-{4-[2-(1-Benzoyl-piperidin-4-yl)-ethoxy]-phenyl}-1H-benzoimidazole-5-carboxylic acid amide; and 2-[4-(1-Benzoyl-piperidin-4-ylmethoxy)-phenyl]-1H-benzoimidazole-5-carboxylic acid amide.

30. The compound of claim 1 selected from the group consisting of:

2-[4-(2-Hydroxy-ethoxy)-phenyl]-1H-benzoimidazole-5-carboxylic acid amide;

cis-2-[4-(4-Hydroxy-cyclohexylmethoxy)-phenyl]-1H-benzoimidazole-5-carboxylic acid amide;

2-[4-(1-Benzyl-piperidin-4-yloxy)-phenyl]-1H-benzoimidazole-5-carboxylic acid amide;

2-[4-(1-Benzyl-piperidin-3-yloxy)-phenyl]-1H-benzoimidazole-5-carboxylic acid amide;

3-[4-(5-Carbamoyl-1H-benzoimidazol-2-yl)-phenoxy]-piperidine-1-carboxylic acid tert-butyl ester;

4-[4-(5-Carbamoyl-1H-benzoimidazol-2-yl)-phenoxymethyl]-piperidine-1-carboxylic acid tert-butyl ester;

2-(4-{2-[1-(4-Methylbenzyl)-piperidin-2-yl]-ethoxy}-phenyl)-1H-benzoimidazole-5-carboxylic acid amide;

2-(4-{2-[1-(4-Methoxybenzyl)-piperidin-2-yl]-ethoxy}-phenyl)-1H-benzoimidazole-5-carboxylic acid amide;

2-(4-{2-[1-(4-Chloro-benzyl)-piperidin-2-yl]-ethoxy}-phenyl)-1H-benzoimidazole-5-carboxylic acid amide;

2-(4-{2-[1-(3,4-Dichloro-benzyl)-piperidin-2-yl]-ethoxy}-phenyl)-1H-benzoimidazole-5-carboxylic acid amide;

2-{4-[2-(1-Benzyl-piperidin-2-yl)-ethoxy]-phenyl}-1H-benzoimidazole-5-carboxylic acid amide;
2-{4-[1-(4-Chloro-benzyl)-piperidin-3-yloxy]-phenyl}-1H-benzoimidazole-5-carboxylic acid amide;
2-[4-(1-Benzyl-piperidin-3-ylmethoxy)-phenyl]-1H-benzoimidazole-5-carboxylic acid amide;
2-{4-[1-(4-Methyl-benzyl)-piperidin-3-ylmethoxy]-phenyl}-1H-benzoimidazole-5-carboxylic acid amide;
2-{4-[1-(4-Methoxy-benzyl)-piperidin-3-ylmethoxy]-phenyl}-1H-benzoimidazole-5-carboxylic acid amide;
2-{4-[1-(4-Chloro-benzyl)-piperidin-3-ylmethoxy]-phenyl}-1H-benzoimidazole-5-carboxylic acid amide;
2-{4-[1-(4-Methoxy-benzyl)-piperidin-4-ylmethoxy]-phenyl}-1H-benzoimidazole-5-carboxylic acid amide;
2-{4-[1-(4-Methoxy-benzyl)-piperidin-4-ylmethoxy]-phenyl}-1H-benzoimidazole-5-carboxylic acid amide;
2-{4-[2-(1-Benzoyl-piperidin-2-yl)-ethoxy]-phenyl}-1H-benzoimidazole-5-carboxylic acid amide;
2-{4-[2-(1-Benzoyl-piperidin-4-yl)-ethoxy]-phenyl}-1H-benzoimidazole-5-carboxylic acid amide; and
2-[4-(1-Benzoyl-piperidin-4-ylmethoxy)-phenyl]-1H-benzoimidazole-5-carboxylic acid amide.

31. The compound of claim 1 selected from the group consisting of:
4-[4-(5-Carbamoyl-1H-benzoimidazol-2-yl)-phenoxymethyl]-piperidine-1-carboxylic acid tert-butyl ester;
2-(4-{2-[1-(4-Chloro-benzyl)-piperidin-2-yl]-ethoxy}-phenyl)-1H-benzoimidazole-5-carboxylic acid amide;
2-(4-{2-[1-(3,4-Dichloro-benzyl)-piperidin-2-yl]-ethoxy}-phenyl)-1H-benzoimidazole-5-carboxylic acid amide;
2-{4-[2-(1-Benzyl-piperidin-2-yl)-ethoxy]-phenyl}-1H-benzoimidazole-5-carboxylic acid amide;
2-{4-[1-(4-Chloro-benzyl)-piperidin-3-yloxy]-phenyl}-1H-benzoimidazole-5-carboxylic acid amide;
2-[4-(1-Benzyl-piperidin-3-ylmethoxy)-phenyl]-1H-benzoimidazole-5-carboxylic acid amide;
2-{4-[1-(4-Chloro-benzyl)-piperidin-3-ylmethoxy]-phenyl}-1H-benzoimidazole-5-carboxylic acid amide;
2-{4-[2-(1-Benzoyl-piperidin-2-yl)-ethoxy]-phenyl}-1H-benzoimidazole-5-carboxylic acid amide;
2-{4-[2-(1-Benzoyl-piperidin-4-yl)-ethoxy]-phenyl}-1H-benzoimidazole-5-carboxylic acid amide; and
2-[4-(1-Benzoyl-piperidin-4-ylmethoxy)-phenyl]-1H-benzoimidazole-5-carboxylic acid amide.

32. A pharmaceutical composition comprising a pharmaceutically acceptable carrier and a therapeutic amount of at least one compound having Cds-1 modulating activity of formula (I):

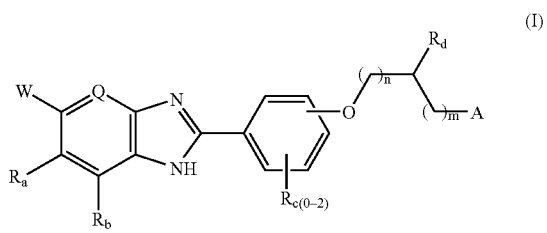

(I)

wherein
W is —COOH, —(CO)NH$_2$, or —(SO$_2$)NH$_2$;
Q is N or CH;
R$_a$ and R$_b$ are each independently selected from —H and halogen;

R$_c$ is absent or is independently selected from the group consisting of —OH, —CF$_3$, —C$_{1-4}$alkyl, —OC$_{1-4}$alkyl, —NO$_2$, and halo;
n is selected from the group consisting of 0, 1, and 2;
m is selected from the group consisting of 0, 1, and 2;
R$_d$ is —H or —C$_{1-4}$alkyl, optionally mono- or di-substituted with a substituent selected from the group consisting of —NH$_2$, —NHC$_{1-4}$alkyl, —N(C$_{1-4}$alkyl)$_2$, —OH, and —OC$_{1-4}$alkyl;
A is selected from the group consisting of —CR$_e$OH and —NR$_y$R$_z$, where if A is —NR$_y$R$_z$, m+n must be greater than zero;
R$_e$ is —H or —C$_{1-4}$alkyl, optionally mono- or di-substituted —C$_{1-4}$alkyl with a substituent selected from the group consisting of —NH$_2$, —NHC$_{1-4}$alkyl, —N(C$_{1-4}$alkyl)$_2$, —OH, —OC$_{1-4}$alkyl, —CF$_3$, and fluoro;
alternatively, R$_d$ and R$_e$ may be taken together with their carbons of attachment to form an aliphatic hydrocarbon ring, said ring having four to seven members, optionally having one or two unsaturated bonds in the ring, and optionally substituted with a substituent selected from the group consisting of —C$_{1-4}$alkyl, —OC$_{1-4}$alkyl, and fluoro;
R$_y$ is independently selected from the group consisting of —H, —C$_{1-4}$alkyl optionally substituted with —OC$_{1-4}$alkyl, and benzyl optionally mono- or di-substituted with —OC$_{1-4}$alkyl, —C$_{1-4}$alkyl, or halo;
alternatively, R$_d$ and R$_y$ may be taken together with their atoms of attachment to form a five to eight-membered heterocyclic ring, with the heterocyclic ring having zero or one unsaturated bonds, having zero, one, or two carbon members which is a carbonyl, having zero or one additional heteroatom members selected from the group consisting of O, S, —N=, >NH, and >NC$_{1-4}$alkyl and separated from the nitrogen of R$_y$ attachment by at least one carbon member, and optionally having a substituent selected from the group consisting of —C$_{1-4}$alkyl, —OC$_{1-4}$alkyl, and fluoro;
R$_z$ is —H or is selected from the group consisting of —C$_{1-6}$alkyl, —C$_{3-6}$cycloalkyl, —C$_{1-4}$alkylC$_{3-6}$cycloalkyl, phenyl, benzyl, pyridylmethyl, —C(O)C$_{1-6}$alkyl, —C(O)phenyl, —C(O)pyridyl, —C(O)OC$_{1-6}$alkyl, and —C(O)Obenzyl, each optionally mono-, di-, or tri-substituted with a substituent selected from the group consisting of —NH$_2$, —NHC$_{1-4}$alkyl, —N(C$_{1-4}$alkyl)$_2$, —OH, —OC$_{1-4}$alkyl, —C$_{1-4}$alkyl, and halo; and
alternatively, R$_y$ and R$_z$ may be taken together with the nitrogen of attachment to form an otherwise aliphatic hydrocarbon ring, said ring having five to seven members, optionally having one carbon replaced with >O, >S(=O)$_{0-2}$, =N—, >NH, and >N(C$_{1-4}$alkyl), optionally having one or two unsaturated bonds in the ring, and optionally having a substituent selected from the group consisting of —C$_{1-4}$alkyl, —OC$_{1-4}$alkyl, and fluoro;
and enantiomers, diastereomers, and pharmaceutically acceptable salts, esters or amides thereof.

33. A compound of claim 1 isotopically-labeled to be detectable by PET or SPECT.

* * * * *